United States Patent
Cheve et al.

(10) Patent No.: US 9,550,772 B2
(45) Date of Patent: Jan. 24, 2017

(54) AZAINDOLE DERIVATIVES AS MULTI KINASE INHIBITORS

(71) Applicant: ORIBASE PHARMA, Montpellier (FR)

(72) Inventors: Gwénaël Cheve, Lunel (FR); Bénédicte Dayde-Cazals, Montpellier (FR); Bénédicte Fauvel, Montpellier (FR); Cédric Bories, Montpellier (FR); Abdelaziz Yasri, Castelnau le Lez (FR)

(73) Assignee: ORIBASE PHARMA, Montpellier (FR)

( * ) Notice: Subject to any disclaimer, the term of this patent is extended or adjusted under 35 U.S.C. 154(b) by 0 days.

(21) Appl. No.: 14/655,609

(22) PCT Filed: Dec. 30, 2013

(86) PCT No.: PCT/EP2013/078139
§ 371 (c)(1),
(2) Date: Jun. 25, 2015

(87) PCT Pub. No.: WO2014/102377
PCT Pub. Date: Jul. 3, 2014

(65) Prior Publication Data
US 2015/0353539 A1  Dec. 10, 2015

Related U.S. Application Data

(60) Provisional application No. 61/747,075, filed on Dec. 28, 2012.

(30) Foreign Application Priority Data

Dec. 28, 2012 (FR) ...................... 12 62931

(51) Int. Cl.
| | |
|---|---|
| *C07D 401/02* | (2006.01) |
| *C07D 401/10* | (2006.01) |
| *A61K 31/437* | (2006.01) |
| *A61K 31/4353* | (2006.01) |
| *C07D 471/04* | (2006.01) |
| *G01N 33/574* | (2006.01) |

(52) U.S. Cl.
CPC ....... *C07D 471/04* (2013.01); *G01N 33/57484* (2013.01); *G01N 33/574* (2013.01); *G01N 2333/912* (2013.01); *G01N 2500/10* (2013.01); *G01N 2800/52* (2013.01)

(58) Field of Classification Search
CPC ... C07D 401/02; C07D 401/10; A61K 31/437; A61K 31/4353
USPC .......................................... 546/121; 514/300
See application file for complete search history.

(56) References Cited

FOREIGN PATENT DOCUMENTS

| WO | WO 2007/017143 A1 | 2/2007 |
|---|---|---|
| WO | WO 2008/028617 A1 | 3/2008 |
| WO | WO 2008/144253 A1 | 11/2008 |
| WO | WO 2009/012283 A1 | 1/2009 |
| WO | WO 2009/111278 A2 | 9/2009 |
| WO | 2010092489 | * 8/2010 |
| WO | WO 2010/092489 A1 | 8/2010 |

OTHER PUBLICATIONS

International Search Report issued in PCT/EP2013/078139, mailed on Feb. 26, 2015.
Brunton et al., "Src and focal adhesion kinase as therapeutic targets in cancer," Current Opinion in Pharmacology, vol. 8, 2008 (Available online Jul. 22, 2008), pp. 427-432.
Cébe-Suarez et al., "The role of VEGF receptors in angiogenesis; complex partnerships," Cellular and Molecular Life Sciences, vol. 63, 2006 (Online First Feb. 7, 2006), pp. 601-615.
Chico et al., "Targeting protein kinases in central nervous system disorders," Nature Reviews Drug Discovery, vol. 8, No. 11, Nov. 2009 (available in PMC Feb. 19, 2010), pp. 1-39.
Cook et al., "Angiogenesis Inhibitors—Current Strategies and Future Prospects," CA: A Cancer Journal for Clinicians, vol. 60, No. 4, 2010 (available in PMC Jul. 1, 2011), pp. 1-35.
Fox et al., "Angiogenesis: pathological, prognostic, and growth-factor pathways and their link to trial design and anticancer drugs," The Lancet Oncology, vol. 2, May 2001, pp. 278-289.
Hofmeister et al., "Anti-cancer therapies targeting the tumor stroma," Cancer Immunology, Immunotherapy, vol. 57, 2008 (Published online Jul. 27, 2007), pp. 1-17.
International Search Report (Form PCT/ISA/210) for International Application No. PCT/EP2013/078138, dated Feb. 26, 2014.
International Search Report (Form PCT/ISA/210) for International Application No. PCT/EP2013/078140, dated Feb. 26, 2014.
Khazak et al., "Selective Raf Inhibition in Cancer Therapy," Expert Opinion on Therapeutic Targets, vol. 11, No. 12, Dec. 2007 (available in PMC Aug. 3, 2009), pp. 1-35.
Kontzias et al., "Kinase inhibitors in the treatment of immune-mediated disease," F1000 Medicine Reports, vol. 4, No. 5, Mar. 1, 2012, pp. 1-8.

(Continued)

*Primary Examiner* — Niloofar Rahmani
(74) *Attorney, Agent, or Firm* — Birch, Stewart, Kolasch & Birch, LLP

(57) ABSTRACT

The present invention relates to compounds of the following formula (I) and/or the pharmaceutically acceptable addition salts, solvates, enantiomers, diastereoisomers thereof, as well as mixtures thereof. The subject matter of the present invention thus also includes the preparation of compounds of formula (I), their uses, in particular in the inhibition of protein kinases which are implicated for example in numerous diseases such as cancers or immune system disorders.

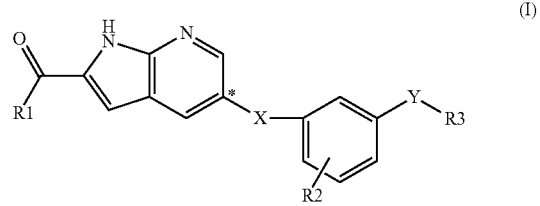

21 Claims, 6 Drawing Sheets

(56) References Cited

OTHER PUBLICATIONS

Mouaddib et al., "Synthesis of Indolo[3,2-c]quinoline and Pyrido[3',2':4,5][3,2-c]quinoline Derivatives," Synthesis, No. 4, 2000, pp. 549-556.

Pennell et al., "Combined Inhibition of the VEGFR and EGFR Signaling Pathways in the Treatment of NSCLC," The Oncologist, vol. 14, 2009 (first published online Apr. 8, 2009), pp. 399-411.

Potapova et al., "Contribution of individual targets to the antitumor efficacy of the multitargeted receptor tyrosine kinase inhibitor SU11248," Molecular Cancer Therapeutics, vol. 5, No. 5, May 2006, pp. 1280-1289.

Raman et al., "Role of chemokines in tumor growth," Cancer Letters, vol. 256, 2007, pp. 137-165.

Sun et al., "Antioxidative and thrombolytic TMP nitrone for treatment of ischemic stroke," Bioorganic and Medicinal Chemistry, vol. 16, No. 19, 2008 (Available online Aug. 31, 2008), pp. 8868-8874.

Wang et al., "Substituent Diversity-Directed Synthesis of Indole Derivatives," Journal of Combinatorial Chemistry, vol. 11, No. 4, 2009 (Published on Web May 26, 2009), pp. 556-575.

Yeatman, "A Renaissance for SRC," Nature Reviews Cancer, vol. 4, Jun. 2004, pp. 470-480.

\* cited by examiner

AZAINDOLE DERIVATIVES AS MULTI KINASE INHIBITORS

The present invention relates to compounds that are inhibitors of protein kinases, the method of preparation thereof and the therapeutic applications thereof.

Dysfunction/deregulation of protein kinases (PK) is the cause of a large number of pathologies including oncological, immunological, neurological, metabolic and infectious diseases. This has generated considerable interest in the development of small molecules and biological kinase inhibitors for the treatment of these disorders.

Numerous PK are particularly deregulated during the process of tumorigenesis. Consequently protein kinases are attractive targets for anticancer drugs, including small molecule inhibitors that usually act to block the binding of ATP or substrate to the catalytic domain of the tyrosine kinase and monoclonal antibodies that specifically target receptor tyrosine kinases (RTK) and their ligands. In solid malignancies, it is unusual for a single kinase abnormality to be the sole cause of disease and it is unlikely that tumors are dependent on only one abnormally activated signaling pathway. Instead multiple signaling pathways are dysregulated. Furthermore, even single molecular abnormalities may have multiple downstream effects. Multi targeted therapy using a single molecule (MTKI="Multi-Targeted Kinase Inhibitors") which targets several signaling pathways simultaneously, is more effective than single targeted therapy. Single targeted therapies have shown activity for only a few indications and most solid tumors show deregulation of multiple signaling pathways. For example, the combination of a vascular endothelial growth factor receptor (VEGFR) inhibitor and platelet derived growth factor receptor (PDGFR) inhibitor results in a cumulative antitumor efficacy (Potapova et al., Mol Cancer Ther 5, 1280-1289, 2006).

Tumors are not built up solely of tumor cells. An important part consists of connective tissue or stroma, made up of stromal cells and extracellular matrix, which is produced by these cells. Examples of stromal cells are fibroblasts, endothelial cells and macrophages. Stromal cells also play an important role in the carcinogenesis, where they are characterized by upregulation or induction of growth factors and their receptors, adhesion molecules, cytokines, chemokines and proteolytic enzymes (Hofmeister et al., Immunotherapy 57, 1-17, 2007; Raman et al., Cancer Letters 256, 137-165, 2007; Fox et al., The Lancet Oncology 2, 278-289, 2001)

The receptor associated tyrosine kinase VEGFR on endothelial and tumor cells play a central role in the promotion of cancer by their involvement in angiogenesis (Cébe-Suarez et al., Cell Mol Life Sci 63, 601-615, 2006). In addition, the growth factors TGF-β, PDGF and FGF2 secreted by cancer cells transform normal fibroblasts into tumor associated fibroblasts, which make their receptors a suitable target for inhibition by kinase inhibitors (Raman et al., 2007).

Moreover, increasing evidence suggests a link between the EGF receptor (EGFR) and HER2 pathways and VEGF-dependent angiogenesis and preclinical studies have shown both direct and indirect angiogenic effects of EGFR signaling (Pennell and Lynch, The Oncologist 14, 399-411, 2009). Upregulation of tumor pro-angiogenic factors and EGFR-independent tumor-induced angiogenesis have been suggested as a potential mechanism by which tumor cells might overcome EGFR inhibition. The major signaling pathways regulated by EGFR activation are the PI3K, MAPK and Stat pathways that lead to increased cell proliferation, angiogenesis, inhibition of apoptosis and cell cycle progression. EGFR is overexpressed in a wide variety of solid tumors, such as lung, breast, colorectal and cancers of the head and neck (Cook and Figg, C A Cancer J Clin 60, 222-243 2010). Furthermore, higher expression of EGFR has been shown to be associated with metastasis, decreased survival and poor prognosis.

c-Src, a membrane-associated non receptor tyrosine kinase, is involved in a number of important signal transduction pathways and has pleiotropic effects on cellular function. c-Src integrates and regulates signaling from multiple transmembrane receptor-associated tyrosine kinases, such as the EGFR, PDGFR, IGF1R, VEGFR, HER2. Together, these actions modulate cell survival, proliferation, differentiation, angiogenesis, cell motility, adhesion, and invasion (Brunton and Frame, Curr Opin Pharmacol 8, 427-432, 2008). Overexpression of the protein c-Src as well as the increase in its activity were observed in several types of cancers including colorectal, gastrointestinal (hepatic, pancreatic, gastric and oesophageal), breast, ovarian and lung (Yeatman, Nat Rev Cancer 4, 470-480, 2004).

The activation in EGFR or KRAS in cancers leads to a greatly enhanced level of Ras-dependent Raf activation. Hence, elimination of Raf function is predicted to be an effective treatment for the numerous cancers initiated with EGFR and KRAS lesions (Khazak et al., Expert Opin. Ther. Targets 11, 1587-1609, 2007). Besides activation of Raf signaling in tumors, a number of studies implicate the activation of the Ras-Raf-MAPK signaling pathway as a critical step in vasculogenesis and angiogenesis. Such activation is induced by growth factor receptors such as VEGFR2, FGFR2 and thus inhibition of Raf activation represents a legitimate target for modulation of tumor angiogenesis and vascularization.

Although VEGFR, PDGFR, EGFR, c-Src and Raf are important targets on both tumor cells and tumor stroma cells, other kinases such as FGFR only function in stromal cells and other oncogenes often only function in tumor cells.

Protein kinases are fundamental components of diverse signaling pathways, including immune cells. Their essential functions have made them effective therapeutic targets. Initially, the expectation was that a high degree of selectivity would be critical; however, with time, the use of "multikinase" inhibitors has expanded. Moreover, the spectrum of diseases in which kinase inhibitors are used has also expanded to include not only malignancies but also immune-mediated diseases/inflammatory diseases. The first step in signaling by multi-chain immune recognition receptors is mediated initially by Src family protein tyrosine kinases. MTKI targeting kinases involved in immune function are potential drugs for autoimmune diseases such as rheumatoid arthritis, psoriasis and inflammatory bowel diseases (Kontzias et al., F1000 Medicine Reports 4, 2012)

Protein kinases mentioned previously are also key components of many other physiological and pathological mechanisms such as neurodegeneration and neuroprotection (Chico et al., Nature Reviews Drug Discovery 8, 892-909, 2009), atherosclerosis, osteoporosis and bone resorption, macular degeneration, pathologic fibrosis, Cystogenesis (human autosomal dominant polycystic kidney disease . . . ).

In WO2010/092489 and related patents/patent applications, we identified several compounds which exhibited interesting properties for such applications. However, we have discovered that some of these compounds could be enhanced in their properties by selectively working on particular regions of their structures. However, the mechanism of action of these structures on kinases was not precisely elucidated at the time of WO2010/092489's filing and thus it was unexpectedly that we found the high activities of the structures disclosed in the present application.

The subject matter of the present invention is to offer novel multi-targeted kinase inhibitors, having an original backbone, which can be used therapeutically in the treatment of pathologies associated with deregulation of protein kinases including tumorigenesis, human immune disorders, inflammatory diseases, thrombotic diseases, neurodegenerative diseases, bone diseases, macular degeneration, fibrosis, cystogenesis.

The inhibitors of the present invention can be used in particular for the treatment of numerous cancers and more particularly in the case of liquid tumors such hematological cancers (leukemias) or solid tumors including but not limited to squamous cell cancer, small-cell lung cancer, non-small cell lung cancer, gastric cancer, pancreatic cancer, glial cell tumors such as glioblastoma and neurofibromatosis, cervical cancer, ovarian cancer, liver cancer, bladder cancer, breast cancer, melanoma, colorectal cancer, endometrial carcinoma, salivary gland carcinoma, renal cancer, prostate cancer, vulval cancer, thyroid cancer, sarcomas, astrocytomas, and various types of hyperproliferative diseases.

SUMMARY OF THE INVENTION

The present invention relates to compounds of the following formula (I):

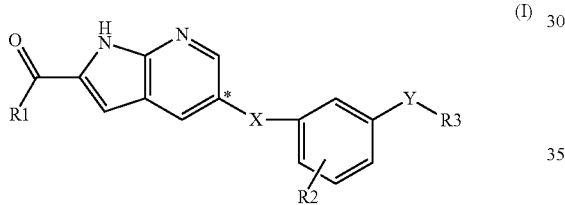

R1 is a $C_1$-$C_6$ alkyl group, a —NR4R5 group, or an —OR6 group,
R4, R5 and R6 are independently a hydrogen atom, and/or $C_1$-$C_6$ alkyl group,
X is chosen from a group consisting of:
  —C*(R7R8)-N(R9)-C(R10R11)-,
  —C*(R7R8)-N(R9)-C(O)—,
  —C*(R7R8)N(R9)-,
  —C*(R7R8)O—,
  —O*C(R7R8)-,
  —C*(R7R8)S—,
  —S*C(R7R8)-,
  —C*(R7R8)C(R9R10)-,
  —C*(O)NH—,
  —C*(S)NH—,
  —C*(R7)=C(R8)-,
  —C*(R7)=N—, and
  —N*(R7)-C(R8R9)-C(R10R11)-
    wherein R7, R8, R9, R10 and R11 are independently a hydrogen atom, and/or $C_1$-$C_6$ alkyl, and the atoms labeled with a "*" are linked to the carbon labeled with a "*" in formula (I), preferably R7, R8, R9, R10 and R11 are all hydrogen atoms,
R2 is a hydrogen atom, a $C_1$-$C_6$ alkyl group or a halogen atom,
Y is chosen from a group consisting of HNC(O), HNC(S), $HNSO_2$, $HNC(O)CH_2$, $HNC(S)CH_2$, HNC(O)NH, HNC(S)NH, $CH_2NHC(O)$, C(O)NH, $CH_2NHC(S)$ and $C(O)NHCH_2$, and R3 is chosen from a group consisting of:
  an aryl, preferably a phenyl group mono or polysubstituted with:
    a hydroxyl,
    a halogen,
    a $C_1$-$C_6$ alkyl-amine, preferably a secondary $C_1$-$C_6$ alkyl-amine,
    a $C_1$-$C_6$ alkoxy,
    an amine substituted by a heteroaryl such as thiazol, or imidazol said heteroaryl optionally monosubstituted by a methyl- a $C_1$-$C_6$ trifluoroalkoxy, preferably a trifluoromethoxy,
    a $C_1$-$C_6$ alkyl, preferably a methyl, isopropyl,
    a $C_1$-$C_6$ trifluoroalkyl, preferably a trifluoromethyl,
    a heteroaryl group such as thiazol, or imidazol optionally monosubstitued by a methyl,
    an aliphatic heterocycle, optionally substituted by a methyl group, a hydroxyl group, an amine group, —$NHCH_3$, or —$N(CH_3)_2$,
    a $C_1$-$C_6$ alkyl substituted by a heterocycle, wherein said heterocycle is optionally substituted by a methyl group, a hydroxyl group, an amine group, —$NHCH_3$, or —$N(CH_3)_2$, and/or
    the fragment:

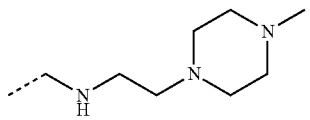

a heteroaryl group preferably chosen from a group consisting of dihydrobenzofuran, indol, benzodioxol, benzotriazol, pyridine optionally substituted with a $C_1$-$C_6$ alkyl, a $C_1$-$C_6$ trifluoroalkyl, a halogen and/or a hydroxyl, and
  non aromatic monosubstituted cyclic group, preferably a cyclic $C_3$-$C_{10}$ alkyl, monosubstituted with a hydroxyl, a halogen, a $C_1$-$C_6$ alkyl-amine, a $C_1$-$C_6$ alkoxy, a $C_1$-$C_6$ trifluoroalkoxy, a $C_1$-$C_6$ alkyl, a $C_1$-$C_6$ trifluoroalkyl,
and/or the pharmaceutically acceptable addition salts, solvates, Z or E isomers, enantiomers, diastereoisomers thereof, as well as mixtures thereof.

Another aspect of the present invention concerns a method of preparation of the compounds as defined herein, characterized in that it comprises at least one of the following steps for the formation of the X group:
  a) a reductive amination,
  b) a Wittig reaction, with an optional reduction of the double bond,
  c) a coupling reaction done in peptide coupling conditions,
  d) a Mitsunobu reaction,
  e) a reduction,
preferably, the X group is formed through a Wittig reaction.

Another aspect of the present invention concerns a method of preparation of the compounds as defined herein, characterized in that it comprises at least one of the following steps for the formation of the X group:
  a) a reductive amination,
  b) a Wittig reaction, with an optional reduction of the double bond,
  c) a coupling reaction done in peptide coupling conditions, d) a Mitsunobu reaction,
e) a reduction,
f) an hydrolysis,
g) a brome substitution, or
h) a condensation step,
preferably, the X group is formed through a Wittig reaction optionally followed by a reduction of the double bond.

Another aspect of the present invention concerns a method of preparation of the compounds as defined herein, characterized in that the method comprises at least one of the following steps, preferably after steps (a), (b), (c), (d) and/or (e) of the above method:
- $f_1$) formation of a urea in the case of Y being HNC(O)NH, by reaction with an isocyanate,
- $f_2$) formation of a thiourea in the case of Y being HNC(S)NH, by reaction with an isothiocyanate,
- $f_3$) formation of a sulfamide in the case of Y being $HNSO_2$, by reaction with a halogen sulfamyl or halogene sulfonyl, such as sulfamyl chloride or sulfonyl chloride,
- $f_4$) formation of an amide in the case of Y being HNCO, by reaction with an activated carboxylic acid, such as an acyl chloride
- $f_5$) formation of a thioamide in the case of Y being HNCS by reacting the compound obtained after step f4) with the Lawesson's reagent
- $f_6$) a coupling reaction done in peptide coupling conditions.

Another aspect of the present invention concerns a method of preparation of the compounds as defined herein, characterized in that the method comprises at least one of the following steps, preferably after steps (a), (b), (c), (d), (e), (f), (g) or (h) of the above method:
- $i_1$) formation of a urea in the case of Y being HNC(O)NH, by reaction with an isocyanate,
- $i_2$) formation of a thiourea in the case of Y being HNC(S)NH, by reaction with an isothiocyanate,
- $i_3$) formation of a sulfonamide in the case of Y being $HNSO_2$, by reaction with a halogen sulfamyl or halogene sulfonyl, such as sulfamyl chloride or sulfonyl chloride,
- $i_4$) formation of an amide in the case of Y being HNCO or $HNC(O)CH_2$, by reaction with an activated carboxylic acid using peptide coupling techniques, or an acyl chloride, or
- $i_5$) formation of a thioamide in the case of Y being HNCS or $HNC(S)CH_2$, by reacting the compound obtained after step i4) with the Lawesson's reagent.
- $i_6$) a coupling reaction done in peptide coupling conditions.

Another aspect of the present invention concerns a method of preparation of the compounds as defined herein, characterized in that the method comprises at least one of the following steps, preferably after steps ((a), (b), (c), (d), (e), (f), (g) or (h) of the above method:
- $i_1$) formation of a urea in the case of Y being HNC(O)NH, by reaction with an isocyanate,
- $i_2$) formation of a thiourea in the case of Y being HNC(S)NH, by reaction with an isothiocyanate,
- $i_3$) formation of a sulfonamide in the case of Y being $HNSO_2$, by reaction with a halogen sulfonyl, such as sulfonyl chloride,
- $i_4$) formation of an amide in the case of Y being HNCO, by reaction with an activated carboxylic acid, such as an acyl chloride,
- $i_5$) formation of a thioamide in the case of Y being HNCS, by reacting the compound obtained after step f4) with the Lawesson's reagent, or
- $i_6$) a coupling reaction done in peptide coupling conditions, and
- j) optional saponification of the obtained product, preferably by the use of KOH.

Another aspect of the present invention concerns a method of preparation of the compounds as defined herein, characterized in that the method comprises optionally after steps (j) of the above method:
- k) an optional coupling reaction of the obtained product performed in peptide coupling conditions.

Yet the present invention also relates to a compound as defined herein characterized in that it is a drug.

The present invention also relates to a compound as defined herein used as inhibitor of protein kinases in diseases such as tumorigenesis, human immune disorders, inflammatory diseases, thrombotic diseases, neurodegenerative diseases, bone diseases, macular degeneration, fibrosis, cystogenesis, hyperproliferative diseases, cancers, more particularly liquid tumors such as hematological cancers such as leukemias, chronic or acute myeloproliferative disorders or solid tumors such as squamous cell cancer, small-cell lung cancer, non-small cell lung cancer, gastrointestinal cancers, pancreatic cancer, glial cell tumors such as glioblastoma and neurofibromatosis, cervical cancer, ovarian cancer, liver cancer, bladder cancer, breast cancer, melanoma, colorectal cancer, endometrial carcinoma, salivary gland carcinoma, kidney cancer, renal cancer, prostate cancer, vulval cancer, thyroid cancer, sarcomas and/or astrocytomas.

Pharmaceutical composition, characterized in that it contains, as active principle, a compound as defined herein and a pharmaceutical acceptable excipient.

DEFINITIONS

In general, the following definitions are used:

The expression "peptide coupling" in the present invention means the reaction which enables to form an amide —NH—C(O)—. However the techniques used in this reaction are common in peptide syntheses, i.e. by activating a carboxylic acid in order to enable an amine to react onto it. Therefore, although no peptide is formed in the present invention, the coupling reactions are derived from peptide synthesis, and directly applicable to the subject matter of the present invention.

The coupling reactions may be carried out by employing a condensing reagent such as N,N'-dicyclohexylcarbodiimide (DCC) or 1-ethyl-3-(3'-dimethylaminopropyl)carbodiimide hydrochloride (EDC), i.e. water-soluble carbodiimide, O-(1H-benzotriazol-1-yl)-N,N,N',N'-tetramethyluronium tetrafluoroborate (TBTU), benzotriazol-1-yl-oxytris(dimethylamino)phosphonium hexafluorophosphate (BOP), O-(7-azabenzotriazol-1-yl)-1,2,3-tetramethyluronium hexafluorophosphate (HATU), O-benzotriazol-1-yl-N,N,N',N'-tetramethyluronium hexafluorophosphate (HBTU), O-benzotriazol-1-yl -tetramethyltetrafluoroborate (TBTU), N-hydroxy-5-norbornene-2,3-dicarbodiimide, or any other coupling agent in a solvent such as ether, acetone, chloroform, dichloromethane, ethyl acetate, DMF, tetrahydrofuran (THF), acetonitrile, dimethylsulfoxide (DMSO), N-methyl pyrrolidinone (NMP), under ice-cooling or at room temperature, preferably in the presence of an acylation catalyst such as dimethylaminopyridine (DMAP), pyridine, N-hydroxybenzotriazole (HOBt), 1-hydroxy-7-azabenzotriazole (HOAt), N-hydroxysuccinimide and the like.

The term C(O) is equivalent to C=O.

The rem C(S) is equivalent to C=S.

The expression "alkyl group" in the present invention means a linear or branched saturated aliphatic group with 1 to 6 carbon atoms, if it is not specified. Examples of alkyl groups covered by the scope of the present invention are methyl, ethyl, propyl, butyl, tert-butyl, isopropyl groups, etc.

The expression "cycloalkyl group" in the present invention means a cyclic alkyl group with 3 to 10 carbon atoms. Examples of alkyl groups covered by the scope of the present invention are cyclopropyl, cyclobutyl, cyclopentyl, cyclohexyl, methylcyclohexyl, etc.

The expression "aryl group" in the present invention means a cyclic (mono- or polycyclic) aromatic group comprising between 2 and 10 carbon atoms. Examples of aryl groups covered by the scope of the present invention are phenyl, naphthyl, etc.

The expression "heteroaryl group" in the present invention means a cyclic (mono- or polycyclic) aromatic group comprising between 2 and 10 carbon atoms and between 1 and 3 heteroatoms, such as nitrogen, oxygen or sulphur. Examples of heteroaryl groups covered by the scope of the present invention are pyridine, thiophene, thiazole, imidazole, pyrazole, pyrrole, quinoline, indol, pyridazine, quinoxaline, dihydrobenzofuran, benzodioxol, benzotriazol, preferably chosen from a group consisting of dihydrobenzofuran, indol, benzodioxol, benzotriazol, pyridine. Optionally the heteroaryl group, and in particular one of the preferred heteroaryl groups, is substituted with a $C_1$-$C_6$ alkyl group, a $C_1$-$C_6$ trifluoroalkyl group, a halogen atom and/or a hydroxyl.

The expression "non aromatic monosubstituted cyclic group" in the present invention means non aromatic monosubstituted heterocyclic groups.

The expression "heterocyclic group" in the present invention means a cyclic group comprising between 2 and 10 carbon atoms and between 1 and 3 heteroatoms, such as nitrogen, oxygen and sulphur. The heterocycles can be saturated, i.e. aliphatic, non-saturated, or even aromatic. Examples of heterocyclic groups covered by the scope of the present invention are piperazinyl, morpholyl, tetrahydrofuranyl, pyridyl, thiazyl, imidazyl, pyrazyl, quinoxaline, dihydrobenzofuranyl, pyrryl, pyridazinyl, benzimidazyl, pyrimidinyl, 1H-pyrrolo[2,3-b]pyridyl, etc.

The expression "aliphatic heterocycle" means in the present invention aliphatic cyclic group which comprise one or several heteroatoms, such as morpholine, piperidine, piperazine, pyrrolidine.

The expression "halogen atom" in the present invention means: fluorine, chlorine, bromine or iodine atoms.

The expression "alkoxy group" in the present invention means an alkyl group bound to an oxygen. Examples of alkoxy groups covered by the scope of the present invention are methoxy, ethoxy groups etc.

The expression "aryloxy group" in the present invention means an aryl group bound to an oxygen atom. Examples of aryloxy groups covered by the scope of the present invention are phenyloxy, etc.

The expression "sulphonamide group" in the present invention means:

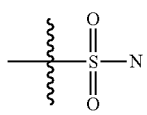

The expression "N-methyl sulphonamide group" in the present invention means:

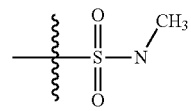

The expression "methanesulphonamide group" in the present invention means:

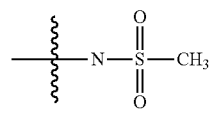 [SMILES: *NS(C)(=O)=O]

The expression "aralkyl group" in the present invention means an alkyl group substituted with an aryl group:

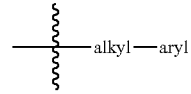

The expression "$C_1$-$C_6$ alkyl amine group" or "$C_1$-$C_6$ alkyl amine group" in the present invention means a $C_1$-$C_6$ alkyl group substituted with an amine group:

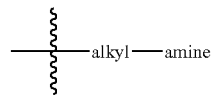

The expression "secondary $C_1$-$C_6$ alkyl amine group" means a secondary amine, i.e. which can be substituted by two $C_1$-$C_6$ alkyl groups.

The expression "hydroxyl group" in the present invention means: OH

The expression "alkoxyalkyl group" in the present invention means an alkyl group, preferably a substituted with an alkoxy group:

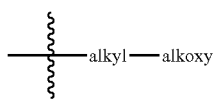

The expression "sulphanyl group" in the present invention means:

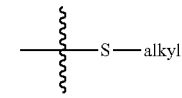

The expression "ureido" in the present invention is used as a general term for a urea or thiourea.

The expression "substituted phenyl" in the present invention means a phenyl mono- or poly-substituted with:

a halogen atom, a nitro group —(NO$_2$), a cyano group (CN), a methylthiazyl group,

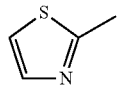

an alkoxy group, an aryloxy group, an alkyl group, a sulphonamide group, an N-methyl sulphonamide group, a methanesulphonamide group, a heteroaryl group, a hydroxyl group, a tertiary amine group, a group —CONHalkyl, a group —NHCOalkyl.

The term "pyridyl" means a radical derived from pyridine:

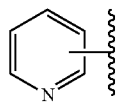

The term "thiophenyl" in the present invention means a radical derived from thiophene:

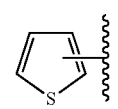

The term " thiazyl" in the present invention means a radical derived from thiazole:

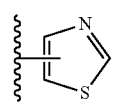

The term "imidazyl" in the present invention means a radical derived from imidazole:

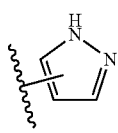

The term "pyrazyl" in the present invention means a radical derived from pyrazole:

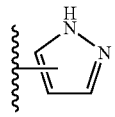

The term "quinoxaline" in the present invention means:

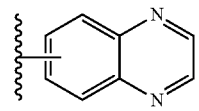

The term "dihydrobenzofuranyl" in the present invention means radical derived from dihydrobenzofuran:

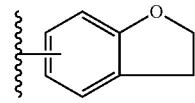

The term "pyrryl" in the present invention means radical derived from pyrrole:

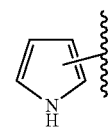

The term "indyl" in the present invention means a radical derived from indole:

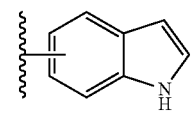

The term "pyridazinyl" in the present invention means radical derived from pyridazine:

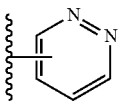

The term "N-morpholyl" in the present invention means radical derived from morpholine:

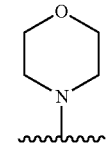 [SMILES: *N1CCOCC1]

The term "benzimidazyl" in the present invention means radical derived from benzimidazole:

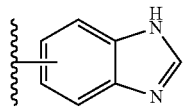

The term "pyrimidinyl" in the present invention means radical derived from pyrimidine:

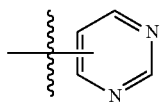

The expression "1H-pyrrolo[2,3-b]pyridyl" in the present invention means a radical derived from 1H-pyrrolo[2,3-b]pyridine:

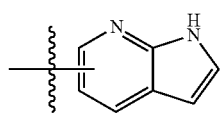

The expression "pharmaceutical composition" in the present invention means any composition comprising an effective dose of a compound of the invention and at least one pharmaceutically acceptable excipient. Said excipients are selected, depending on the pharmaceutical form and the desired method of administration, from the usual excipients known by a person skilled in the art.

The expression "pharmaceutically acceptable addition salts" in the present invention means all the pharmaceutically acceptable salts of the compounds according to the invention are included within the scope of the invention, in particular the salts of weak acids and of weak bases, for example the hydrochloride salt, hydrobromide salt, trifluoacetate salt etc.

The expression "mixtures of enantiomers" in the present invention means any mixture of enantiomers. The mixtures can be racemic, i.e. 50/50% of each enantiomer in weight (w/w), or non-racemic, i.e. enriched in one or the other of the enantiomer so that the ratios w/w are between 50/50% and 75/25%, between 75/25% and 90/10% or above 95% of one enantiomer in comparison with the other.

The expression "mixtures of diastereoisomers" in the present invention means any mixture of diastereoisomers in any proportions.

The expression "treatment" is intended to be directed towards all types of animals, preferably mammals, more preferably humans. In the case of a treatment of an animal which is not human kind, it will be referred to a veterinary treatment.

DETAILED DESCRIPTION OF THE PREFERRED EMBODIMENTS

Products

The present invention preferably relates to compounds of the following formula (I):

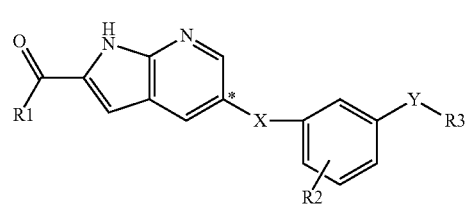

R1 is a $C_1$-$C_6$ alkyl group, a —NR4R5 group, or an —OR6 group,
R4, R5 and R6 are independently a hydrogen atom, and/or $C_1$-$C_6$ alkyl group,
X is chosen from a group consisting of:
—C*(R7R8)-N(R9)-C(R10R11)-,
—C*(R7R8)-N(R9)-C(O)—,
—C*(R7R8)N(R9)-,
—C*(R7R8)O—,
—O*C(R7R8)-,
—C*(R7R8)S—,
—S*C(R7R8)-,
—C*(R7R8)C(R9R10)-,
—C*(O)NH—,
—C*(S)NH—,
—C*(R7)=C(R8)-,
—C*(R7)=N—, and
—N*(R7)-C(R8R9)-C(R10R11)-
wherein R7, R8, R9, R10 and R11 are independently a hydrogen atom, and/or $C_1$-$C_6$ alkyl, and the atoms labeled with a "*" are linked to the carbon labeled with a "*" in formula (I), preferably R7, R8, R9, R10 and R11 are all hydrogen atoms,
R2 is a hydrogen atom, a $C_1$-$C_6$ alkyl group or a halogen atom,
Y is chosen from a group consisting of HNC(O), HNC(S), $HNSO_2$, $HNC(O)CH_2$, $HNC(S)CH_2$, HNC(O)NH, HNC(S)NH, $CH_2NHC(O)$, C(O)NH, $CH_2NHC(S)$ and $C(O)NHCH_2$, and
R3 is chosen from a group consisting of:
an aryl, preferably a phenyl group mono or polysubstituted with:
a hydroxyl group,
a halogen atom,
a $C_1$-$C_6$ alkyl-amine group, preferably a secondary $C_1$-$C_6$ alkyl-amine,
a $C_1$-$C_6$ alkoxy group,
a $C_1$-$C_6$ trifluoroalkoxy group, preferably a trifluoromethoxy,
a $C_1$-$C_6$ alkyl group, preferably a methyl or isopropyl,
a $C_1$-$C_6$ trifluoroalkyl group, preferably a trifluoromethyl, and/or
a heteroaryl group such as thiazol, or imidazol optionally monosubstituted by a methyl,
a heteroaryl group preferably chosen from a group consisting of dihydrobenzofuran, indol, benzodioxol, benzotriazol, pyridine optionally substituted with a $C_1$-$C_6$ alkyl group, a $C_1$-$C_6$ trifluoroalkyl group, a halogen atom and/or a hydroxyl, a non-aromatic monosubstituted cyclic group, preferably a cyclic $C_3$-$C_{10}$ alkyl, monosubstituted with a hydroxyl, a halogen, a $C_1$-$C_6$ alkyl-amine, a $C_1$-$C_6$ alkoxy, a $C_1$-$C_6$ trifluoroalkoxy, a $C_1$-$C_6$ alkyl, and/or a $C_1$-$C_6$ trifluoroalkyl, and a fragment chosen from a group consisting of:

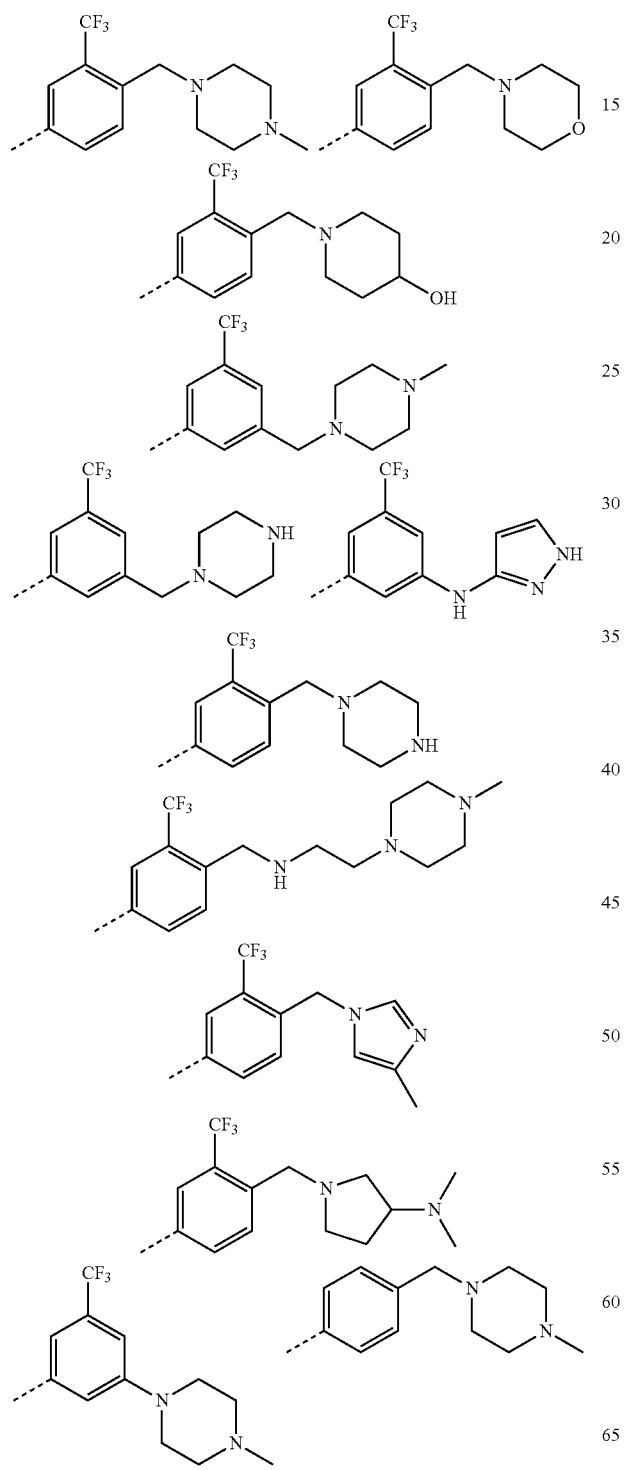

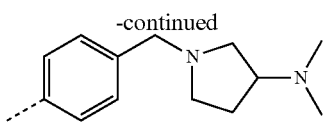

-continued and/or the pharmaceutically acceptable addition salts, solvates, enantiomers, diastereoisomers thereof, as well as mixtures thereof.

Advantageously, the compound (I) of the present invention is characterized in that:
R1 is a $C_1$-$C_6$ alkyl group, a —NR4R5 group, or an —OR6 group,
R4, R5 and R6 are independently a hydrogen atom, and/or $C_1$-$C_6$ alkyl group,
X is chosen from a group consisting of:
—C*(R7R8)-N(R9)-C(R1OR11)-,
—C*(R7R8)-N(R9)-C(O)—,
—C*(R7R8)N(R9)-,
—C*(R7R8)O—,
—O*C(R7R8)-,
—C*(R7R8)S—,
—S*C(R7R8)-,
—C*(R7R8)C(R9R10)-,
—C*(O)NH—,
—C*(S)NH—,
—C*(R7)=C(R8)-,
—C*(R7)=N—, and
—N*(R7)-C(R8R9)-C(R10R11)-
wherein R7, R8, R9, R10 and R11 are independently a hydrogen atom, and/or $C_1$-$C_6$ alkyl, and the atoms labeled with a "*" are linked to the carbon labeled with a "*" in formula (I), preferably R7, R8, R9, R10 and R11 are all hydrogen atoms,
R2 is a hydrogen atom, a methyl group or a halogene atom, such as fluorine or chlorine,
Y is chosen from the group consisting in HNC(O), HNC(S), $HNSO_2$, $HNC(O)CH_2$, HNC(O)NH, HNC(S)NH, C(O)NH, $C(O)NHCH_2$, $CH_2NHC(O)$ and $CH_2NHC(S)$, and
R3 is chosen from a group consisting of:
a phenyl group mono or polysubstituted with:
a hydroxyl group,
a halogen atom,
a $C_1$-$C_6$ alkyl-amine, preferably a secondary $C_1$-$C_6$ alkyl-amine,
a $C_1$-$C_6$ alkoxy,
a $C_1$-$C_6$ trifluoroalkoxy, preferably a trifluoromethoxy,
a $C_1$-$C_6$ alkyl, preferably a methyl, isopropyl,
a $C_1$-$C_6$ trifluoroalkyl, preferably a trifluoromethyl, and/or
a heteroaryl group, preferably chosen from a group consisting of thiazol, imidazol optionally monosubstitued by a $CF_3$ or a methyl,
a heteroaryl group chosen from a group consisting of dihydrobenzofuran, indol, benzodioxol, benzotriazol, pyridine, optionally substituted with a $C_1$-$C_6$ alkyl, a $C_1$-$C_6$ trifluoroalkyl, a halogen and/or a hydroxyl,
non aromatic monosubstituted cyclic group, preferably a cyclic $C_3$-$C_{10}$ alkyl, monosubstituted with a hydroxyl, a halogen, a $C_1$-$C_6$ alkyl-amine, a $C_1$-$C_6$ alkoxy, a $C_1$-$C_6$ trifluoroalkoxy, a $C_1$-$C_6$ alkyl, and/or a $C_1$-$C_6$ trifluoroalkyl, and a fragment is chosen from a group consisting of:

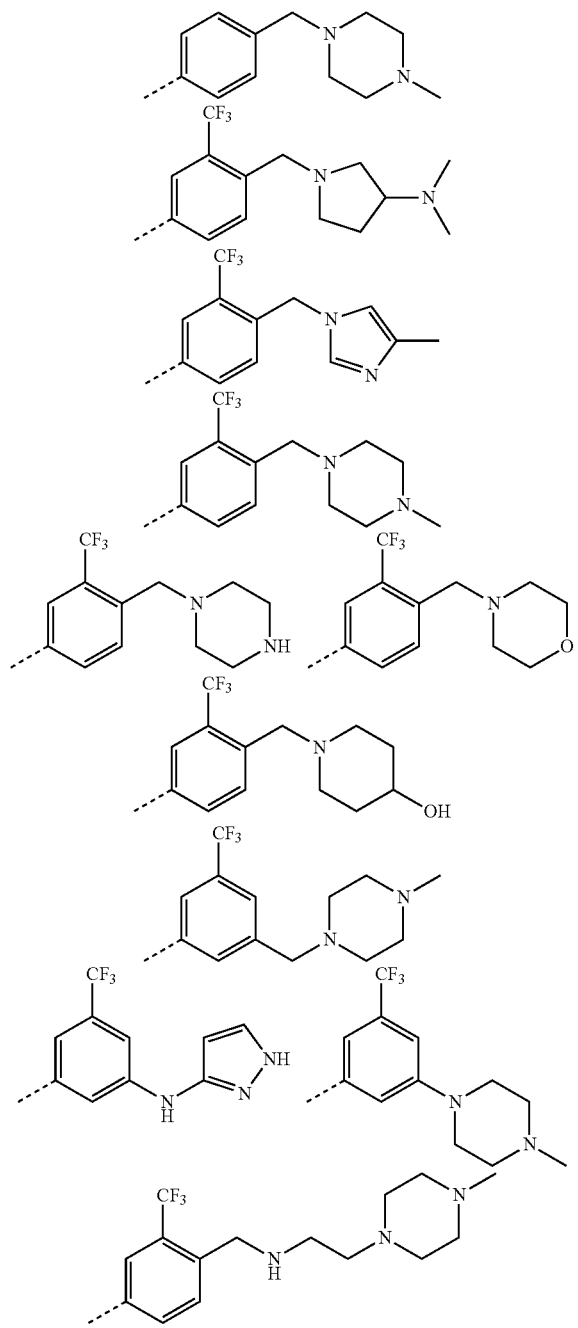

and/or the pharmaceutically acceptable addition salts, solvates, enantiomers, diastereoisomers thereof, as well as mixtures thereof.

Advantageously, the compound (I) of the present invention is characterized in that:

X is chosen from a group consisting of:
—CH$_2$—CH$_2$,
—CH═CH—,
—CH$_2$—O—,
—CH$_2$—NH—, and
—CO—NH—, R2 is an alkyl group, preferably a methyl group, or a halogen atom preferably a fluoride or chloride atom, R1, R3 and Y are as defined above.

More advantageously, the compound (I) of the present invention is characterized in that:

R1 is a hydroxyl group, a methyl group, a methoxy group or —NHMe group,

R2 is a methyl or a chlorine atom,

Y is HNC(O), HNC(O)CH$_2$, HNC(O)NH, HNC(S)NH, C(O)NH, C(O)NHCH$_2$, or CH$_2$NHC(O), preferably HNC(O), and R3 is chosen from a group consisting of:
a phenyl group mono substituted with a C$_1$-C$_6$ trifluoroalkyl group, a C$_1$-C$_6$ trifluoroalkoxy group, a C$_1$-C$_6$ alkyl group, a halogen, a non aromatic monosubstituted cyclic group, or a thiazol group optionally monosubstitued by a CF$_3$ and/or a methyl group, a phenyl group polysubstituted with a C$_1$-C$_6$ trifluoroalkyl, a C$_1$-C$_6$ alkyl-amine, a halogen, a non-aromatic monosubstituted cyclic group, a hydroxyl group and/or a thiazol group optionally monosubstitued by a CF$_3$ and/or a methyl group, a pyridine group, optionally substituted with a C$_1$-C$_6$ alkyl or a C$_1$-C$_6$ trifluoroalkyl, preferably methyl and/or a trifluoromethyl, a non-aromatic cyclic group chosen between a cyclic C$_3$-C$_{10}$ alkyl, monosubstituted with a C$_1$-C$_6$ alkyl and/or a C$_1$-C$_6$ trifluoroalkyl, and a fragment chosen from a group consisting of:

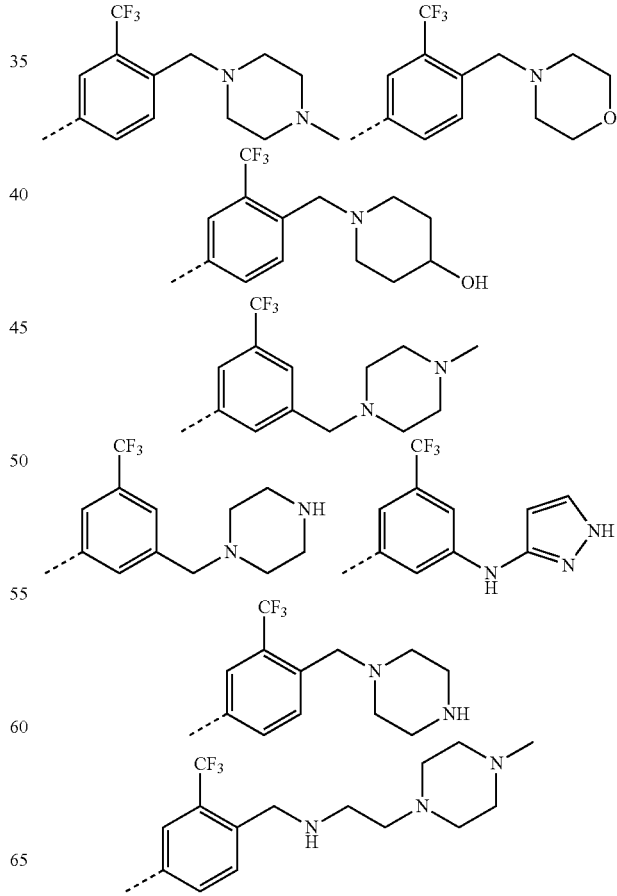

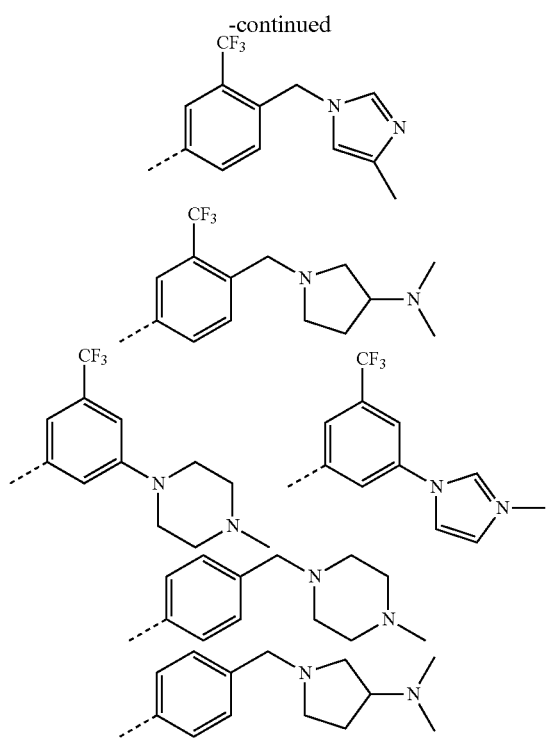

and X is as defined above.

Even more advantageously, the compound (I) is characterized in that:
R1 is a methyl group or methoxy group,
R2 is a methyl group,
X is —CH$_2$—CH$_2$—,
—CH=CH—,
—CH$_2$—O—, or
—CH$_2$—NH—
Y is HNC*(O), wherein C* is linked to R3 and
R3 is chosen from a group consisting of:

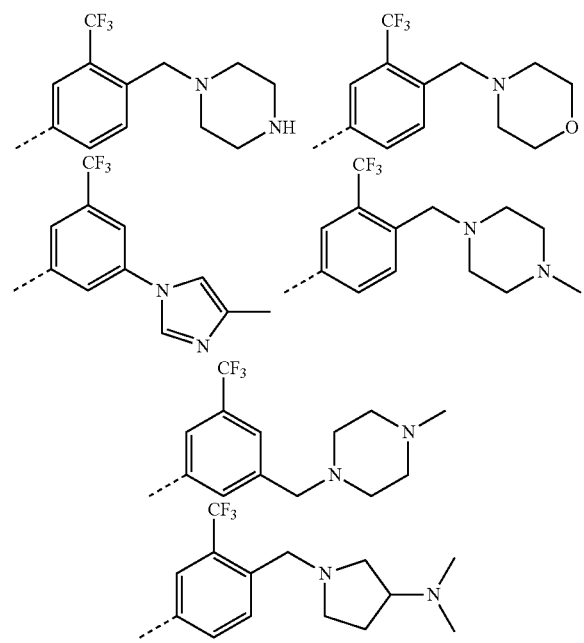

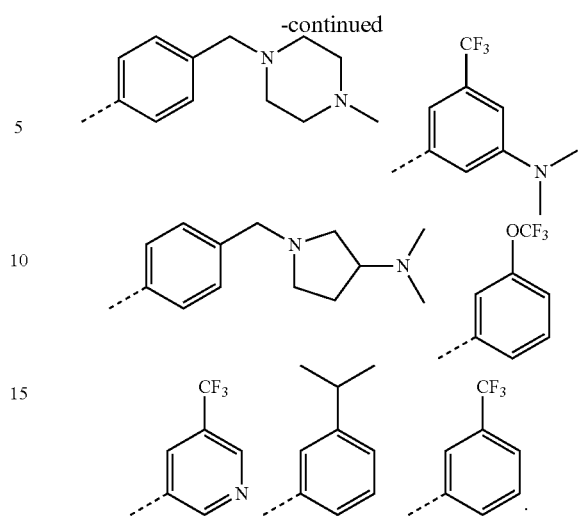

According to a preferred embodiment of the invention, the compound of formula (II):

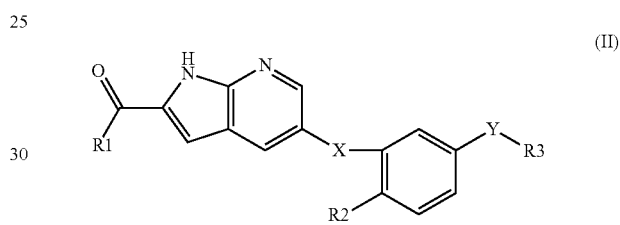

(II)

wherein R1, X, R2, Y and R3 are as defined above, preferably R3 is chosen from a group consisting of:

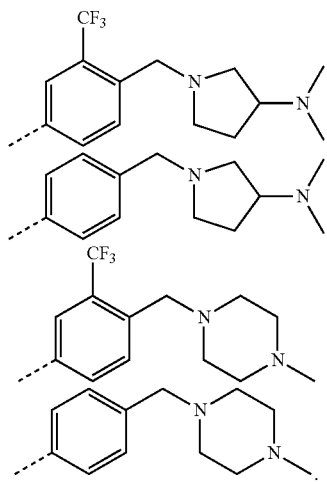

Advantageously, the compound of formula (II) is characterized in that:
R1 is a methyl group or methoxy group,
R2 is a methyl group,
X is —CH$_2$—CH$_2$—,
—CH=CH—,
—CH$_2$—O—, or
—CH$_2$—NH—
Y is HNC*(O), wherein C* is linked to R3 and R3 is chosen from a group consisting of:

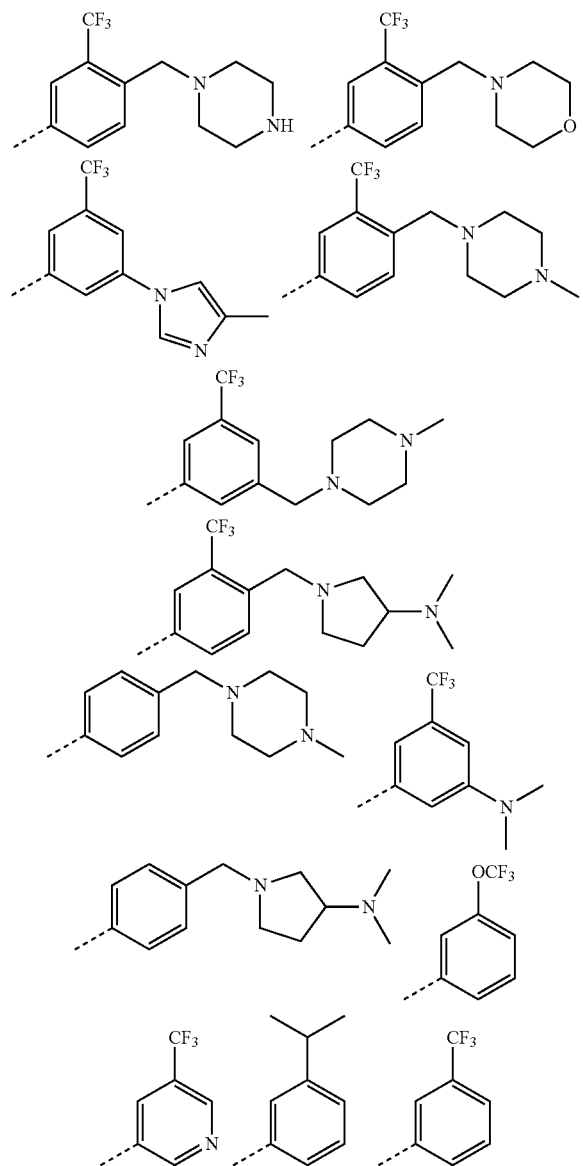

preferably R3 is chosen from a group consisting of:

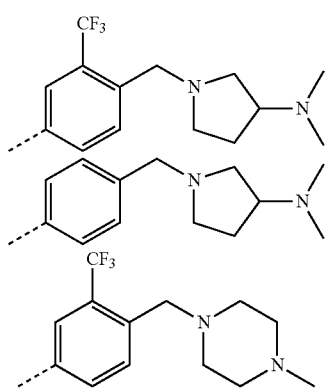

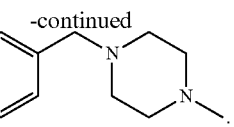

In another embodiment of the present invention, the compound (II) of the present invention is characterized in that:

R1 is a methyl group or methoxy group,
R2 is a methyl group,
X is —CH$_2$—CH$_2$—,
—CH=CH—,
—CH$_2$—O—, or
—CH$_2$—NH—
Y is HNC*(O), wherein C* is linked to R3 and
R3 is chosen from a group consisting of:

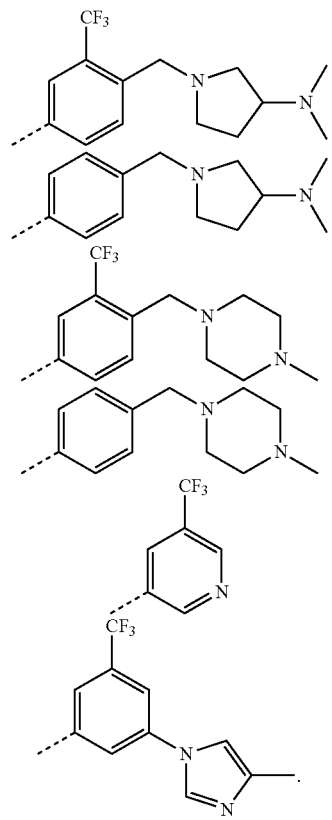

In a preferred embodiment of the present invention, the compound (II) of the present invention is characterized in that:

R1 is a methyl group or methoxy group,
R2 is a methyl group,
X is —CH$_2$—CH$_2$—,
—CH=CH—,
—CH$_2$—O—, or
—CH$_2$—NH—
Y is HNC*(O), wherein C* is linked to R3 and R3 is chosen from a group consisting of:

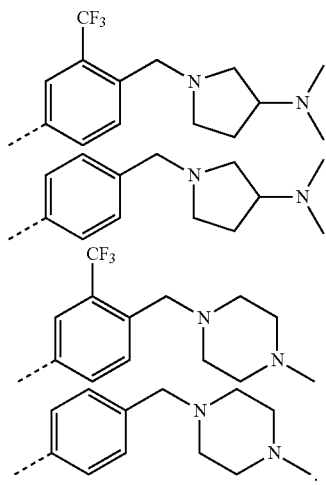

In a preferred embodiment of the present invention, the compound (II) of the present invention is characterized in that:
R1 is a methyl group or methoxy group,
R2 is a methyl group,
X is —CH$_2$—CH$_2$—,
  —CH=CH—,
  —CH$_2$—O—, or
  —CH$_2$—NH—,
Y is HNC*(O), wherein C* is linked to R3 and
R3 is chosen from a group consisting of:

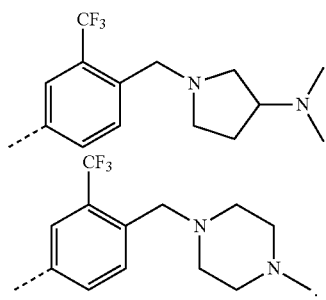

In another embodiment of the present invention, all the specific embodiments detailed above can also be characterized in that:
R1 is methyl or methoxy,
X is —CH$_2$—CH$_2$—,
  —CH=CH—, or
  —CH$_2$—O— and
R3 is preferably chosen from a group consisting of

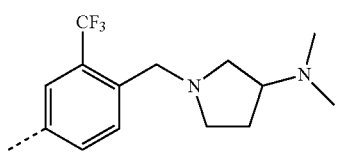

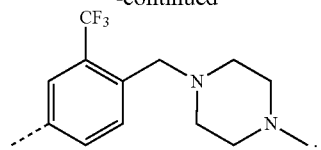

In a preferred embodiment of the present invention, the compound (II) of the present invention is characterized in that:
R1 is a methyl group or methoxy group,
R2 is a methyl group,
X is —CH$_2$—CH$_2$—, or
  —CH=CH—,
Y is HNC*(O), wherein C* is linked to R3 and
R3 is chosen from a group consisting of:

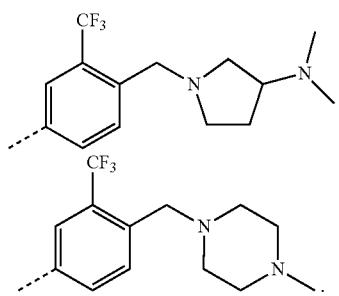

In a preferred embodiment of the present invention, the compound (II) of the present invention is characterized in that:
R1 is a methyl group,
R2 is a methyl group,
X is —CH$_2$—CH$_2$—, or
  —CH=CH—,
Y is HNC*(O), wherein C* is linked to R3 and
R3 is chosen from a group consisting of:

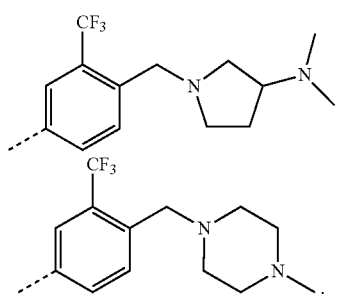

In a preferred embodiment of the present invention, the compound (II) of the present invention is characterized in that:
R1 is a methyl group or methoxy group,
R2 is a methyl group,
X is —CH$_2$—CH$_2$—,
Y is HNC*(O), wherein C* is linked to R3 and R3 is chosen from a group consisting of:

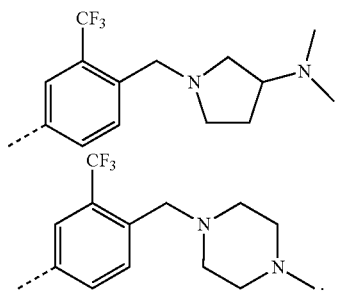

In a preferred embodiment of the present invention, the compound (II) of the present invention is characterized in that:
R1 is a methyl group,
R2 is a methyl group,
X is —CH₂—CH₂—,
Y is HNC*(O), wherein C* is linked to R3 and
R3 is chosen from a group consisting of:

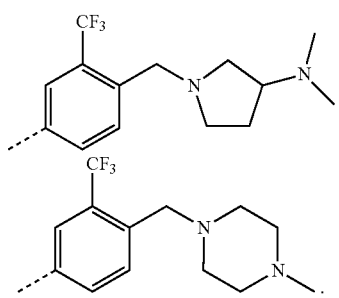

In a preferred embodiment of the present invention, the compound (II) of the present invention is characterized in that:
R1 is a methoxy group,
R2 is a methyl group,
X is —CH₂—CH₂—,
Y is HNC*(O), wherein C* is linked to R3 and
R3 is chosen from a group consisting of:

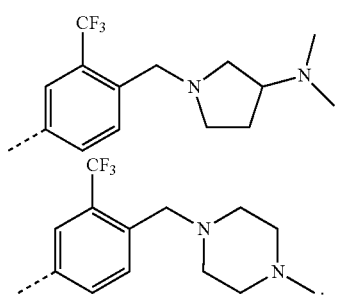

In a preferred embodiment of the present invention, all the specific embodiments detailed above can also be characterized in that R1 is C=O instead of CH₂.

In a preferred embodiment of the present invention, all the specific embodiments detailed above can also be characterized in that R1 is a hydroxyl group.

In a preferred embodiment of the present invention, all the specific embodiments detailed above can also be characterized in that R1 is the corresponding salt of the a hydroxyl group, preferably the sodium salt, the potassium salt, lithium salt, magnesium salt or calcium salt.

All the compounds of formula (I) or (II) disclosed here can be the pharmaceutically acceptable addition salts, enantiomers, diastereoisomers thereof, as well as mixtures thereof.

All the compounds according to the invention can be in solvated form and in non-solvated form.

Products Synthesis Methods

The invention also relates to preparation methods of the compounds starting from e.g. 5-nitro-1H-pyrrolo[2,3-b]pyridine-2-carboxylic acid methyl ester and 1-(5-nitro-1H-pyrrolo[2,3-b]pyridin-2-yl)-ethanone.

In a first embodiment, the method according to the invention is represented in scheme 1.

The synthesis of the key intermediate methyl amide compound is represented in Scheme 1.

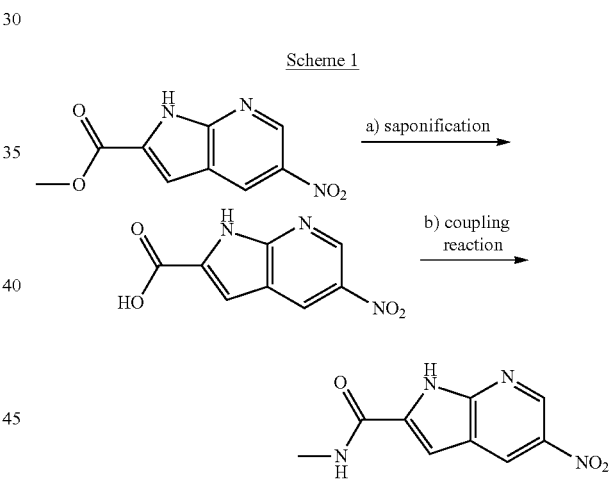

The method comprises at least the steps of:
a) saponification of 5-nitro-1H-pyrrolo[2,3-b]pyridine-2-carboxylic acid methyl ester to providing the carboxylic acid derivative, preferably by the use of KOH, in MeOH/H₂O,
b) coupling reaction comprising at least one activating agent such as 2-(7-aza-1H-benzotriazol-1-yl)-N,N,N',N'-tetramethyluronium hexafluorophosphate (HATU) in the presence of a base such as diisopropylethylamine (DIEA), or a carbodiimide such as dicyclocarbodiimide (DCC).

In another embodiment, the method is represented by Scheme 2.

The synthesis of the key intermediate amine compounds is represented in Scheme 2:

Scheme 2

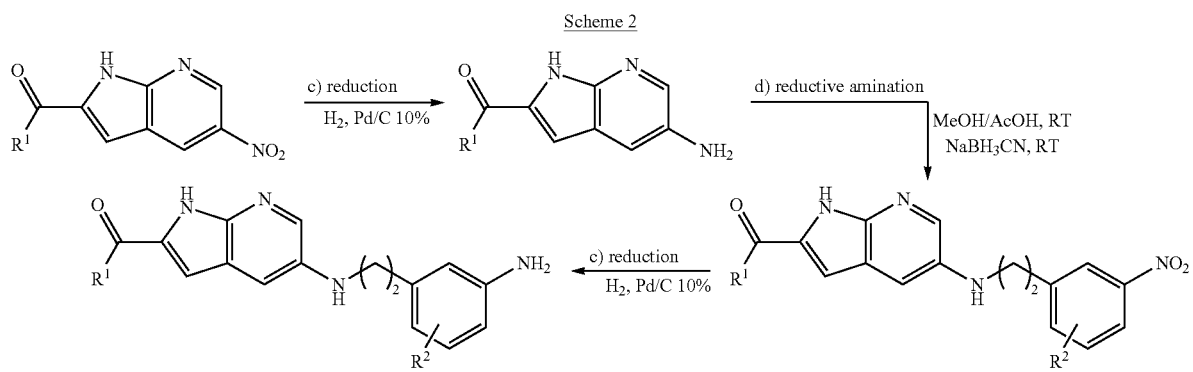

wherein R' and R2 are as previously defined.

Advantageously, the method comprises at least one of the steps of:

c) reduction: for example a catalytic hydrogenation of the resulting nitro compounds, in the presence of palladium on charcoal under hydrogen atmosphere (Seela, F., Gumbiowski, R. *Heterocycles,* 1989, 29 (4), 795-805), d) reductive amination: for example 5-amino-1H-pyrrolo[2,3-b]pyridine-2-carboxylic acid methyl ester is reacted with various aromatic aldehydes in the presence of boron hydride to give corresponding benzylic amines (Wang, Dong Mei et al *Journal of Combinatorial Chemistry,* 2009, 11(4), 556-575).

The skilled person in the art will naturally apply all other well-known synthesis techniques to obtain these types of compounds.

In another embodiment, a method to synthesize the ureido compounds of the present invention is represented in Scheme 3

Scheme 3

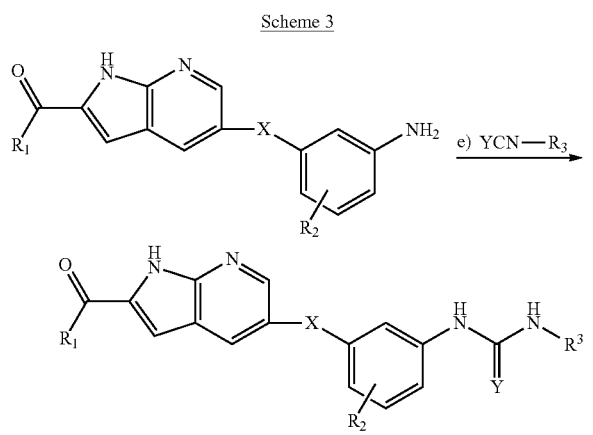

wherein R1, R2, R3, X are as previously defined and Y is O or S.

Advantageously, a method to synthesize the ureido compounds thus comprises at least a step of:

e) reaction of the key intermediate amine compound with various isocyanates or thioisocyanates.

The skilled person in the art will naturally apply all other well-known synthesis techniques to obtain these types of ureido compounds.

In another embodiment, a method to synthesize the sulfonamide compounds of the present invention is represented in Scheme 4:

Scheme 4

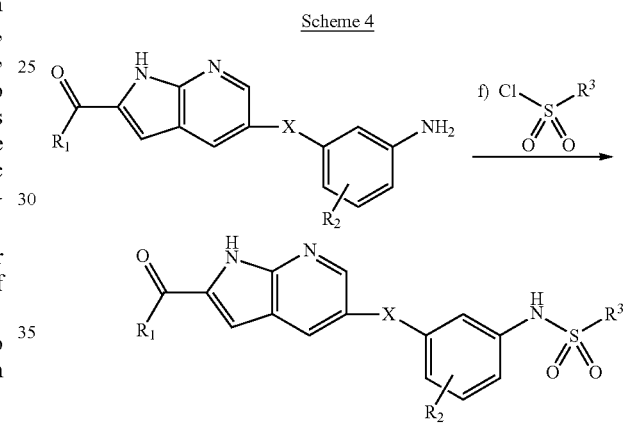

wherein R1, R2, R3 and X are as defined above.

Advantageously, a method to synthesize the sulfonamide compounds of the present invention comprises at least a step of:

f) reaction of the key intermediate amine compound with various sulfonyl chlorides.

The skilled person in the art will naturally apply all other well-known synthesis techniques to obtain these types of sulfonamide compounds.

In another embodiment, concerning a method to synthesize the amide compounds of the present invention, two methods amongst other are represented in Scheme 5:

Scheme 5

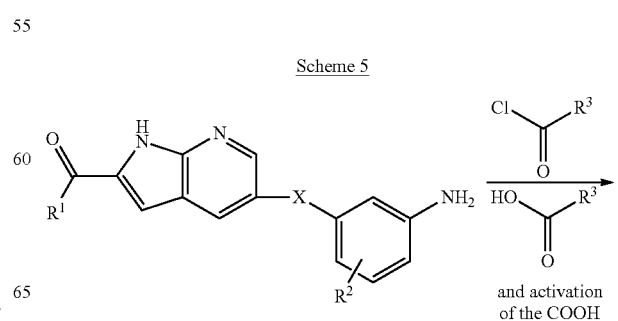

-continued

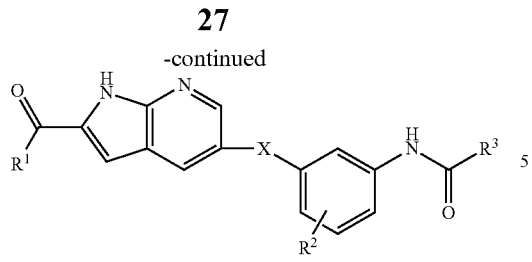

wherein R1, R2, R3 and X are as previously defined.

Advantageously a method of Scheme 5 comprises at least a step of:
g) reaction of the key intermediate amine compound with various acyl chlorides or carboxylic acids (Mouaddib, A., Joseph, B. et al., *Synthesis*, 2000, (4), 549-556).

The skilled person in the art will naturally apply all other well-known synthesis techniques to obtain these types of amide compounds.

Another embodiment concerns the method to synthesize the non-commercially available carboxylic acids obtained according to the following Scheme 6, Scheme 7, Scheme 8 and/or Scheme 9.

4-aminomethyl-3-trifluoromethyl-benzoic acids or 4-aminomethyl-3-fluoro-benzoic acids A method which was used in the present invention to synthesize 4-aminomethyl-3-substituted-benzoic acids is represented in Scheme 6:

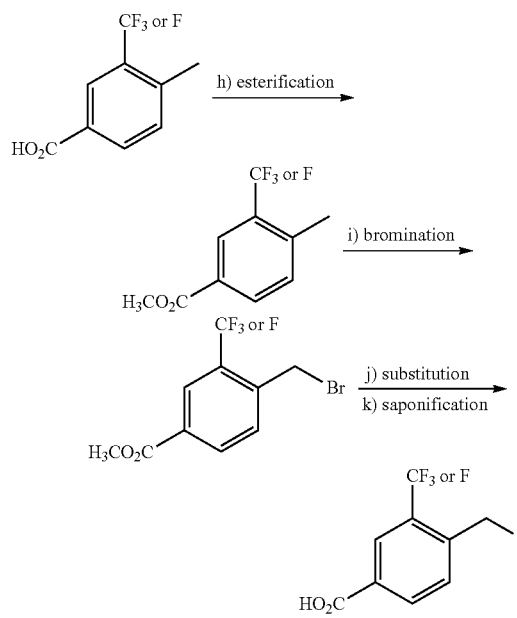

where $NR_{12}R_{13}$ in Scheme 6 can represent:

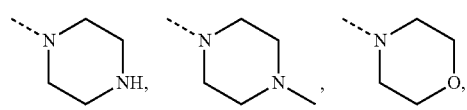

-continued

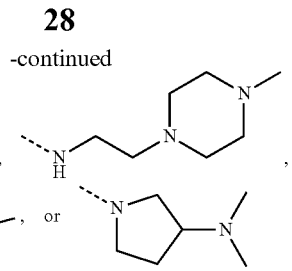

Advantageously, a method to synthesize 4-aminomethyl-3-substituted-benzoic acids comprises at least one of the following steps:
h) esterification of 4-methyl-benzoic acid derivative, preferably in methanol, advantageously in an acid medium to give the methyl ester,
i) radical bromination of the methyl group, preferably by N-bromosuccinimide (NBS), advantageously in presence of azobisisobutyronitrile(AIBN) as radical initiator (Sun, Yewei et al, *Bioorganic & Medicinal Chemistry*, 2008, 16(19), 8868-8874),
j) brome substitution by various primary and secondary amines,
k) saponification of the ester, preferably methyl ester.

The skilled person in the art will naturally apply all other well-known synthesis techniques to obtain substituted 4-aminomethyl-benzoic acids, however several or even all steps h), i), j) and k) are preferably comprised in the method.

3-amino-5-trifluoromethyl-benzoic acids

A method which was used in the present invention to synthesize 3-amino-5-trifluoromethyl-benzoic acids is represented in Scheme 7:

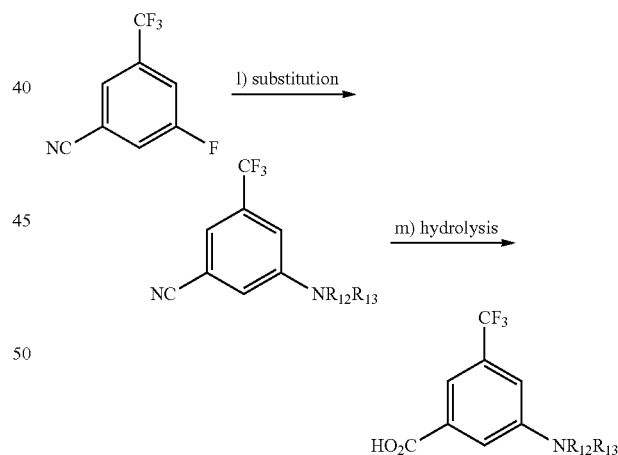

where $NR_{12}R_{13}$ in Scheme 7 can represent:

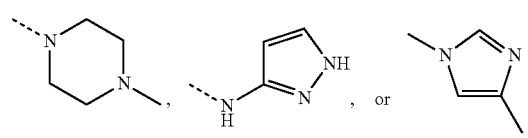

Advantageously, a method to synthesize 3-amino-5-trifluoromethyl-benzoic acid comprises at least one of the following steps:

l) fluorine substitution by various primary and secondary amines,
m) hydrolysis of the nitrile function to the corresponding carboxylic acid.

The skilled person in the art will naturally apply all other well-known synthesis techniques to obtain 3-amino-5-trifluoromethyl-benzoic acids, however both steps 1) and m) are preferably comprised in the method.

3-methyl-5-(4-methyl-piperazin-1-ylmethyl)-benzoic acid

A method which was used in the present invention to synthesize 3-methyl-5-(4-methyl-piperazin-1-ylmethyl)-benzoic acid is represented in Scheme 8:

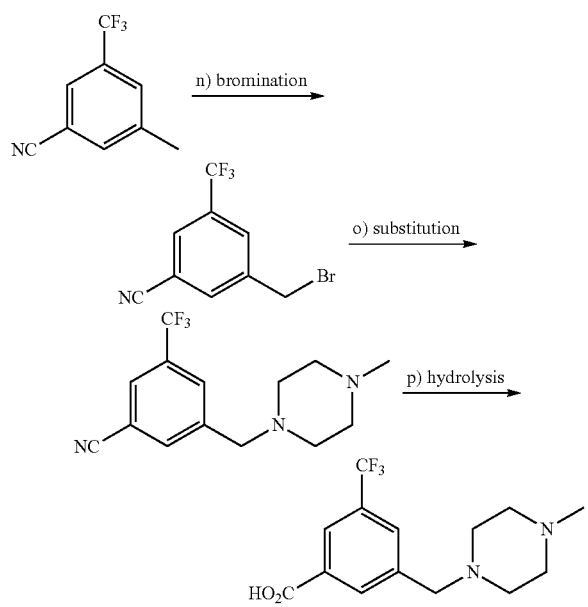

Advantageously, the method comprises at least one of the steps:
n) radical bromination of the methyl group by N-bromosuccinimide (NBS) in presence of Azobisisobutyronitrile (AIBN) as radical initiator (Sun, Yewei et al, *Bioorganic & Medicinal Chemistry*, 2008, 16(19), 8868-8874),
o) brome substitution by N-methylpiperazine,
p) hydrolysis of the nitrile function to the corresponding carboxylic acid.

The skilled person in the art will naturally apply all other well-known synthesis techniques to obtain 3-methyl-5-(4-methyl-piperazin-1-ylmethyl)-benzoic acid, however several or even all steps n), o) and p) are preferably comprised in the method.

3-dimethylamino-5-trifluoromethyl-benzoic acid

A method which was used in the present invention to synthesize 3-dimethylamino-5-trifluoromethyl-benzoic acid is represented in Scheme 9:

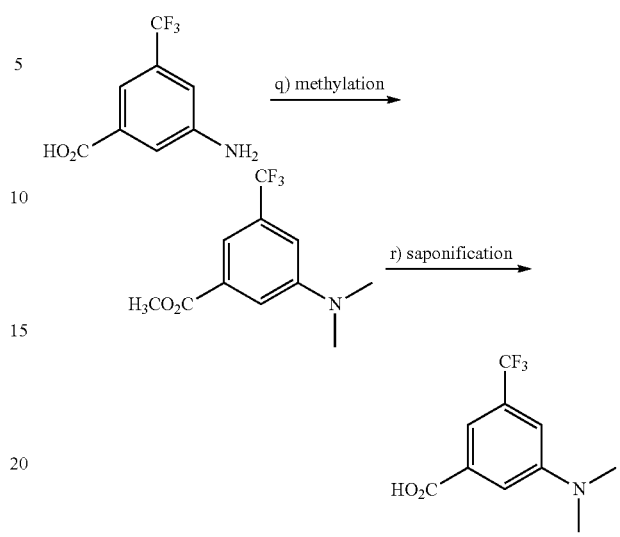

Advantageously, the method comprises at least one of the steps:
q) total methylation of the acid and amine functions, preferably by means of methyl iodide,
r) saponification of the resulting ester to give the corresponding carboxylic acid.

The skilled person in the art will naturally apply all other well-known synthesis techniques to obtain 3-dimethylamino-5-trifluoromethyl-benzoic acid, however several or even both steps q) and r) are preferably comprised in the method.

4-aminomethyl-benzoic acids

A method which was used in the present invention to synthesize 4-aminomethyl-benzoic acids is represented in Scheme 10

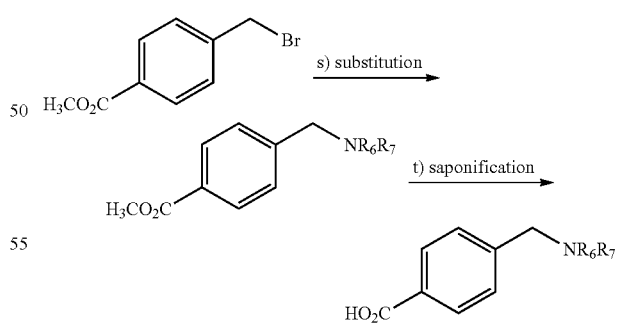

wherein $NR_6R_7$ in Scheme 10 can represent any one of:

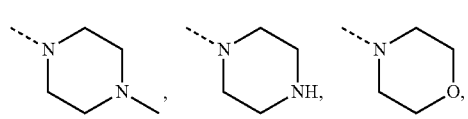

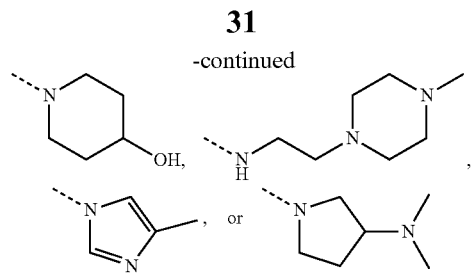

Advantageously, the method comprises at least one of the following steps:
s) brome substitution by various primary and secondary amines,
t) saponification of the methylic ester.

The skilled person in the art will naturally apply all other well-known synthesis techniques to obtain 4-aminomethylbenzoic acids, however several or even both steps s) and t) are preferably comprised in the method.

Another embodiment concerns the method to synthesize the thioamides obtained according to the following Scheme 11:

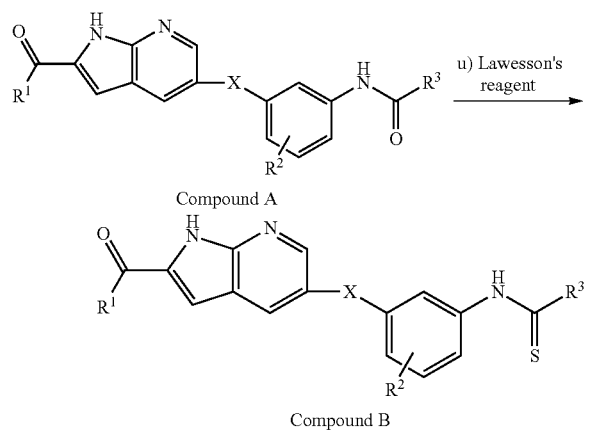

wherein X, R1, R2 and R3 are as defined as previously.

Advantageously, the method comprises at least the following step:
u) treatment of compound A with Lawesson's reagent (LR) to form it's thioamide derivative compound B.

The skilled person in the art will naturally apply all other well-known synthesis techniques to obtain compound B, however step u) is preferably comprised in the method.

Another embodiment concerns the method to synthesize acid compounds according to the present invention is represented in Scheme 12:

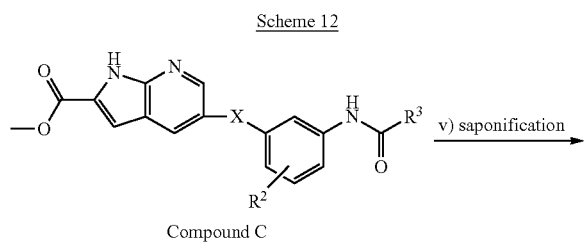

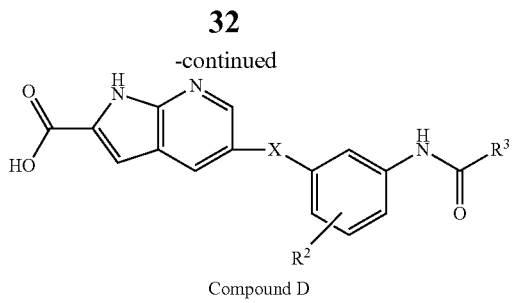

wherein R2, R3 and X are as defined above.

Advantageously, the method comprises at least the following step:
v) saponification of the methyl ester compound C to afford the carboxylic acid derivative, i.e. compound D.

The skilled person in the art will naturally apply all other well-known synthesis techniques to obtain compound D, however step v) is preferably comprised in the method.

The invention also relates to the method of preparation of the compounds starting e.g. from 5-cyano-1H-pyrrolo[2,3-b]pyridine-2-carboxylic acid methyl ester and 2-acetyl-1H-pyrrolo[2,3-b]pyridine-5-carbonitrile.

Another embodiment concerns the method to synthesize the key intermediate nitro compound E is represented in Scheme 13.

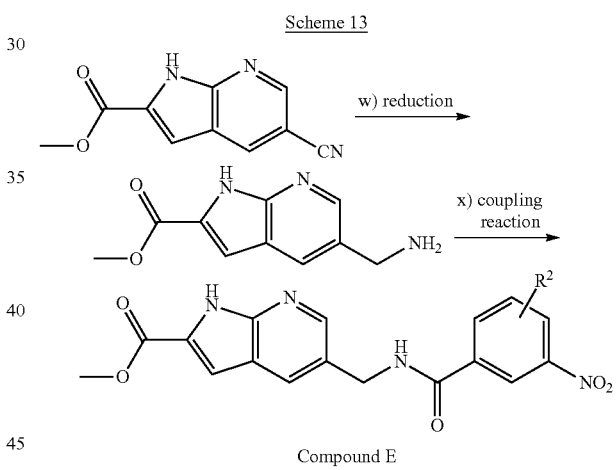

wherein R2 is as previously defined.

Advantageously, the method comprises at least one of the following steps:
w) catalytic hydrogenation of the 5-cyano-1H-pyrrolo[2,3-b]pyridine-2-carboxylic acid methyl ester, preferably in the presence of Raney Nickel,
x) coupling reaction comprising at least one activating agent such as 2-(7-aza-1H-benzotriazol-1-yl)-N,N,N',N'-tetramethyluronium hexafluorophosphate (HATU) in the presence of a base such as diisopropylethylamine (DIEA), a carbodiimide such as dicyclocarbodiimide (DCC), preferably HATU and diisopropylethylamine (DIEA).

The skilled person in the art will naturally apply all other well-known synthesis techniques to obtain the key intermediate nitro compound E, however steps w) and/or x) are preferably comprised in the method.

In another embodiment, the method to synthesize the key intermediate compounds F, F', G and H is represented in Scheme 14.

Scheme 14

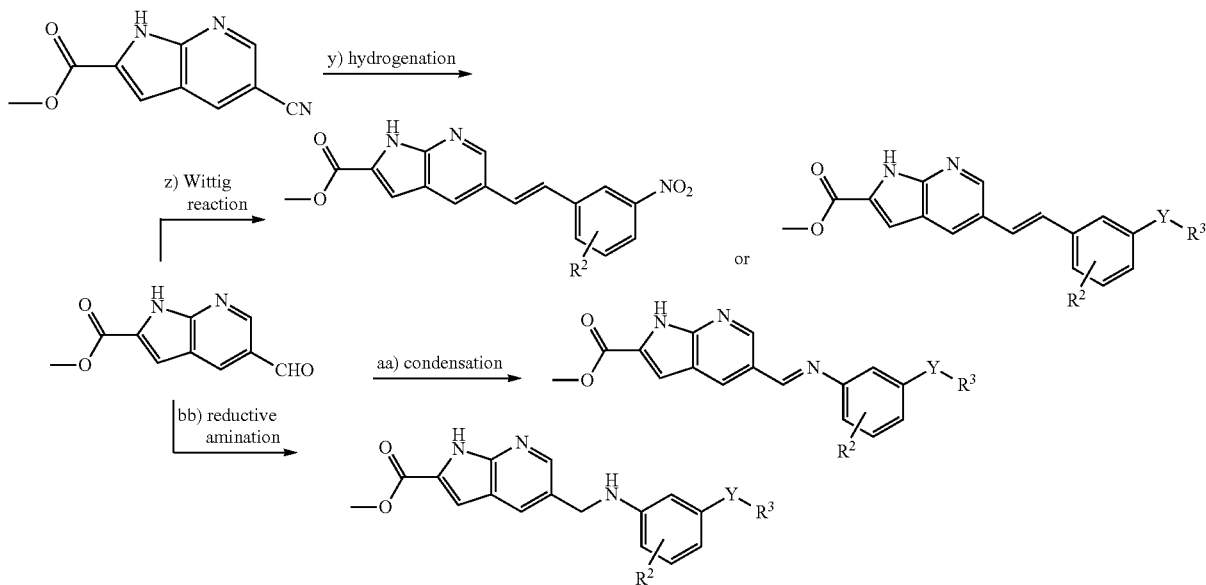

Compounds F and F' (top), Compound G, (middle), Compound H (bottom)

wherein R2, R3 and Y are as previously defined.

Advantageously, the method comprises at least one of the following steps:

y) catalytic hydrogenation of the 5-cyano-1H-pyrrolo[2,3-b]pyridine-2-carboxylic acid methyl ester, preferably in the presence of Raney Nickel to give its aldehyde derivative, z) Wittig reaction between the aldehyde and various aromatic triphenyl phosphonium, aa) condensation of aldehyde intermediate with primary amines, bb) reductive amination of the 5-formyl-1H-pyrrolo[2,3-b]pyridine-2-carboxylic acid methyl ester with various substituted aniline, preferably in the presence of boron hydride (Wang, Dong Mei et al *Journal of Combinatorial Chemistry*, 2009, 11(4), 556-575)

The skilled person in the art will naturally apply all other well-known synthesis techniques to obtain the key nitro intermediates F and final compounds F', or final compounds G and H, however steps y), z), aa) and/or bb) are preferably comprised in the method.

In another embodiment, the method to synthesize the key nitro intermediate compound I is represented in Scheme 15.

Scheme 15

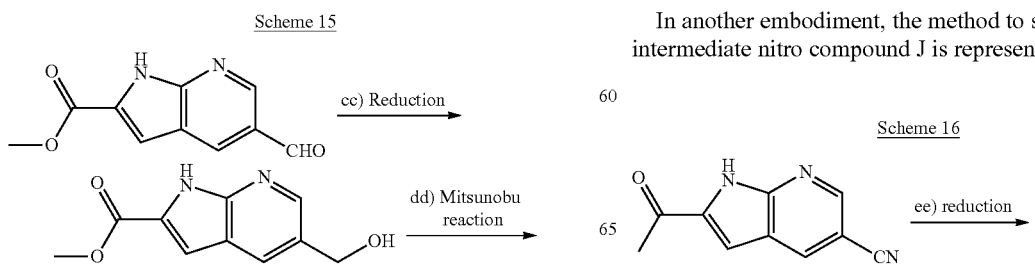

-continued

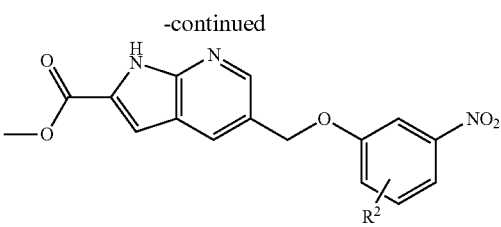

Compound I wherein R2 is as previously defined.

Advantageously, the method comprises at least the following step:

cc) catalytic hydrogenation of the 5-formyl-1H-pyrrolo[2,3-b]pyridine-2-carboxylic acid methyl ester by Diisobutylaluminium hydride (DIBAL) to give its alcohol derivative, dd) Mitsunobu reaction between the 5-hydroxymethyl-1H-pyrrolo[2,3-b]pyridine-2-carboxylic acid methyl ester and various phenolic compounds.

The skilled person in the art will naturally apply all other well-known synthesis techniques to obtain the key intermediate nitro compounds I, however steps cc) and/or dd) are preferably comprised in the method.

In another embodiment, the method to synthesize the key intermediate nitro compound J is represented in Scheme 16.

Scheme 16

Scheme 18

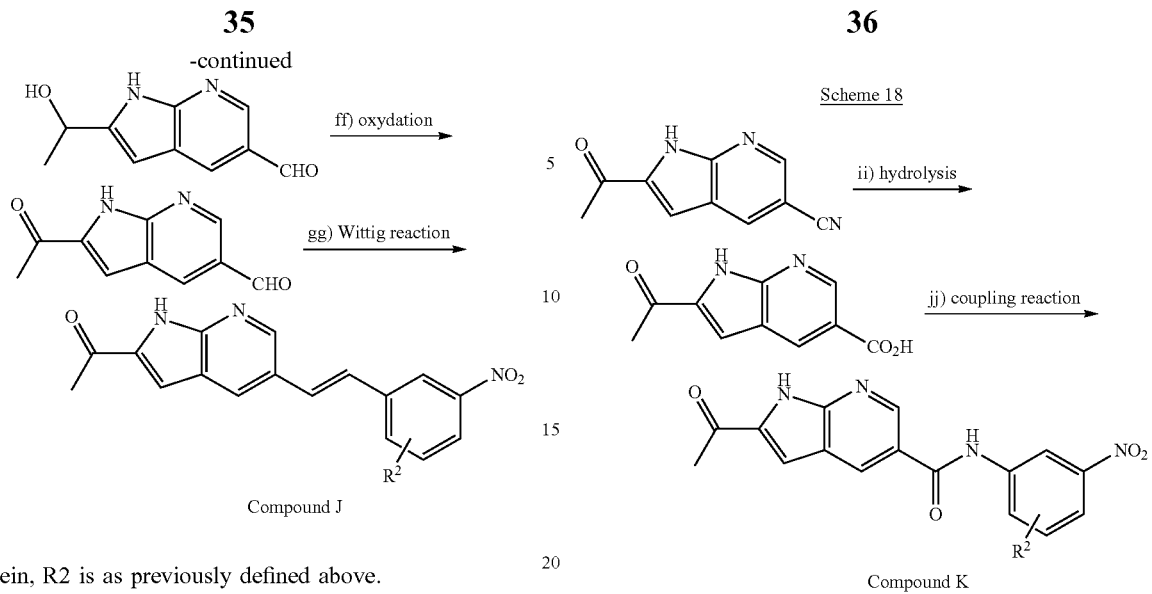

Compound K wherein, R2 is as previously defined above.

-continued

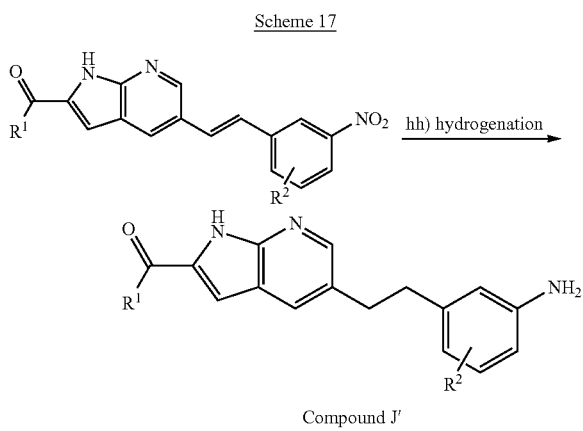

Compound J wherein, R2 is as previously defined above.

Advantageously, the method comprises at least one of the following steps:
- ee) catalytic hydrogenation of 2-acetyl-1H-pyrrolo[2,3-b]pyridine-5-carbonitrile, preferably with Diisobutylaluminium hydride (DIBAL) followed by hydrolysis by a mixture of methanol and aqueous sulfuric acid to give its alcohol-aldehyde derivative,
- ff) selective reoxydation of the alcohol, preferably by mean of manganese dioxide to give the acetyl derivative,
- gg) Wittig reaction between the 2-acetyl-1H-pyrrolo[2,3-b]pyridine-5-carbaldehyde and various aromatic triphenyl phosphonium.

The skilled person in the art will naturally apply all other well-known synthesis techniques to obtain the key intermediate nitro compounds J, however steps ee), ff) and gg) are preferably comprised in the method.

In another embodiment, the method to synthesize the key intermediate nitro compound J' is represented in Scheme 17.

Scheme 17

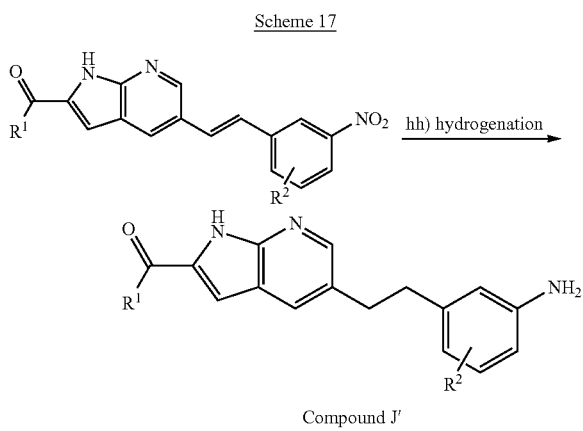

Compound J' wherein, R1 and R2 are as previously defined above.

Advantageously, the method comprises at least the following step:
- hh) a complete hydrogenation of the unsaturated nitro compound, preferably under hydrogen pressure with palladium on charcoal.

In another embodiment, a method to synthesize the key intermediate nitro compound K is represented in Scheme 18.

Advantageously, the method comprises at least one of the following steps:
- ii) hydrolysis of 2-acetyl-1H-pyrrolo[2,3-b]pyridine-5-carbonitrile, preferably with sodium hydroxyde to give its carboxylic acid derivative,
- jj) coupling reaction comprising at least one activating agent such as 2-(7-aza-1H-benzotriazol-1-yl)-N,N,N',N'-tetramethyluronium hexafluorophosphate (HATU) in the presence of a base such as diisopropylethylamine (DIEA), a carbodiimide such as dicyclocarbodiimide (DCC), preferably HATU and diisopropylethylamine (DIEA).

The skilled person in the art will naturally apply all other well-known synthesis techniques to obtain the key intermediate nitro compounds K, however steps ii), and jj) are preferably comprised in the method.

In another embodiment, a method to synthesize amide compounds L is represented in Scheme 19.

Scheme 19

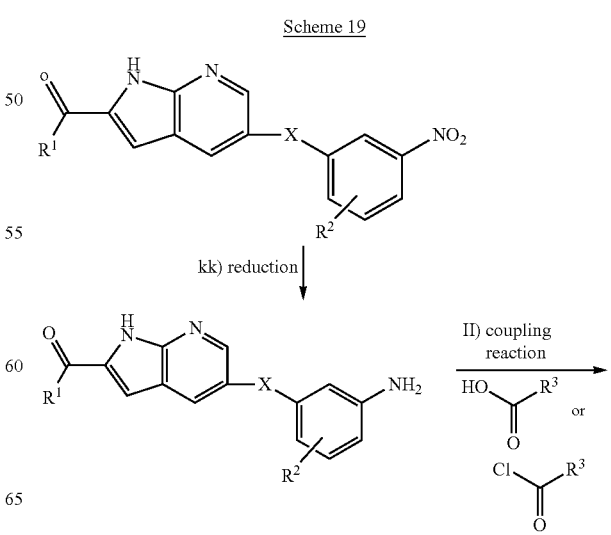

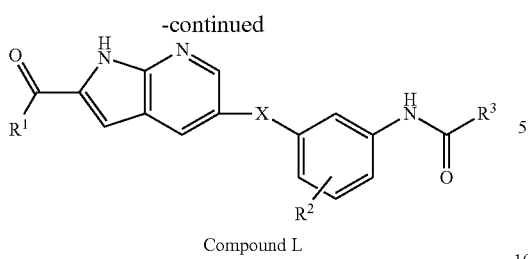

Compound L wherein R1, R2, R3 and X are as defined above.

Advantageously, the method comprises at least one of the following steps:
- kk) catalytic hydrogenation of the key intermediate nitro compound, in the presence of palladium on charcoal under hydrogen atmosphere (Seela, F., Gumbiowski, R. *Heterocycles,* 1989, 29 (4), 795-805),or with zinc powder,
- ll) reaction of the resulting amine compound with various carboxylic acids or acid halides to give the corresponding amide (Mouaddib, A., Joseph, B. et al., *Synthesis,* 2000, (4), 549-556)

The skilled person in the art will naturally apply all other well-known synthesis techniques to obtain the key intermediate amide compounds L, however steps kk) and ll) are preferably comprised in the method.

In another embodiment, a method to synthesize amide compounds M is represented in Scheme 20.

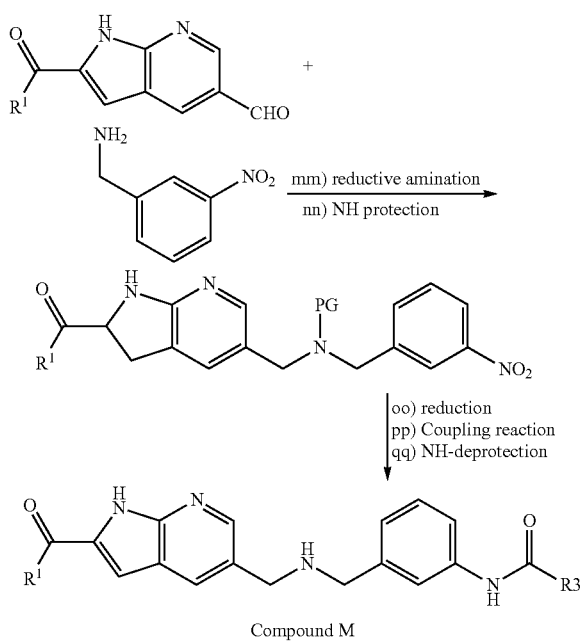

Compound M wherein R1 and R3 are as defined above.

Advantageously, the method comprises at least one of the following steps:
- mm) reductive amination of the aldehyde derivative with 3-nitrobenzylamine under acidic conditions in the presence of borohydride,
- nn) protection step of secondary amide, preferably with carbamate protecting group,
- oo) catalytic hydrogenation of the key intermediate nitro compound, in the presence of palladium on charcoal under hydrogen atmosphere (Seela, F., Gumbiowski, R. *Heterocycles,* 1989, 29 (4), 795-805),
- pp) coupling reaction with various carboxylic acids,
- qq) deprotection step of the final amine compound.

The skilled person in the art will naturally apply all other well-known synthesis techniques to obtain the key intermediate amide compounds M, however steps mm), nn), oo), pp) and qq) are preferably comprised in the method.

In another embodiment, a method to synthesize final compound N is presented in Scheme 21.

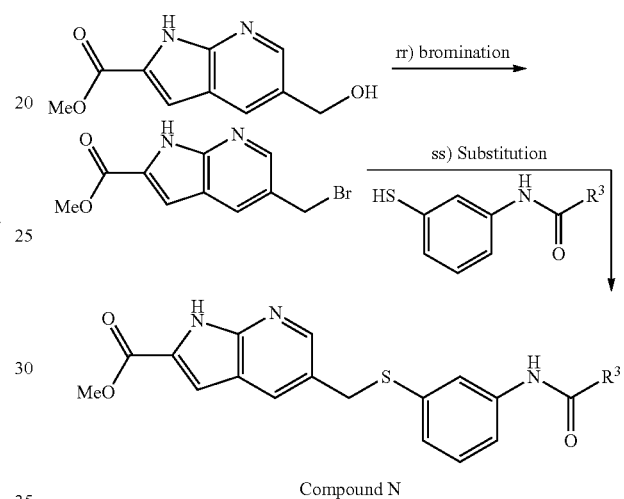

Compound N wherein, R3 is as previously defined above.

Advantageously, the method comprises at least one of the following steps:
- rr) Nucleophilic substitution of 5-Hydroxymethyl-1H-pyrrolo[2,3-b]pyridine-2-carboxylic acid methyl ester with bromine reagent, preferably with phosphorus tribromide,
- ss) Bromine nucleophilic substitution with N-(3-mercapto-phenyl)-benzamide derivative.

The skilled person in the art will naturally apply all other well-known synthesis techniques to obtain the final compound N, however steps rr) and ss) are preferably comprised in the method.

In another embodiment, a method to synthesize final compound O is presented in Scheme 22.

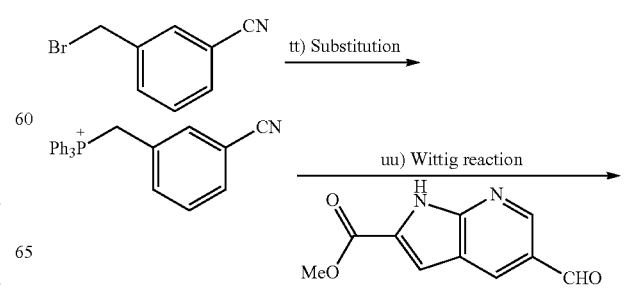

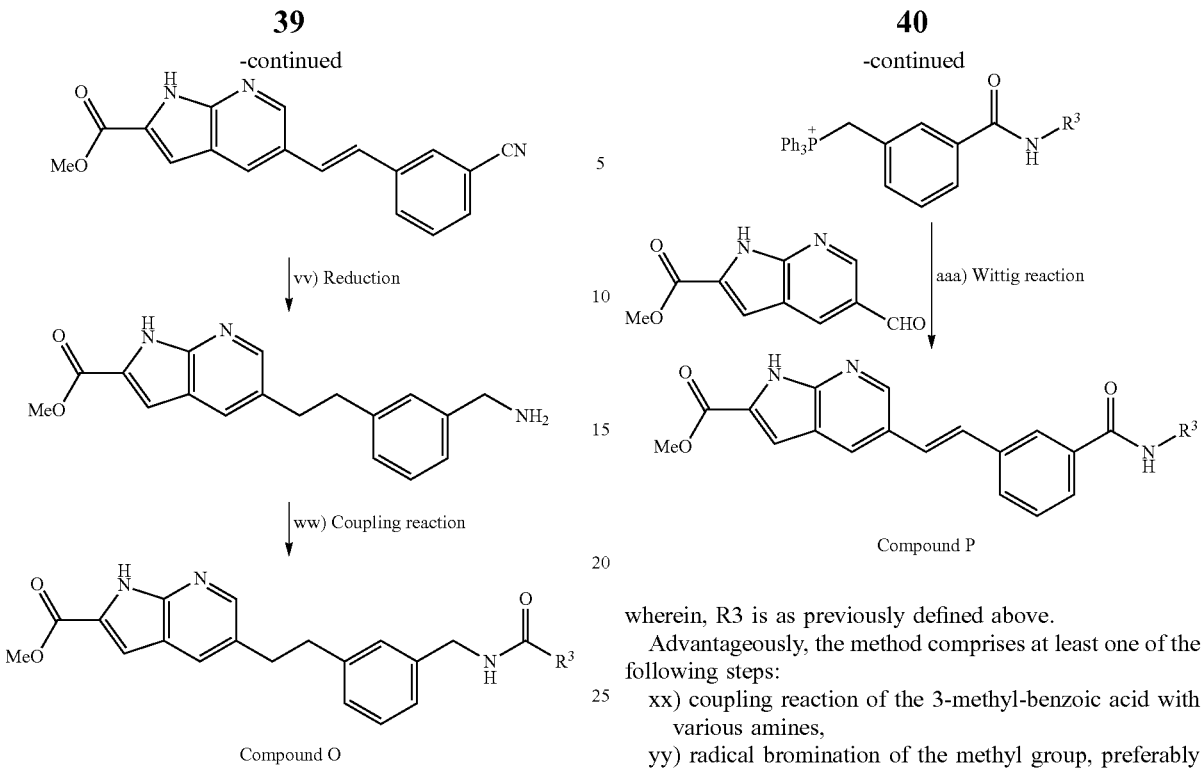

Compound O wherein, R3 is as previously defined above.

Advantageously, the method comprises at least one of the following steps:

tt) bromine substitution by triphenylphosphine,
uu) Wittig reaction between the triphenyl phosphonium and the 5-formyl-1H-pyrrolo[2,3-b]pyridine-2-carboxylic acid methyl ester,
vv) reduction by catalytic hydrogenation under pressure of hydrogen in presence of palladium on charcoal,
ww) coupling reaction of the resulting amine with various carboxylic acids comprising at least one activating agent such as 2-(7-aza-1H-benzotriazol-1-yl)-N,N,N',N'-tetramethyluronium hexafluorophosphate (HATU) in the presence of a base such as diisopropylethylamine (DIEA), a carbodiimide such as dicyclocarbodiimide (DCC), preferably HATU and diisopropylethylamine (DIEA).

The skilled person in the art will naturally apply all other well-known synthesis techniques to obtain the final compound O, however steps tt), uu), vv) and ww) are preferably comprised in the method.

In another embodiment, a method to synthesize final compound P is presented in Scheme 23.

Scheme 23

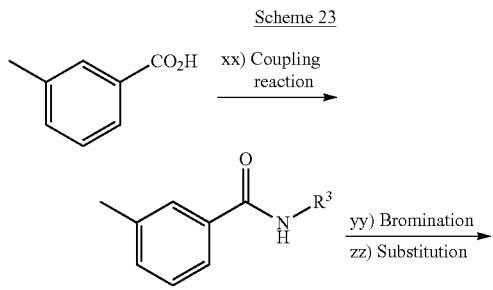

Compound P wherein, R3 is as previously defined above.

Advantageously, the method comprises at least one of the following steps:

xx) coupling reaction of the 3-methyl-benzoic acid with various amines,
yy) radical bromination of the methyl group, preferably by N-bromosuccinimide (NBS), advantageously in presence of azobisisobutyronitrile(AIBN) as radical initiator (Sun, Yewei et al, *Bioorganic & Medicinal Chemistry*, 2008, 16(19), 8868-8874),
zz) bromine substitution by triphenylphosphine,
aaa) Wittig reaction between the triphenyl phosphonium and the 5-formyl-1H-pyrrolo[2,3-b]pyridine-2-carboxylic acid methyl ester.

The skilled person in the art will naturally apply all other well-known synthesis techniques to obtain the final compound P, however steps xx), yy), zz) and aaa) are preferably comprised in the method.

In another embodiment, a method to synthesize amide compounds according to the present invention is represented in Scheme 24

Scheme 24

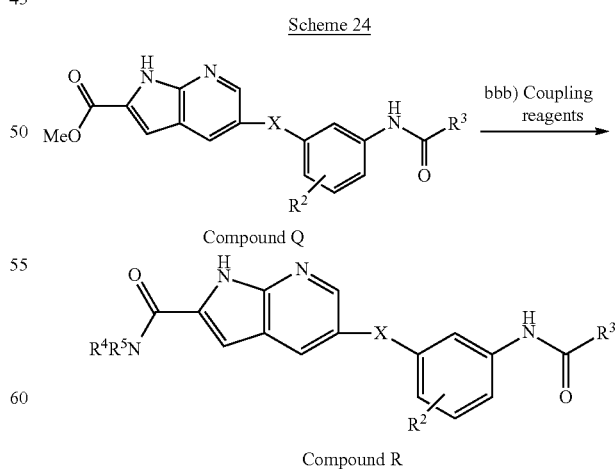

Compound R wherein R2, R3, R4, R5 and X are as defined above.

Advantageously, the method comprises at least the following step:

bbb) coupling reaction comprising at least one activating agent such as 2-(7-aza-1H-benzotriazol-1-yl)-N,N,N', N'-tetramethyluronium hexafluorophosphate (HATU) in the presence of a base such as diisopropylethylamine (DIEA), a carbodiimide such as dicyclocarbodiimide (DCC), preferably HATU and diisopropylethylamine (DIEA).

The skilled person in the art will naturally apply all other well-known synthesis techniques to obtain compound R, however step bbb) is preferably comprised in the method.

Uses

The present invention also relates to the use of the compounds according to the invention as inhibitors of protein kinases. Depending of the type of Cancer, one or several kinase proteins will be aimed.

In one embodiment, the compounds according to the invention are used as inhibitor of protein kinase BRAF.

In another embodiment, the compounds according to the invention are used as inhibitors of protein kinase EGFR (ErbB1).

In another embodiment, the compounds according to the invention are used as inhibitors of protein kinase EGFR (ErbB1) T790M L858R.

In another embodiment, the compounds according to the invention are used as inhibitors of protein kinase FGFR2.

In another embodiment, the compounds according to the invention are used as inhibitors of protein kinase KDR (VEGFR2).

In another embodiment, the compounds according to the invention are used as inhibitors of protein kinase PDGFRA (PDGFR alpha).

In another embodiment, the compounds according to the invention are used as inhibitors of protein kinase SRC.

In another embodiment, the compounds according to the invention are used as inhibitors of protein kinase ABL.

In another embodiment, the compounds according to the invention are used as inhibitors of protein kinase ABL T315I.

In another embodiment, the compounds according to the invention are used as inhibitors of protein kinase FGFR1.

In another embodiment, the compounds according to the invention are used as inhibitors of protein kinase VEGFR1.

In another embodiment, the compounds according to the invention are used as inhibitors of protein kinase PDGFRB (PDGFR beta).

In another embodiment, the compounds according to the invention are used as inhibitors of protein kinase ABL E255K.

In another embodiment, the compounds according to the invention are used as inhibitors of protein kinase ABL G250E.

In another embodiment, the compounds according to the invention are used as inhibitors of protein kinase ABL Y253F.

In another embodiment, the compounds according to the invention are used as inhibitors of protein kinase ABL2.

In another embodiment, the compounds according to the invention are used as inhibitors of protein kinase BLK.

In another embodiment, the compounds according to the invention are used as inhibitors of protein kinase BMX.

In another embodiment, the compounds according to the invention are used as inhibitors of protein kinase BRAF V600E.

In another embodiment, the compounds according to the invention are used as inhibitors of protein kinase BTK.

In another embodiment, the compounds according to the invention are used as inhibitors of protein kinase CSK.

In another embodiment, the compounds according to the invention are used as inhibitors of protein kinase EPHA1.

In another embodiment, the compounds according to the invention are used as inhibitors of protein kinase EPHA2.

In another embodiment, the compounds according to the invention are used as inhibitors of protein kinase EPHA4.

In another embodiment, the compounds according to the invention are used as inhibitors of protein kinase EPHB2.

In another embodiment, the compounds according to the invention are used as inhibitors of protein kinase EPHB4.

In another embodiment, the compounds according to the invention are used as inhibitors of protein kinase HER2.

In another embodiment, the compounds according to the invention are used as inhibitors of protein kinase ERBB4.

In another embodiment, the compounds according to the invention are used as inhibitors of protein kinase FES.

In another embodiment, the compounds according to the invention are used as inhibitors of protein kinase FGR.

In another embodiment, the compounds according to the invention are used as inhibitors of protein kinase FLT3.

In another embodiment, the compounds according to the invention are used as inhibitors of protein kinase FMS.

In another embodiment, the compounds according to the invention are used as inhibitors of protein kinase FRK.

In another embodiment, the compounds according to the invention are used as inhibitors of protein kinase FYN.

In another embodiment, the compounds according to the invention are used as inhibitors of protein kinase HCK.

In another embodiment, the compounds according to the invention are used as inhibitors of protein kinase LCK.

In another embodiment, the compounds according to the invention are used as inhibitors of protein kinase LYN.

In another embodiment, the compounds according to the invention are used as inhibitors of protein kinase MAPK14.

In another embodiment, the compounds according to the invention are used as inhibitors of protein kinase ERK2.

In another embodiment, the compounds according to the invention are used as inhibitors of protein kinase PKC theta.

In another embodiment, the compounds according to the invention are used as inhibitors of protein kinase RET.

In another embodiment, the compounds according to the invention are used as inhibitors of protein kinase VEGFR3.

In another embodiment, the compounds according to the invention are used as inhibitors of protein kinase YES.

Preferably, the compounds according to the invention are used as inhibitor of any one or several of the protein kinases chosen in the group consisting of BRAF, EGFR (ErbB1), EGFR (ErbB1) T790M L858R, FGFR2, KDR (VEGFR2), PDGFRA (PDGFR alpha), SRC, ABL, ABL T315I, FGFR1, VEGFR1, PDGFRB (PDGFR beta).

More preferably, the compounds according to the invention are used as inhibitor of any one or several of the protein kinases chosen in the group consisting of BRAF, EGFR (ErbB1), EGFR (ErbB1) T790M L858R, FGFR2, KDR (VEGFR2), PDGFRA (PDGFR alpha), SRC.

In another embodiment, the compounds according to the invention are used as inhibitors of the proliferation of A549 cancer cell line.

In another embodiment, the compounds according to the invention are used as inhibitors of the proliferation of HepG2 cancer cell line.

In another embodiment, the compounds according to the invention are used as inhibitors of the proliferation of HuCCT1 cancer cell line.

In another embodiment, the compounds according to the invention are used as inhibitors of the proliferation of HuH6 Clone 5 cancer cell line.

In another embodiment, the compounds according to the invention are used as inhibitors the proliferation of HuH7 cancer cell line.

In another embodiment, the compounds according to the invention are used as inhibitors of the proliferation of PC-3 cancer cell line.

In another embodiment, the compounds according to the invention are used as inhibitors of the proliferation of Caki-2 cancer cell line.

In another embodiment, the compounds according to the invention are used as inhibitors of the proliferation of MDA-MB-231 cancer cell line.

In another embodiment, the compounds according to the invention are used as inhibitors of the proliferation of HT29 cancer cell line.

In another embodiment, the compounds according to the invention are used as inhibitors of the proliferation of BxPC-3 cancer cell line.

In another embodiment, the compounds according to the invention are used as inhibitors of the proliferation of H1975 cancer cell line.

In another embodiment, the compounds according to the invention are used as inhibitors of the proliferation of BaF3 WT.

In another embodiment, the compounds according to the invention are used as inhibitors of the proliferation of BaF3 T315I.

In another embodiment, the compounds according to the invention are used as inhibitors of the proliferation of BaF3 G250A.

In another embodiment, the compounds according to the invention are used as inhibitors of the proliferation of BaF3 G250E.

In another embodiment, the compounds according to the invention are used as inhibitors of the proliferation of BaF3 G250A+E279N.

In another embodiment, the compounds according to the invention are used as inhibitors of the proliferation of BaF3 E255K+M351T.

In another embodiment, the compounds according to the invention are used as inhibitors of the proliferation and migration of HRMEC primary cells.

In another embodiment, the compounds according to the invention are used as inhibitors of the proliferation and migration of HeLa cancer cell line.

In another embodiment, the compounds according to the invention are used as inhibitors of the proliferation and migration of HUVEC primary cells.

Preferably, the compounds according to the invention are able to inhibit the proliferation of at least one of cancer cell lines chosen in the group consisting of A549, HepG2, HuCCT1, HuH6 Clone 5, HuH7, HT29, H1975, PC3, Caki-2, MDA-MB-231, BxPC3, Hela and/or the proliferation of at least one of primary cells among HUVEC and HRMEC.

The compounds, and of course pharmaceutical compositions comprising such compounds, of the invention can be used in the treatment of pathologies associated with deregulation of protein kinases:
  in the case of immune disorders, inflammatory diseases, thrombotic diseases, neurodegenerative diseases, bone diseases, macular degeneration, fibrosis, cystogenesis, hyperproliferative diseases,
  in the case of all cancers more particularly liquid tumors such as hematological cancers such as leukemias, chronic or acute myeloproliferative disorders or solid tumors such as squamous cell cancer, small-cell lung cancer, non-small cell lung cancer, gastrointestinal cancers, pancreatic cancer, glial cell tumors such as glioblastoma and neurofibromatosis, cervical cancer, ovarian cancer, liver cancer, bladder cancer, breast cancer, melanoma, colorectal cancer, endometrial carcinoma, salivary gland carcinoma, renal cancer, prostate cancer, vulval cancer, thyroid cancer, sarcomas and/or astrocytomas,
  in the case of chronic or acute myeloproliferative disorders such as certain leukaemias,
  in the case of hepatic, lung, prostate, kidney, breast, pancreatic and colorectal gastrointestinal cancers.

Advantageously, the compounds of the invention, and of course pharmaceutical compositions comprising such compounds, can be used in the treatment of pathologies associated with deregulation of protein kinases in the case of diseases, wherein the diseases is selected from the group consisting of liver cancer, pancreatic cancer, lung cancer, breast cancer, prostate cancer, leukemias, renal cancer, endometrial cancer, colorectal cancer, chemoresistant cancers and macular degeneration.

According to another aspect, the invention relates to a medicinal product comprising a compound according to the invention as active principle. Thus, the compounds according to the invention can be used as medicinal products in the treatment of pathologies associated with deregulation of protein kinases:
  in the case of immune disorders, inflammatory diseases, thrombotic diseases, neurodegenerative diseases, bone diseases, macular degeneration, fibrosis, cystogenesis, hyperproliferative diseases,
  in the case of all cancers more particularly liquid tumors such as hematological cancers such as leukemias, chronic or acute myeloproliferative disorders or solid tumors such as squamous cell cancer, small-cell lung cancer, non-small cell lung cancer, gastrointestinal cancers, pancreatic cancer, glial cell tumors such as glioblastoma and neurofibromatosis, cervical cancer, ovarian cancer, liver cancer, bladder cancer, breast cancer, melanoma, colorectal cancer, endometrial carcinoma, salivary gland carcinoma, renal cancer, prostate cancer, vulval cancer, thyroid cancer, sarcomas and/or astrocytomas,
  in the case of chronic or acute myeloproliferative disorders such as certain leukaemias,
  in the case of hepatic, lung, prostate, kidney, breast, pancreatic and colorectal gastrointestinal cancers.

The compositions according to the invention can be used in the treatment of pathologies associated with deregulation of protein kinases:
  in the case of immune disorders, inflammatory diseases, thrombotic diseases, neurodegenerative diseases, bone diseases, macular degeneration, fibrosis, cystogenesis, hyperproliferative diseases,
  in the case of all cancers more particularly liquid tumors such as hematological cancers such as leukemias, chronic or acute myeloproliferative disorders or solid tumors such as squamous cell cancer, small-cell lung cancer, non-small cell lung cancer, gastrointestinal cancers, pancreatic cancer, glial cell tumors such as glioblastoma and neurofibromatosis, cervical cancer, ovarian cancer, liver cancer, bladder cancer, breast cancer, melanoma, colorectal cancer, endometrial carcinoma, salivary gland carcinoma, renal cancer, prostate cancer, vulval cancer, thyroid cancer, sarcomas and/or astrocytomas,
  in the case of chronic or acute myeloproliferative disorders such as certain leukaemias, in the case of hepatic, lung, prostate, kidney, breast, pancreatic and colorectal gastrointestinal cancers.

Moreover, in an advantageous way, the compounds according to the invention can be used for inhibiting cellular proliferation and/or angiogenesis involved in human or animal diseases.

In the same way, the compositions according to the invention can be used for inhibiting cellular proliferation and/or angiogenesis involved in human or animal diseases.

Another aspect of the present invention concerns an in vitro method (in vitro diagnostic device or an imaging tool) for providing information that is essential for the safe and effective use of the compounds according to present invention. As an example, the method will allow predicting whether a patient in need thereof, such as presenting cancer, is likely to respond to at least one of the compounds according to present invention, which method comprises determining the expression level, the gene modifications (amplification, mutation), the activation state or the appearance of a mutated form of the protein of at least one protein kinase in a sample of said patient, wherein said protein kinase is selected from the following list of kinases BRAF, EGFR, FGFR2, KDR, PDGFRA, SRC, ABL, FGFR1, VEGFR1, PDGFRB (PDGFR beta), ABL2, BLK, BMX, BTK, CSK, EPHA1, EPHA2, EPHA4, EPHB2, EPHB4, HER2, ERBB4, FES, FGR, FLT3, FMS, FRK, FYN, HCK, LCK, LYN, MAPK14, ERK2, PKC theta, RET, VEGFR3 and YES, preferably BRAF, EGFR, FGFR2, KDR, PDGFRA and SRC.

The expression levels, gene modifications (amplification, mutation), activation state or appearance of a mutated form of the protein kinase is classically determined by the usually known methods (see for example the in vitro and imaging tools of medical devices approved by the FDA: http://www.fda.gov/MedicalDevices/ProductsandMedicalProcedures/InVitroDiagnostics/ucm 301431.htm) such as real-time PCR, imunohistochemistry, ELISA, fluorescence in situ hybridization (FISH), chromogenic in situ hybridization (CISH).

Another aspect of the present invention concerns an in vitro method for predicting the at least one compound according to the invention to be administered to a patient in need thereof, such as presenting a cancer, characterized in that it comprises the following steps:
  a) putting into contact said compound(s) with a sample of human tissue or cells;
  b) determination of the activity of the compound(s) on the sample via for example IC50 and/or via a compared activity of the protein kinases present, which can for example be chosen from the following list of kinases BRAF, EGFR, EGFR T790M L858R, FGFR2, KDR, PDGFRA, SRC;
  c) optionally conducting the same test as step a) with healthy cells such as hematological cells or stem cells or hepatic cells of said patient to determine the toxicity of the compound according to the present invention to healthy cells (i.e. not presenting any pathological aspects/properties);
  d) selecting the compound according to the present invention presenting the best activity, and/or eventually lowest toxicity, to be administered to the patient in need thereof.

The methods to determine the activity of the protein kinases are classically known (as reported in Rosen et al., J Biol Chem., 15; 261(29), 13754-9. 1986; Ma et al., Expert Opin Drug Discov., 3(6), 607-621, 2008).

FIGURES

EXAMPLES

Figure 1:
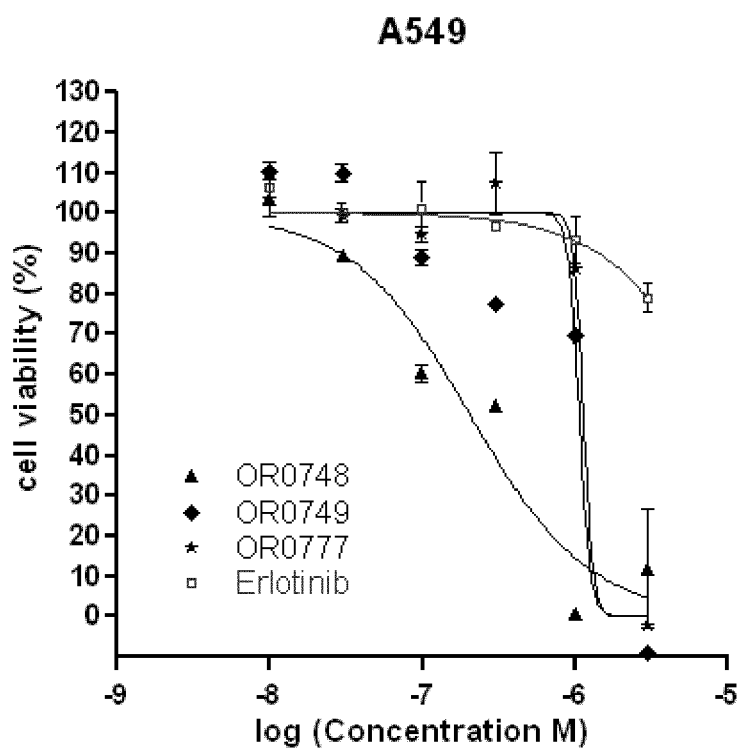
FIG. 1 is a graph representing anti-proliferative activity of some compounds on A549 cells.
Figure 2:
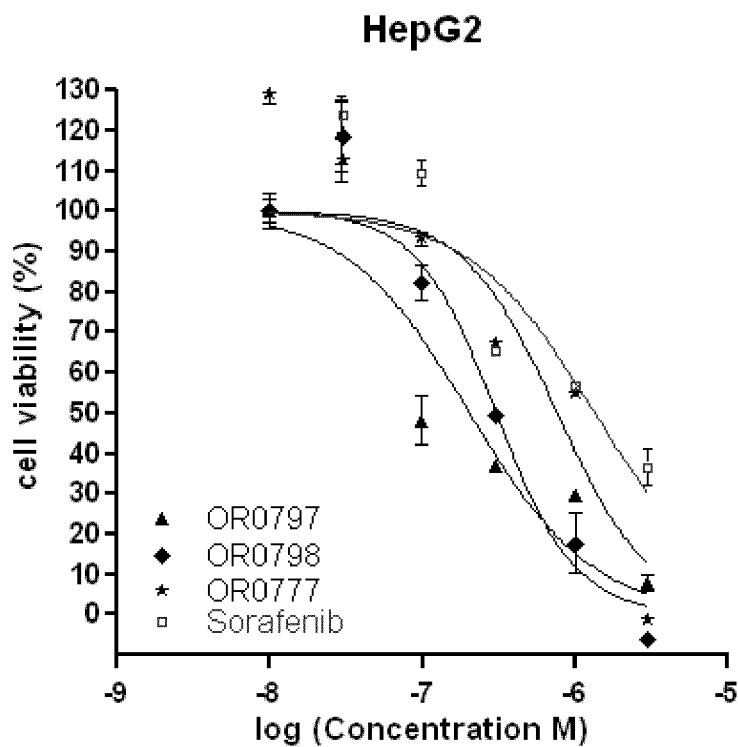
FIG. 2 is a graph representing anti-proliferative activity of some compounds on HepG2 cells.
Figure 3:
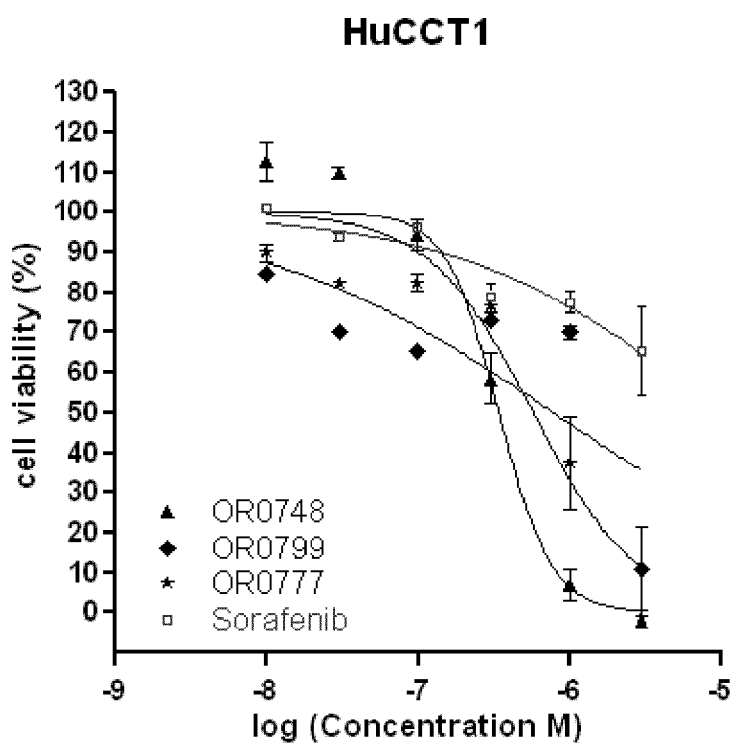
FIG. 3 is a graph representing anti-proliferative activity of some compounds on HuCCT1 cells.
Figure 4:
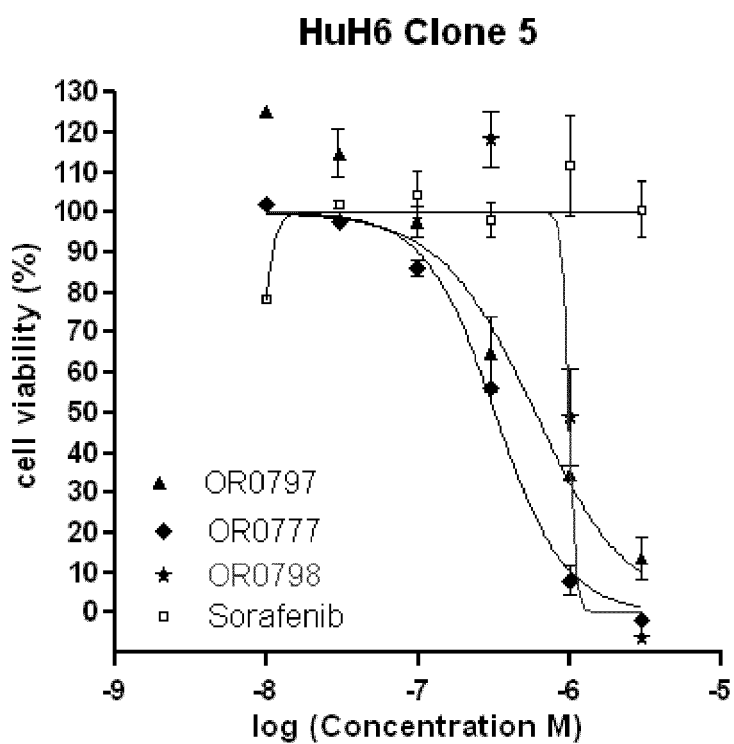
FIG. 4 is a graph representing anti-proliferative activity of some compounds on HuH6 Clone 5 cells.
Figure 5:
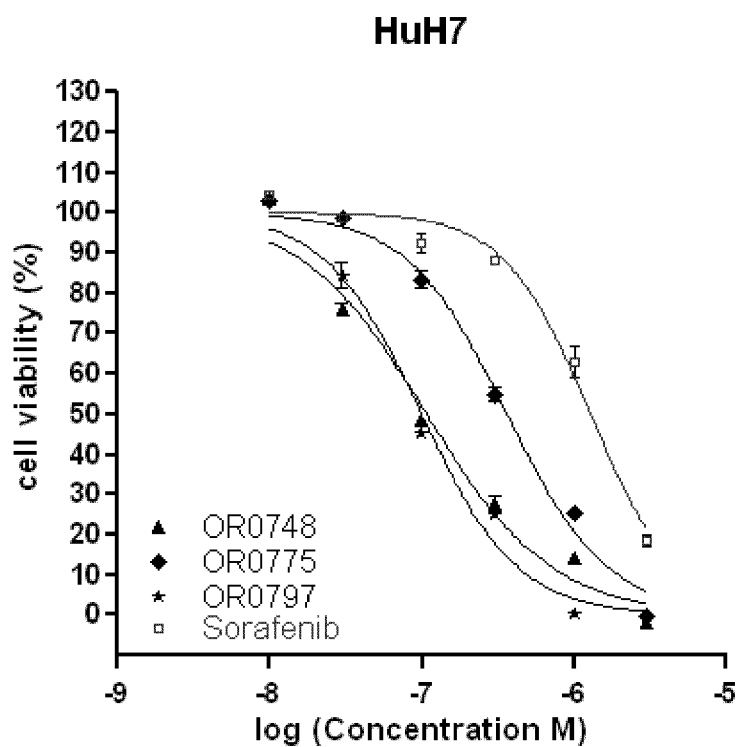
FIG. 5 is a graph representing anti-proliferative activity of some compounds on HuH7 cells.
Figure 6:
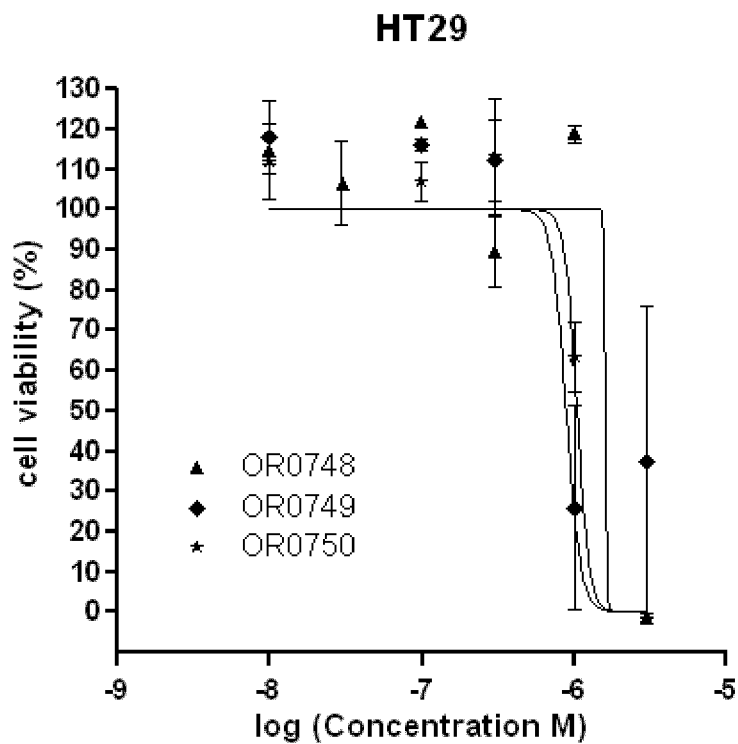
FIG. 6 is a graph representing anti-proliferative activity of some compounds on HT29 cells.
Figure 7:
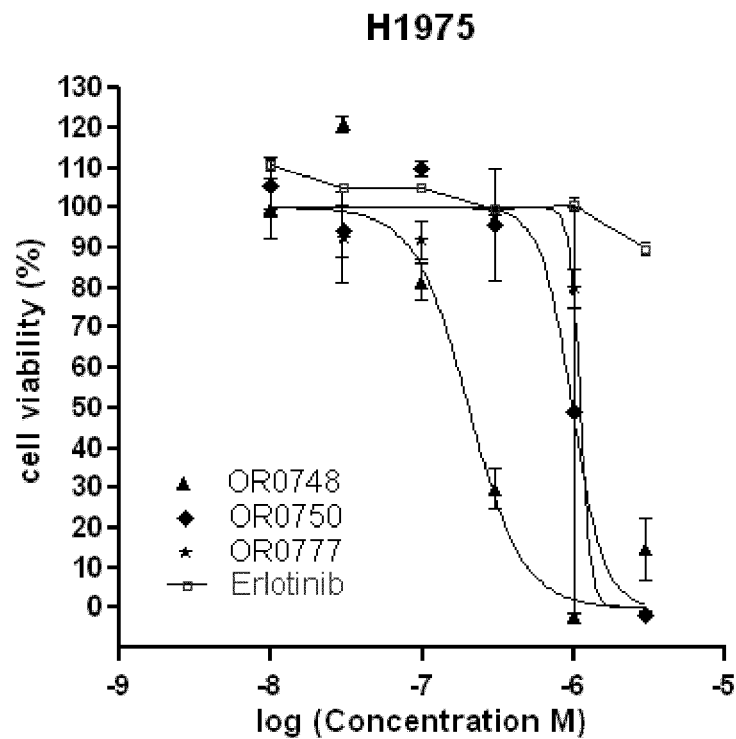
FIG. 7 is a graph representing anti-proliferative activity of some compounds on H1975 cells.
Figure 8:
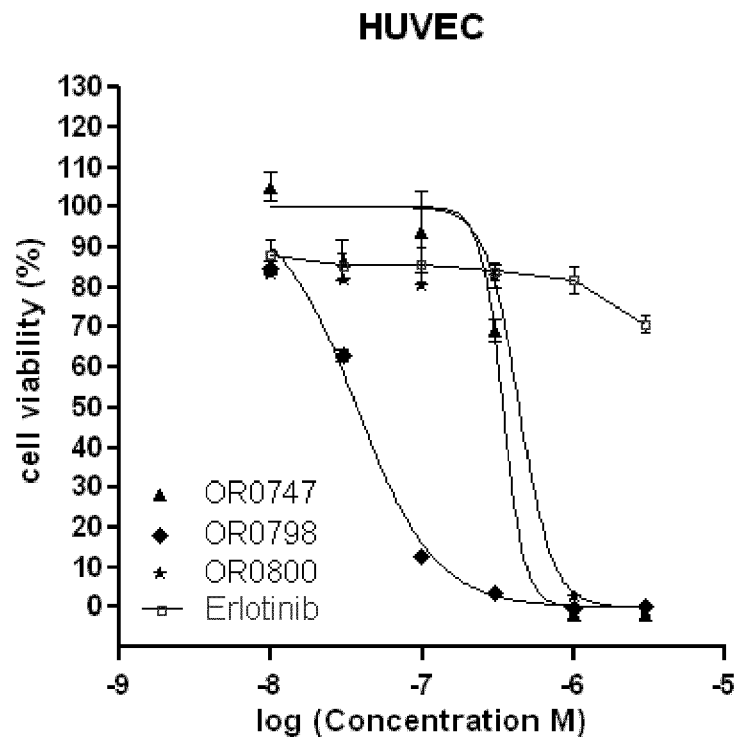
FIG. 8 is a graph representing anti-proliferative activity of some compounds on HUVEC cells.
Figure 9:
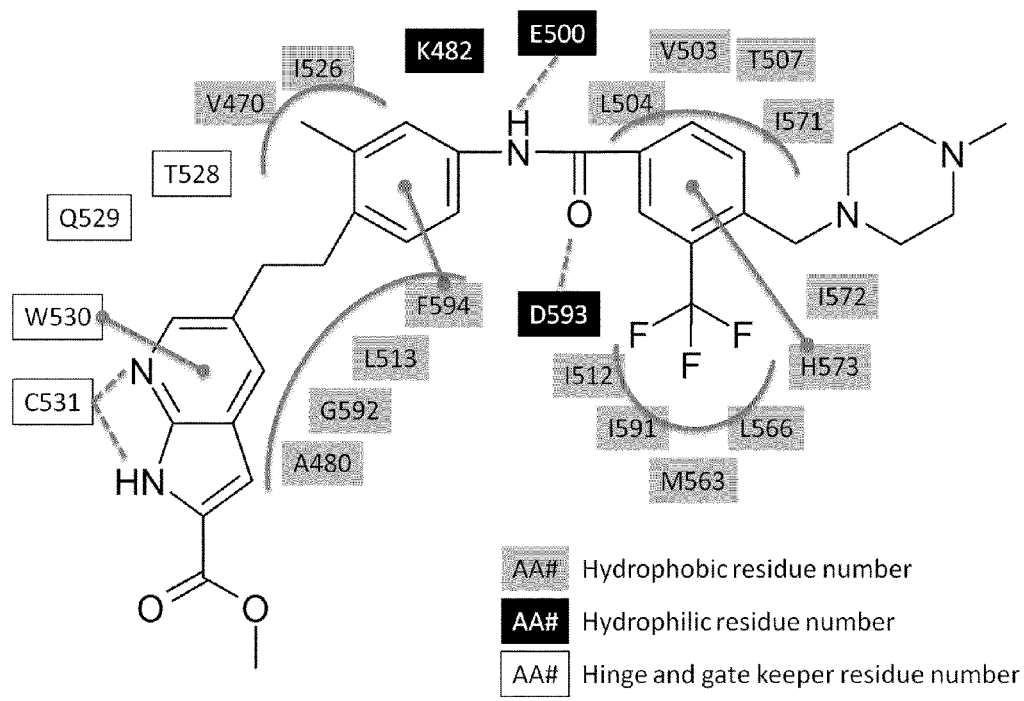
FIG. 9 is a schematic representation of the interactions (hydrophobic contacts, hydrogen bounds and aromatic staking) between compound OR0748 and the amino acids of the kinase domain active site of B-Raf according to the its crystal structure (PDB id=1UWH).
Figure 10:
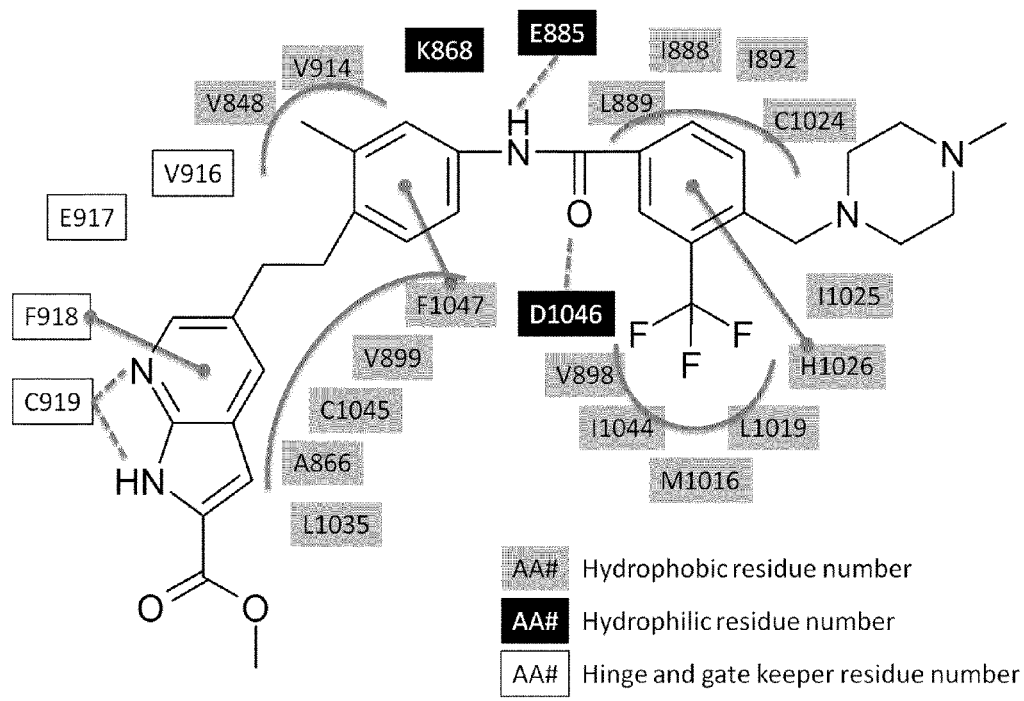
FIG. 10 is a schematic representation of the interactions (hydrophobic contacts, hydrogen bounds and aromatic staking) between compound OR0748 and the amino acids of the kinase domain active site of VEGFR2 according to the its crystal structure (PDB id=4ASD).
Figure 11:
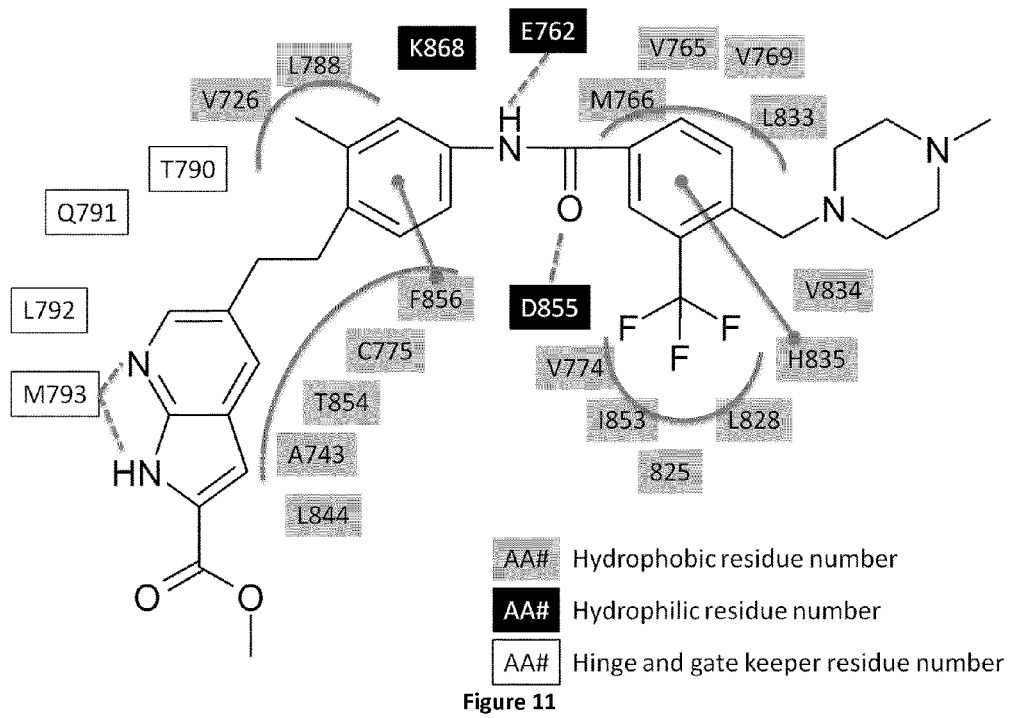
FIG. 11 is a schematic representation of the interactions (hydrophobic contacts, hydrogen bounds and aromatic staking) between compound OR0748 and the amino acids of the kinase domain active site of EGFR according to a homology model of this kinase.
Figure 12:
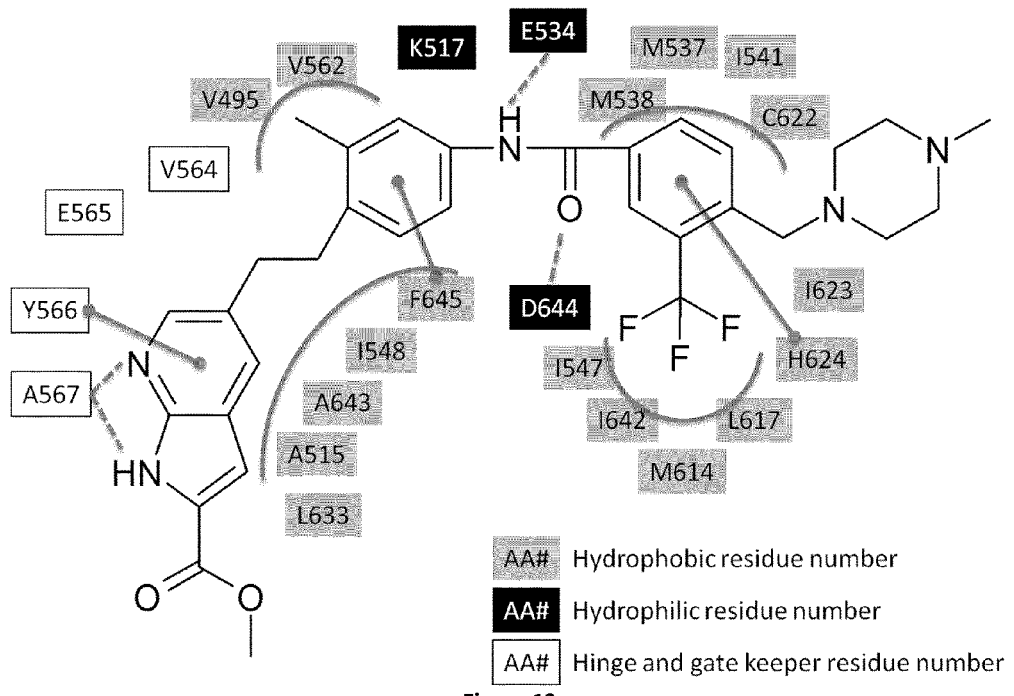
FIG. 12 is a schematic representation of the interactions (hydrophobic contacts, hydrogen bounds and aromatic staking) between compound OR0748 and the amino acids of the kinase domain active site of FGFR2 according to a homology model of this kinase.

The invention will be better understood on reading the following examples.

The compounds of the invention were obtained from 5-cyano-1H-pyrrolo[2,3-b]pyridine-2-carboxylic acid methyl ester, 2-acetyl-1H-pyrrolo[2,3-b]pyridine-5-carbonitrile and 5-amino-1H-pyrrolo[2,3-b]pyridine-2-carboxylic acid methyl ester (commercially available from the company OriBase Pharma—Ref.: AS10-101, AS10-501 and AS10-103 respectively) in multi-stage synthesis, if necessary employing parallel synthesis apparatus ("Synthesis 1", Heidolph). The various synthesis protocols are detailed below together with the physicochemical characteristics of the compounds of the 7-azaindole type obtained.

The syntheses and analyses were carried out in the following conditions:

$^1$H and $^{13}$C nuclear magnetic resonance:

Equipment: Bruker Avance 400 (400 MHz); Bruker Avance 300 (300 MHz); Bruker DPX 200 (200 MHz)

Conditions of use: Room temperature (RT), chemical shifts expressed in parts per million (ppm), coupling constants (J) expressed in Hertz, internal reference trimethylsilane (TMS), multiplicity of the signals indicated by lowercase letters (singlet s, broad singlet bs, doublet d, triplet t, quadruplet q, multiple m), dimethylsulphoxide $d_6$, methanol $d_4$, chloroform $d_1$ as deuterated solvents.

High-performance liquid chromatography (HPLC):

Equipment: Agilent Technology 1260 Infinity

Conditions of use: Zorbax SB-C18, 2.1×50 mm, 1.8 μm; temperature: 30° C., Water/Acetonitrile/Formic acid elution gradient (90%/10%/0.1% to 0%/100%/0.1%)

Mass spectrometry (MS):

Equipment: Quadripole Agilent Technologies 6120

Conditions of use: ElectroSpray (ESI) in positive and/or negative mode.

Weighings:

Equipment: Denver Instrument TP214 (precision 0.1 mg)

Conditions of use: Weighings carried out to the nearest milligram.

Parallel synthesis:

Equipment: Heidolph Synthesis 1 (16 reactors)

Conditions of use: 16 reactions in parallel, room temperature or 4 heating zones, multiple evaporations.

Reactions under pressure:

Equipment: Parr 300 mL autoclave.

Conditions of use: Hydrogenation under 10, 20 or 30 bar of hydrogen.

Syntheses

All the carboxylic acids involved in this synthesis are not commercially available. First is described the synthesis of these needed carboxylic acids:

Synthesis of 4-aminomethyl-benzoic acids

Scheme 25 represents the general method to synthesize the 4-aminomethyl-benzoic acids:

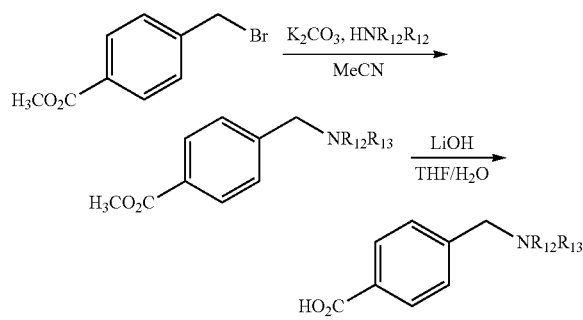

Scheme 25

General Procedure for Nucleophilic Substitution on Bromomethyl:

4-(Bromomethyl)-benzoic acid methyl ester (25 g) in THF (400 mL) with $K_2CO_3$ (1.5 eq) and amine derivative (1 eq) were stirred and heated to reflux under argon overnight. Acetonitrile was evaporated, water (30 mL) was added and the product was extracted with AcOEt. The organic layer was washed with water, dried, filtered and concentrated. Further purification was performed by silica gel chromatography to obtain the expected product.

4-((4-Methylpiperazin-1-yl)methyl)-benzoic acid methyl ester

Yield=60% (15.7 g). ESI-MS: $[M+H]^+$=249.1 Da.

4-((S)-3-Dimethylamino-pyrrolidin-1-ylmethyl)-benzoic acid methyl ester

Yield=40%. ESI-MS: $[M+H]^+$=263.1 Da.

General Procedure for Saponification:

Ester derivative was dissolved in THF (0.8 mol/L) and a water solution of LiOH (3 eq) was added. Mixture was heated to reflux for 4 h. THF was evaporated and impurities were extracted with EtOAc at pH=12. Aqueous layer was saturated with $NaCl_{(s)}$ and acidified until pH=3 with HCl 6 N. Product was extracted with Butan-1-ol. Butan-1-ol was evaporated and the solid obtained was washed with EtOAc to remove salts and impurities. A white solid was obtained.

4-((4-methylpiperazin-1-yl)methyl)-benzoic acid

Yield quantitative. ESI-MS: $[M+H]^+$=235.1 Da.

4-((S)-3-Dimethylamino-pyrrolidin-1-ylmethyl)-benzoic acid

Yield quantitative. ESI-MS: $[M+H]^+$=249.2 Da.

Synthesis of 4-aminomethyl-3-trifluoromethyl-benzoic acids

Scheme 26 represents the general method to synthesize the 4-aminomethyl-3-trifluoromethyl-benzoic acids:

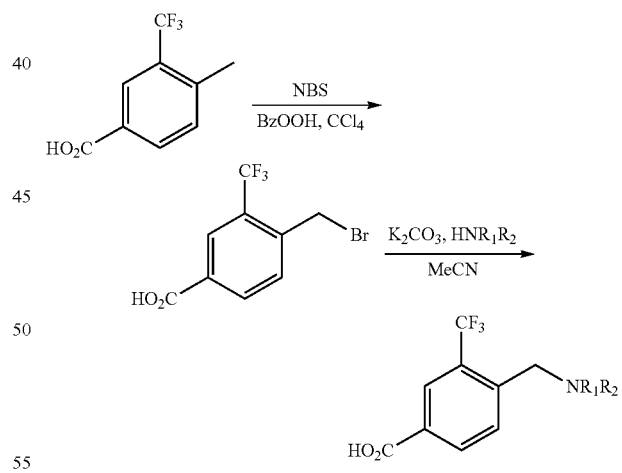

Scheme 26

Synthesis of 4-(bromomethyl)-3-(trifluoromethyl) benzoic acid

Methyl 4-methyl-3-(trifluoromethyl)benzoate (4.0 g, 18.3 mmol) in $CCl_4$ (40 mL) with NBS (3.9 g, 22 mmol) and benzoylperoxide with 25% of water (0.55 g, 1.7 mmol) were stirred and heated to reflux for 6 h. Solvent was evaporated, a water solution of $K_2CO_3$ was added and product is extracted with EtOAc to obtain a pale yellow solid (7.64 g, 25.7 mmol). Yield=140% (crude).

General Procedure for Nucleophilic Substitution on Bromomethyl:

4-(Bromomethyl)-3-(trifluoromethyl)benzoic acid (200 mg) in acetonitrile (5 mL) with $K_2CO_3$ (1.5 eq) and amine derivative (1.05 eq) were stirred and heated to reflux under argon overnight. Acetonitrile was evaporated, water (30 mL) was added and impurities were extracted with EtOAc at pH=12. Aqueous layer was saturated with $NaCl_{(s)}$ and acidified until pH=3 with HCl 6 N. Product was extracted with Butan-1-ol. Butan-1-ol was evaporated and the solid obtained was washed with EtOAc to remove salts and impurities. A white solid was obtained.

4-((4-Methylpiperazin-1-yl)methyl)-3-(trifluoromethyl)benzoic acid

Yield=89%. $^1$H NMR (300 MHz, DMSO-d6) δ 10.44 (m, 1H), 8.19 (s, 1H), 8.18 (m, 1H), 7.93 (m, 1H), 3.79 (s, 2H), 2.75 (s, 3H). ESI-MS: $[M+H]^{30}$ =303 Da.

4-(3-Dimethylamino-pyrrolidin-1-ylmethyl)-3-trifluoromethyl-benzoic acid

Yield: 83%. HPLC: 92% ESI-MS: $[M+H]^+$=317 Da.

Synthesis of 4-aminomethyl-3-fluoromethyl-benzoic acids

Scheme 27

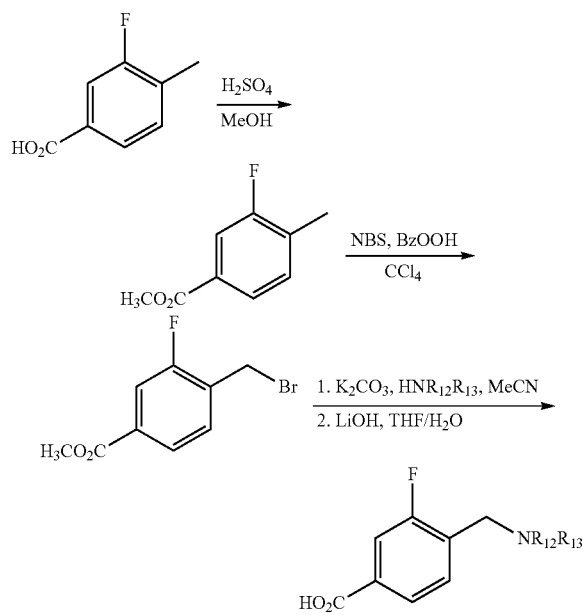

General Procedure for Esterification:

4-Methyl-3-fluoro benzoic acid (24 mmol) in methanol (50 mL) with $H_2SO_4$ (0.260 mL, 4.8 mmol) are stirred and heated to reflux for one night. Methanol is evaporated and product is extracted at pH=7 with EtOAc.

4-Methyl-3-fluoro-benzoic acid methyl ester

Yield=83% (4.0 g), HPLC: 98%, ESI-MS: $[M+H]^+$=169 Da.

General Procedure for Bromination:

4-Methyl-3-fluoro benzoic acid methyl ester (18.3 mmol) in $CCl_4$ (40 mL) with NBS (3.9 g, 22 mmol) and benzoylperoxide with 25% of water (0.55 g, 1.7 mmole) are stirred and heated to reflux for 6 h. Solvent is evaporated, a water solution of $K_2CO_3$ is added and product is extracted with EtOAc to obtain a pale yellow solid.

4-(Bromomethyl)-3-fluoro benzoic acid methyl ester

Yield=quant (5.9 g), ESI-MS: $[M+H]^+$=247 Da.

General Procedure for Nucleophilic Substitution on Bromomethyl Derivatives:

4-(Bromomethyl)-3-fluoro benzoic acid methyl ester (200 mg) in acetonitrile (5 mL) with $K_2CO_3$ (1.5 eq) and amine derivative (1.05 eq) were stirred and heated to reflux under argon overnight. Acetonitrile was evaporated, water (30 mL) was added and the product was extracted with AcOEt. The organic layer was washed with water, dried, filtered and concentrated. Further purification was performed by silica gel chromatography to obtain the expected product.

3-Fluoro-4-(4-methylpiperazin-1-ylmethyl)-benzoic acid methyl ester

Yield=49% (1.48 g). HPLC: 88%, ESI-MS: $[M+H]^+$=267 Da.

4-(3-Dimethylamino-pyrrolidin-1-ylmethyl)-3-fluoro-benzoic acid methyl ester

Yield: 60% (2 g). HPLC: 85% ESI-MS: $[M+H]^+$=281 Da.

General Procedure for Saponification:

Ester derivative was dissolved in THF (0.8 mol/L) and a water solution of LiOH (3 eq) was added. Mixture was heated to reflux for 4 h. THF was evaporated and impurities were extracted with EtOAc at pH=12. Aqueous layer was saturated with $NaCl_{(s)}$ and acidified until pH=3 with HCl 6 N. Product was extracted with Butan-1-ol. Butan-1-ol was evaporated and the solid obtained was washed with EtOAc to remove salts and impurities. A white solid was obtained.

3-Fluoro-4-(4-methylpiperazin-1-ylmethyl)-benzoic acid

Yield=65% (0.91 g). HPLC: >99%, ESI-MS: $[M+H]^+$ =253 Da.

Synthesis of 5-trifluoromethyl-benzoic acid 3 Substituted Derivatives

Scheme 28 represents the general method to synthesize the 5-trifluoromethyl-benzoic acid 3 substituted derivatives.

Scheme 28

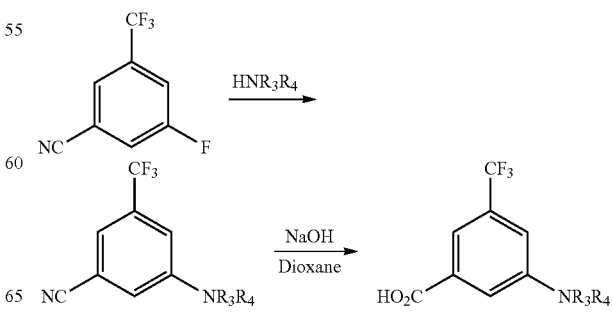

General Procedure for Nucleophilic Substitution:

A solution of 3-fluoro-5-trifluoromethyl-benzonitrile (1 eq) and the corresponding amine (3 eq) in DMA was stirred at 145° C. during 3 h. NaCl$_{(aq)}$ was added. The product was taken off into ethyl acetate. The organic layer was washed two times with water then dried over Na$_2$SO$_4$ and evaporated under reduced pressure to give the intermediate compounds.

3-(4-Methyl-imidazol-1-yl)-5-trifluoromethyl-benzonitrile

Yield: 74%. HPLC: 100% ESI-MS: [M+H]$^+$=252 Da.

3-(4-Methyl-piperazin-1-yl)-5-trifluoromethyl-benzonitrile

Yield: quantitative. HPLC: 94% ESI-MS: [M+H]$^+$=270 Da.

General Procedure for Hydrolysis of Nitrile:

At a solution of nitrile derivative in dioxane (0.13M) was added NaOH (10 eq, 1 g/L) in H$_2$O. The mixture was heat at reflux overnight. After evaporation of the dioxane, the aqueous layer was washed with AcOEt, then acidified with HCl 2N and extract with AcOEt. The organic layer was dried over Na$_2$SO$_4$ filtered and concentrated.

3-(4-Methyl-imidazol-1-yl)-5-trifluoromethyl-benzoic acid

Yield: 99%. HPLC: 100%. ESI-MS: [M+H]$^+$=271 Da.

3-(4-Methyl-piperazin-1-yl)-5-trifluoromethyl-benzoic acid

Yield: 60%. HPLC: 100%. ESI-MS: [M+H]$^+$=289 Da.

Example A

Synthesis of 5-[(5-benzoylamino-2-methyl-benzoylamino)-methyl]-1H-pyrrolo[2,3-b]pyridine-2-carboxylic acid methyl esters Scheme 29 represents a general method of synthesis of 5-[(5-Benzoylamino-2-methyl-benzoylamino)-methyl]-1H-pyrrolo[2,3-b]pyridine-2-carboxylic acid methyl ester.

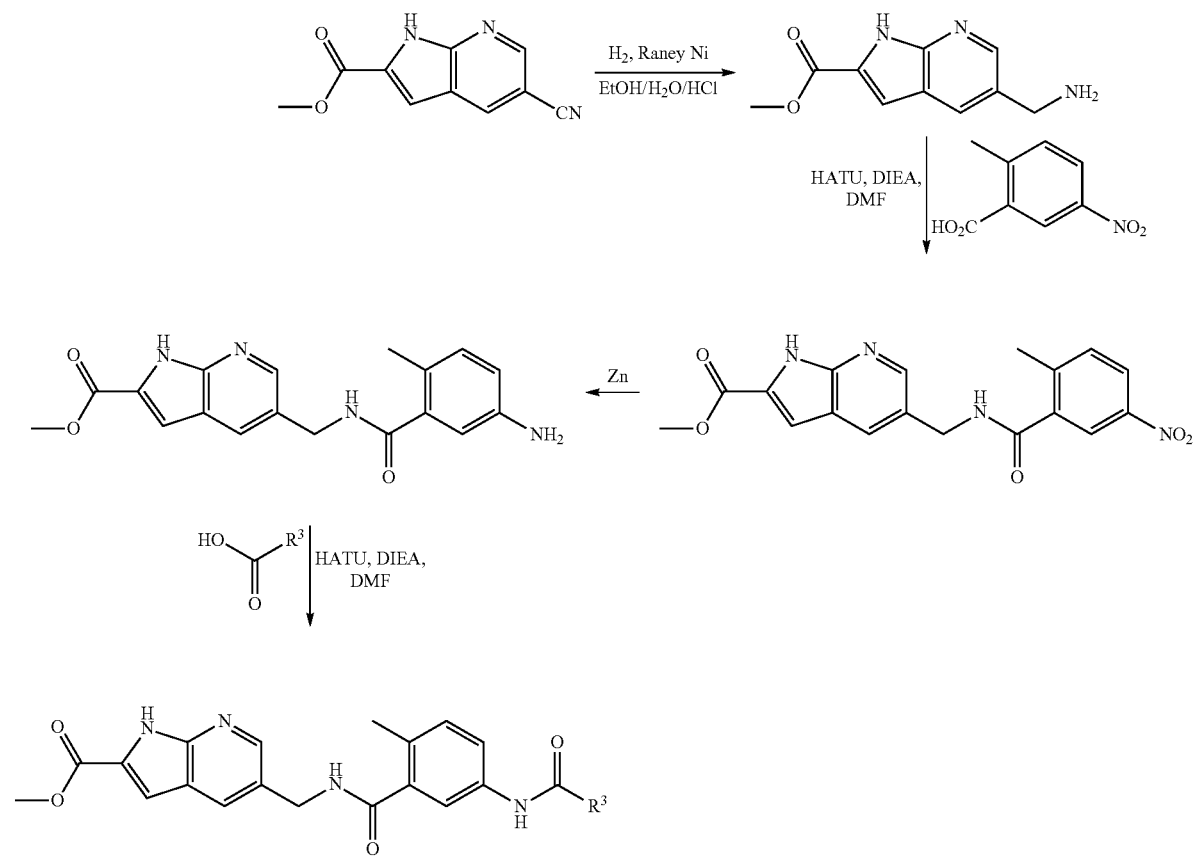

Scheme 29 - General synthesis scheme of example A

Step 1: Protocol for the Preparation of 5-aminomethyl-1H-pyrrolo[2,3-b]pyridine-2-carboxylic acid methyl ester 5-Cyano-1H-pyrrolo[2,3-b]pyridine-2-carboxylic acid methyl ester (1.8 g, 8.9 mmol) and 20 mL of Raney nickel in H$_2$O were put in suspension in 360 mL of a mixture EtOH/H$_2$O (7/3) with 10% of HCl 12N under H$_2$ at atmospheric pressure and stirred overnight. The mixture was filtered on a bed of celite with MeOH to eliminate Raney nickel. The filtrate was retrieved and concentrated under reduced pressure. The crude was purified on reverse phase column (H$_2$O/MeCN).

Yield=52% (960 mg). $^1$H NMR (300 MHz, D$_2$O): δ 8.35 (d, J=2.1, 1H), 8.18 (d, J=2.1, 1H), 7.16 (s, 1H), 4.28 (s, 2H), 3.93 (s, 3H). ESI-MS: m/z 206 ([M+H]$^+$). HPLC purity: 81%.

Step 2: Protocol for the Preparation of 5-[(2-methyl-5-nitro-benzoylamino)-methyl]-1H-pyrrolo[2,3-b]pyridine-2-carboxylic acid methyl ester To a solution of 2-methyl-5-nitro-benzoic acid (1 eq) in dry DMF (0.1-0.2 M) was added DIEA (5 eq) and HATU (1.1 eq). The mixture was stirred under Argon for 30 min and 5-aminomethyl-1H-pyrrolo[2,3-b]pyridine-2-carboxylic acid methyl ester (1 eq) was added and the mixture is stirred for 5 h. DMF was removed under reduced pressure. The crude was washed by H$_2$O and the precipitate was filtered.

Yield=81%. $^1$H NMR (300 MHz, DMSO): δ 12.66-12.36 (m, 1H), 9.14 (s, 1H), 8.46 (s, 1H), 8.19 (s, 1H), 8.17 (s, 1H), 8.09 (s, 1H), 7.55 (d, J=8.3, 1H), 7.20 (s, 1H), 4.58 (s, 2H), 3.88 (s, 3H), 2.44 (s, 3H). ESI-MS: m/z 369 ([M+H]$^+$). HPLC purity: 95%.

Step 3: Protocol for the Preparation of 5-[(5-amino-2-methyl-benzoylamino)-methyl]-1H-pyrrolo[2,3-b]pyridine-2-carboxylic acid methyl ester 5-[(2-Methyl-5-nitro-benzoylamino)-methyl]-1H-pyrrolo[2,3-b]pyridine-2-carboxylic acid methyl ester (580 mgl) was dissolved in a AcOH/AcOEt mixture (9 ml/18 ml) and zinc powder (15 eq) was added. The mixture was exposed to ultrasound at RT for 1 hour. The crude mixture was filtered on celite and washed with AcOEt. The filtrate was concentrated to afford a yellowish precipitate which gave a white solid (515 mg) when triturated in a NaHCO$_3$ solution.

Yield=96%. ESI-MS: m/z 340 ([M+H]$^+$). HPLC purity: 87%.

Step 4: General Protocol for the Preparation of 5-[(5-benzoylamino-2-methyl-benzoylamino)-methyl]-1H-pyrrolo[2,3-b]pyridine-2-carboxylic acid methyl esters Acid derivative was dissolved in anhydrous DMF (0.06 mol/L) with DIEA (5 eq) and HATU (2 eq). After 15 min, 5-[(5-amino-2-methyl-benzoylamino)-methyl]-1H-pyrrolo[2,3-b]pyridine-2-carboxylic acid methyl ester was slowly added and mixture was stirred for 12 h at RT. DMF was evaporated and NaHCO$_{3(aq)}$ was added. Product was extracted with EtOAc, dried, filtered and evaporated to obtain a dark mixture. After purification by washing with MeOH or EtOAc or by silica column, expected product was obtained.

Table 1 shows the compounds synthesized according to the synthesis Scheme 29 described above.

TABLE 1

| | Compounds obtained by example A | |
|---|---|---|
| Example No. | Used reagents | Synthesized inhibitors (mass and analytical data) |
| OR1078 | [structure: HO-C(=O)-C6H4-N(CH3)2] | 5-{[5-(4-Dimethylamino-benzoylamino)-2-methyl-benzoylamino]-methyl}-1H-pyrrolo[2,3-b]pyridine-2-carboxylic acid methyl ester [structure] Yield: 4% $^1$H NMR (400 MHz, DMSO) δ 12.49 (s, 1H), 9.87 (s, 1H), 8.84 (t, J = 5.7, 1H), 8.45 (s, 1H), 8.07 (s, 1H), 7.85 (d, J = 8.8, 2H), 7.80-7.73 (m, 2H), 7.22-7.13 (m, 2H), 6.74 (d, J = 8.8, 2H), 4.53 (d, J = 5.7, 2H), 3.88 (s, 3H), 2.99 (s, 6H), 2.26 (s, 3H) HPLC: 93%; MS: 486 (M + 1) |

TABLE 1-continued

Compounds obtained by example A

| Example No. | Used reagents | Synthesized inhibitors (mass and analytical data) |
|---|---|---|
| OR1081 | 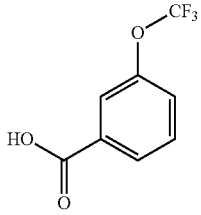 [SMILES: O=C(O)c1cccc(OC(F)(F)F)c1] | 5-{[2-Methyl-5-(3-trifluoromethoxy-benzoylamino)-benzoylamino]-methyl}-1H-pyrrolo[2,3-b]pyridine-2-carboxylic acid methyl ester 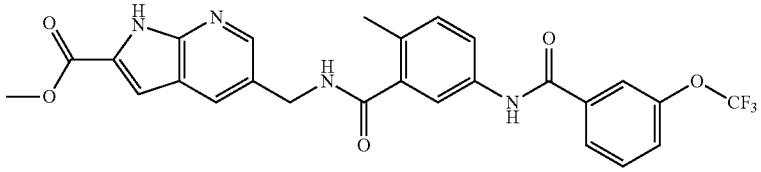 [SMILES: COC(=O)c1cc2cc(CNC(=O)c3cc(NC(=O)c4cccc(OC(F)(F)F)c4)ccc3C)cnc2[nH]1]<br>Yield: 35%<br>$^1$H NMR (400 MHz, DMSO) δ 12.49 (s, 1H), 10.39 (s, 1H), 8.87 (t, J = 5.7, 1H), 8.45 (s, 1H), 8.07 (s, 1H), 8.00 (d, J = 7.8, 1H), 7.90 (s, 1H), 7.82-7.72 (m, 2H), 7.68 (t, J = 7.8, 1H), 7.61 (d, J = 8.2, 1H), 7.23 (d, J = 8.2, 1H), 7.19 (s, 1H), 4.54 (d, J = 5.7, 2H), 3.88 (s, 3H), 2.28 (s, 3H)<br>HPLC: 93%; MS: 527 (M + 1) |
| OR0730 | 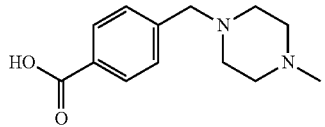 | 5-({2-Methyl-5-[4-(4-methyl-piperazin-1-ylmethyl)-benzoylamino]-benzoylamino}-methyl)-1H-pyrrolo[2,3-b]pyridine-2-carboxylic acid methyl ester 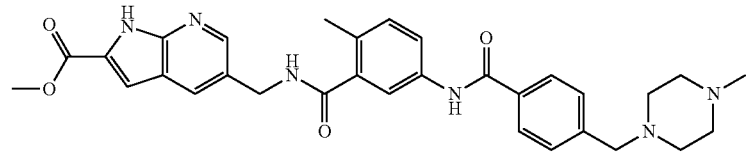<br>Yield: 7.4%<br>$^1$H NMR (300 MHz, DMSO) δ 10.22 (s, 1H), 8.80 (t, J = 6.2, 1H), 8.34 (s, 1H), 7.96 (s, 1H), 7.89 (d, J = 8.2, 2H), 7.79-7.72 (m, 2H), 7.42 (d, J = 8.2, 2H), 7.20 (d, J = 8.7, 1H), 7.07 (s, 1H), 4.50 (d, J = 6.2, 2H), 3.83 (s, 3H), 3.51 (s, 2H), 2.41-2.29 (m, 8H), 2.27 (s, 3H), 2.14 (s, 3H)<br>HPLC: 98%; MS: 555 (M + 1) |
| OR0728 | 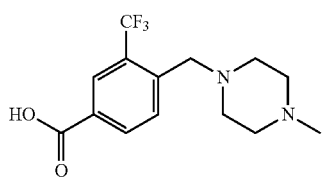 | 5-({2-Methyl-5-[4-(4-methyl-piperazin-1-ylmethyl)-3-trifluoromethyl-benzoylamino]-benzoylamino}-methyl)-1H-pyrrolo[2,3-b]pyridine-2-carboxylic acid methyl ester 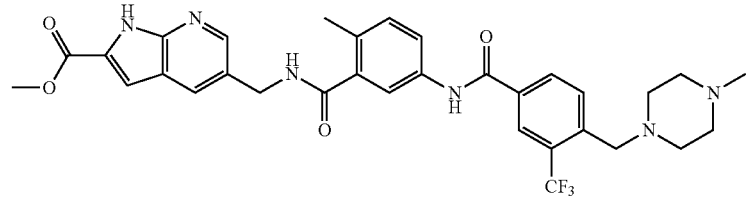<br>Yield: 6%<br>$^1$H NMR (400 MHz, DMSO) δ 12.43, (s, 1H), 10.48 (s, 1H), 8.89 (t, J = 4.8, 1H), 8.44 (s, 1H), 8.30-8.19 (m, 2H), 8.06 (s, 1H), 7.93 (d, J = 8.8, 1H), 7.79 (d, J = 7.6, 1H), 7.73 (s, 1H), 7.23 (d, J = 7.6, 1H), 7.18 (s, 1H), 4.54 (d, J = 4.8, 2H), 3.87 (s, 3H), 3.67 (s, 2H), 2.41 (bs, 4H), 2.35 (bs, 4H), 2.28 (s, 3H), 2.16 (s, 3H)<br>HPLC: 94%; MS: 623 (M + 1) |

TABLE 1-continued

Compounds obtained by example A

| Example No. | Used reagents | Synthesized inhibitors (mass and analytical data) |
|---|---|---|
| OR0726 | ![reagent structure with CF3, HO, N, dimethylamine pyrrolidine] | 5-({5-[4-(3-Dimethylamino-pyrrolidin-1-ylmethyl)-3-trifluoromethyl-benzoylamino]-2-methyl-benzoylamino}-methyl)-1H-pyrrolo[2,3-b]pyridine-2-carboxylic acid methyl ester<br><br>![product structure]<br><br>Yield: 17%<br>$^1$H NMR (300 MHz, DMSO) δ 12.50 (s, 1H), 10.45 (s, 1H), 8.88 (t, J = 5.8, 1H), 8.45 (d, J = 1.6, 1H), 8.26-8.18 (m, 2H), 8.07 (s, 1H), 7.89 (d, J = 7.8, 1H), 7.82-7.70 (m, 2H), 7.23 (d, 1H), 7.19 (d, J = 1.9, 1H), 4.54 (d, J = 5.9, 2H), 3.88 (s, 3H), 3.79 (d, J = 5.3, 2H), 2.75-2.50 (m, 5H), 2.33-2.17 (m, 6H), 2.04-1.87 (m, 1H), 1.83-1.64 (m, 1H)<br>HPLC: 99%; MS: 664 (M + 1) |

Example B

Synthesis of 5-(2-{5-benzoylamino-2-methyl-phenyl}-ethyl)-1H-pyrrolo[2,3-b]pyridine-2-carboxylic acid methyl esters Scheme 30 represents a general method of synthesis of 5-(2-{5-benzoylamino-2-methyl-phenyl}-ethyl)-1H-pyrrolo[2,3-b]pyridine-2-carboxylic acid methyl esters.

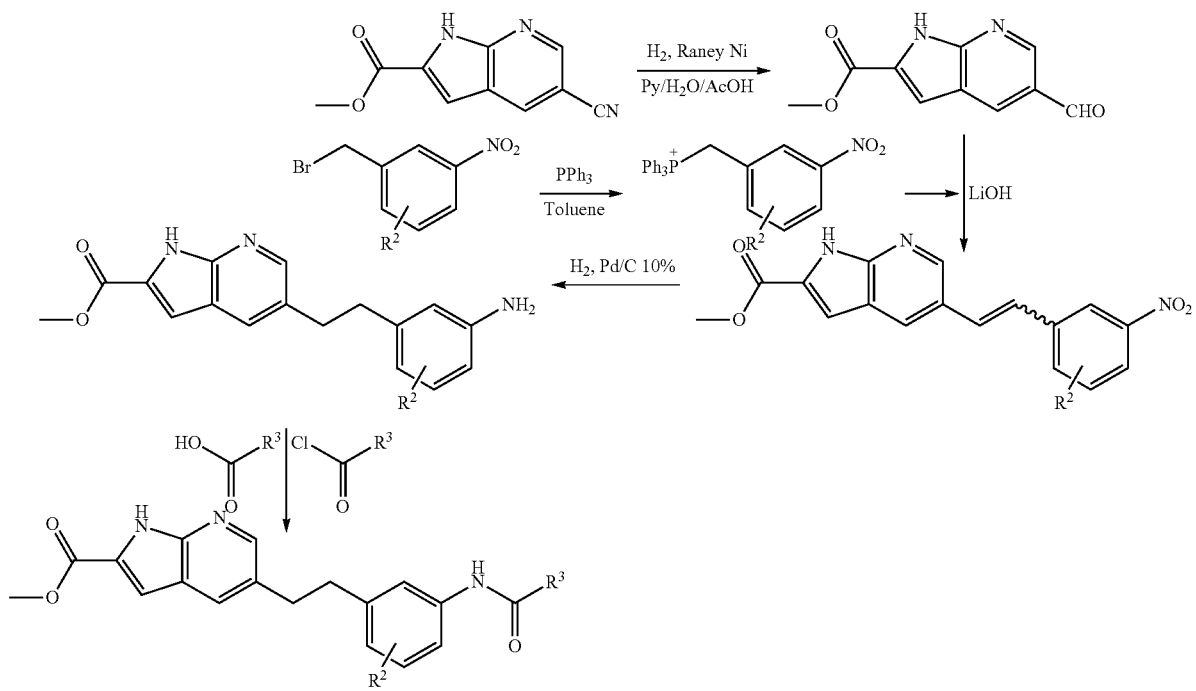

Scheme 30 - General synthesis scheme of example B

Step 1: Protocol for the Preparation of 5-formyl-1H-pyrrolo[2,3-b]pyridine-2-carboxylic acid methyl ester 5-Cyano-1H-pyrrolo[2,3-b]pyridine-2-carboxylic acid methyl ester (200 mg, 1 mmol) in solution in a mixture of pyridine/$H_2O$/AcOH (2/1/1, 150 mL) and 0.5 mL of Raney Nickel in $H_2O$ were stirred under a 10 bar pressure of $H_2$ overnight. The mixture was filtered on celite and washed with MeOH. The filtrate was concentrated. The crude was washed by a saturated solution of $NaHCO_3$ and extracted with AcOEt to give 137 mg of a brown solid.

Yield=67%. $^1$H NMR (300 MHz, DMSO) δ 13.08 (bs, 1H), 10.11 (s, 1H), 8.93 (d, J=1.7, 1H), 8.67 (d, J=1.7, 1H), 7.40 (s, 1H), 3.90 (s, 3H). ESI-MS: m/z 205 ([M+H]$^+$). HPLC purity: 95.5%.

Step 2: General Protocol for the Preparation of nitro-benzyl-triphenyl-phosphonium derivatives 2-Bromomethyl-4-nitro-benzene derivatives (320 mg) was added in a dried flask with triphenylphosphine (1 eq) in anhydrous toluene (15 mL) and the reaction was stirred overnight at reflux. The crude was filtered and washed with toluene and $Et_2O$ to obtain a white powder.

(3-Nitro-benzyl)-triphenyl-phosphonium

Yield=quant. ESI-MS: m/z 398 ([M]$^+$).

(2-Methyl-5-nitro-benzyl)-triphenyl-phosphonium

Yield=95%. HPLC purity: 99%. $^1$H NMR (300 MHz, DMSO) δ 8.09 (d, J=8.4, 1H), 7.94 (t, J=7.2, 3H), 7.84-7.62 (m, 14H), 7.42 (d, J=8.4, 1H), 5.23 (d, J=15.4, 2H), 1.80 (s, 3H). ESI-MS: m/z 412 ([M]$^+$).

(2-Chloro-5-nitro-benzyl)-triphenyl-phosphonium

Yield=quant. HPLC purity: 97%. ESI-MS: m/z 433 ([M]$^+$).

(4-methyl-3-nitro-benzyl)-triphenyl-phosphonium

Yield=quant. HPLC purity: 99%. ESI-MS: m/z 412 ([M]$^+$).

Step 3: General Protocol for the Preparation of 5-[-2-(5-nitro-phenyl)-vinyl]-1H-pyrrolo[2,3-b]pyridine-2-carboxylic acid methyl ester Derivatives 5-Formyl-1H-pyrrolo[2,3-b]pyridine-2-carboxylic acid methyl ester (285 mg, 1.4 mmol) was added in a dried flask with (5-nitro-benzyl)-triphenyl-phosphonium derivatives (1 eq), LiOH (2 eq) in anhydrous MeOH (30 mL) and the reaction was stirred at reflux overnight. The crude mixture was basified with $NH_4Cl$ to pH 7 and the precipitate was filtered and washed with $Et_2O$ to obtain a grey powder.

5-[2-(3-Nitro-phenyl)-vinyl]-1H-pyrrolo[2,3-b]pyridine-2-carboxylic acid methyl ester Yield=87%. HPLC purity: 79%. ESI-MS: m/z 324 ([M+H]$^+$).

5-[-2-(2-Methyl-5-nitro-phenyl)-vinyl]-1H-pyrrolo[2,3-b]pyridine-2-carboxylic acid methyl ester Yield=42%. HPLC purity: 95%. $^1$H NMR (400 MHz, DMSO) δ 12.54 (s, 1H), 8.50 (s, 1H), 8.12 (s, 1H), 8.05 (d, J=7.7, 2H), 7.85 (d, J=7.7, 2H), 7.08 (s, 1H), 6.97 (d, J=12.1, 1H), 6.78 (d, J=12.1, 1H), 3.86 (s, 3H), 2.36 (s, 4H).ESI-MS: m/z 338 ([M+H]$^+$).

5-[-2-(2-Chloro-5-nitro-phenyl)-vinyl]-1H-pyrrolo[2,3-b]pyridine-2-carboxylic acid methyl ester Yield=70%. HPLC purity: 91%. ESI-MS: m/z 358 ([M+H]$^+$).

5-[-2-(4-Methyl-3-nitro-phenyl)-vinyl]-1H-pyrrolo[2,3-b]pyridine-2-carboxylic acid methyl ester Yield=58%. HPLC purity: 67%. ESI-MS: m/z 338 ([M+H]$^+$).

Step 4: General Protocol for the Preparation of 5-[2-(5-amino-phenyl)-ethyl]-1H-pyrrolo[2,3-b]pyridine-2-carboxylic acid methyl ester derivatives 5-[-2-(5-Nitro-phenyl)-vinyl]-1H-pyrrolo[2,3-b]pyridine-2-carboxylic acid methyl ester derivatives (1.3 mmol) was dissolved in DMF, introduced in a reactor with 10% Pd/C and stirred for 16 hours under 10 bar of hydrogen. Reaction mixture was then filtered on celite and concentrated to afford the desired compound.

5-[2-(3-Amino-phenyl)-ethyl]-1H-pyrrolo[2,3-b]pyridine-2-carboxylic acid methyl ester Yield=81%. HPLC purity: 70%. ESI-MS: m/z 296 ([M+H]$^+$).

5-[2-(5-Amino-2-methyl-phenyl)-ethyl]-1H-pyrrolo[2,3-b]pyridine-2-carboxylic acid methyl ester Yield=26%. HPLC purity: 98%. ESI-MS: m/z 310 ([M+H]$^+$).

5-[2-(5-Amino-2-chloro-phenyl)-ethyl]-1H-pyrrolo[2,3-b]pyridine-2-carboxylic acid methyl ester Yield=98%. HPLC purity: 78%. ESI-MS: m/z 330 ([M+H]$^+$).

5-[2-(3-Amino-4-methyl-phenyl)-ethyl]-1H-pyrrolo[2,3-b]pyridine-2-carboxylic acid methyl ester Yield=99%. ESI-MS: m/z 310 ([M+H]$^+$).

Step 5: General Protocol for the Preparation of 5-[(5-benzoylamino-phenyl)-ethyl]-1H-pyrrolo[2,3-b]pyridine-2-carboxylic acid methyl esters Option1: Synthesis of 5-[(5-benzoylamino-phenyl)-ethyl]-1H-pyrrolo[2,3-b]pyridine-2-carboxylic acid methyl esters by Reaction of Acyl Chloride 55 μL of trimethylamine (3 eq) and 1.5 eq of acyl chloride are added to a solution of 5-[2-(5-amino-phenyl)-ethyl]-1H-pyrrolo[2,3-b]pyridine-2-carboxylic acid methyl ester derivative (40 mg) in anhydrous DMF. The reaction mixture is stirred overnight at RT. DMF is evaporated; the solid is taken off into ethyl acetate. The organic layer is washed with saturated $NaHCO_3$ solution, dried over $Na_2SO_4$ and evaporated under reduce pressure to give a yellow solid.

Table 2 shows the compound synthesized according to the synthesis Scheme 30 described above.

TABLE 2

Compounds obtained by example B with acyl chlorides

| Example No. | Used reagents | Synthesized inhibitors (mass and analytical data) |
|---|---|---|
| OR1064 | 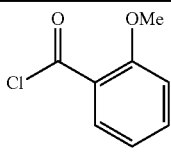 | 5-{2-[2-Chloro-5-(2-methoxy-benzoylamino)-phenyl]-ethyl}-1H-pyrrolo[2,3-b]pyridine-2-carboxylic acid methyl ester<br>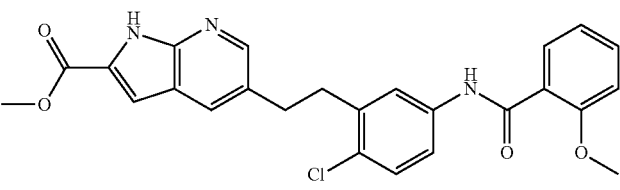<br>Yield: 8%<br>$^1$H NMR (400 MHz, DMSO) δ 10.17 (s, 1H), 8.31 (s, 1H), 7.96 (s, 1H), 7.76 (s, 1H), 7.66-7.57 (m, 2H), 7.51 (t, J = 7.6, 1H), 7.38 (d, J = 8.6, 1H), 7.18 (d, J = 8.6, 1H), 7.12 (s, 1H), 7.06 (t, J = 7.6, 1H), 3.88 (s, 3H), 3.86 (s, 3H), 2.99 (s, 4H)<br>HPLC: 86%; MS: 464 (M + 1) |

Option2: Synthesis of 5-[(5-benzoylamino-phenyl)-ethyl]-1H-pyrrolo[2,3-b]pyridine-2-carboxylic acid methyl esters by Reaction of Carboxylic Acids Acid derivative was dissolved in anhydrous DMF (0.06 mol/L) with DIEA (5 eq) and HATU (2 eq). After 15 min, 5-[2-(5-amino-phenyl)-ethyl]-1H-pyrrolo[2,3-b]pyridine-2-carboxylic acid methyl ester derivatives was slowly added and mixture was stirred for 12 h at RT. DMF was evaporated and NaHCO$_{3(aq)}$ was added. Product was extracted with EtOAc, dried, filtered and evaporated to obtain a dark mixture. After purification by washing with MeOH or EtOAc or by silica column, expected product was obtained.

Table 3 shows the compound synthesized according to the synthesis Scheme 30 described above.

TABLE 3

Compounds obtained by example B with carboxylic acids

| Example No. | Used reagents | Synthesized inhibitors (mass and analytical data) |
|---|---|---|
| OR1057 | 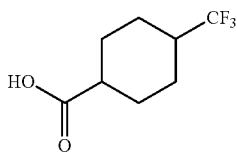 [SMILES: O=C(O)C1CCC(C(F)(F)F)CC1] | 5-(2-{2-Methyl-5-[(4-trifluoromethyl-cyclohexanecarbonyl)-amino]-phenyl}-ethyl)-1H-pyrrolo[2,3-b]pyridine-2-carboxylic acid methyl ester<br>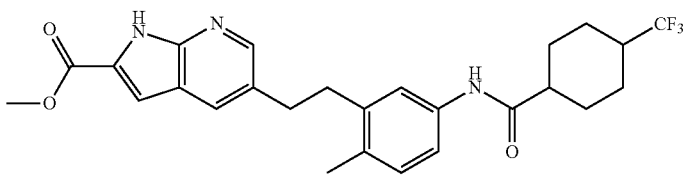 [SMILES: COC(=O)c1cc2cc(CCc3cc(NC(=O)C4CCC(C(F)(F)F)CC4)ccc3C)cnc2[nH]1]<br>Yield: 18%<br>$^1$H NMR (300 MHz, DMSO) δ 12.41 (s, 1H), 9.66 (s, 1H), 8.30 (s, 1H), 7.95 (d, J = 1.8, 1H), 7.45-7.40 (m, 1H), 7.37-7.29 (m, 1H), 7.11 (d, J = 1.8, 1H), 7.04 (d, J = 8.2, 1H), 3.87 (s, 3H), 2.97-2.77 (m, 4H), 2.64-2.56 (m, 1H), 2.37-2.24 (m, 1H), 2.19 (s, 3H), 2.01-1.85 (m, 2H), 1.83-1.38 (m, 5H), 1.36-1.19 (m, 1H)<br>HPLC: 96%; MS: 488 (M + 1) |

TABLE 3-continued

Compounds obtained by example B with carboxylic acids

| Example No. | Used reagents | Synthesized inhibitors (mass and analytical data) |
|---|---|---|
| OR0976 | 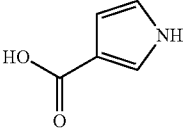 | 5-(2-{3-[(1H-Pyrrole-3-carbonyl)-amino]-phenyl}-ethyl)-1H-pyrrolo[2,3-b]pyridine-2-carboxylic acid methyl ester<br>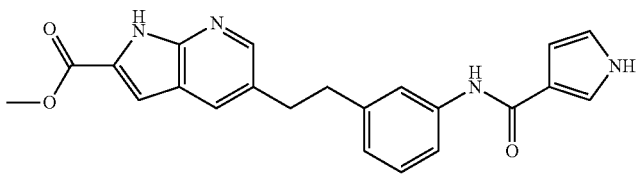 [SMILES: COC(=O)c1cc2cc(CCc3cccc(NC(=O)c4cc[nH]c4)c3)cnc2[nH]1]<br>Yield: 17%<br>$^1$H NMR (300 MHz, DMSO) δ 12.40 (s, 1H), 11.27 (s, 1H), 9.42 (s, 1H), 8.30 (s, 1H), 7.96 (s, 1H), 7.63 (s, 1H), 7.58 (d, J = 7.8, 1H), 7.52 (s, 1H), 7.19 (t, J = 7.8, 1H), 7.11 (s, 1H), 6.89 (d, J = 7.8, 1H), 6.81 (s, 1H), 6.64 (s, 1H), 3.87 (s, 3H), 3.09-2.83 (m, 4H)<br>HPLC: 98%; MS: 389 (M + 1) |
| OR0978 | 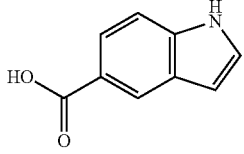 [SMILES: O=C(O)c1ccc2[nH]ccc2c1] | 5-(2-{3-[(1H-Indole-5-carbonyl)-amino]-phenyl}-ethyl)-1H-pyrrolo[2,3-b]pyridine-2-carboxylic acid methyl ester<br>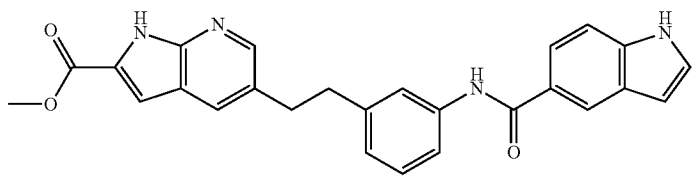 [SMILES: COC(=O)c1cc2cc(CCc3cccc(NC(=O)c4ccc5[nH]ccc5c4)c3)cnc2[nH]1]<br>Yield: 24%<br>$^1$H NMR (300 MHz, DMSO) δ 12.38 (s, 1H), 11.38 (s, 1H), 10.04 (s, 1H), 8.31 (s, 1H), 8.26 (s, 1H), 7.96 (s, 1H), 7.80-7.68 (m, 2H), 7.64 (d, J = 7.7, 1H), 7.53-7.42 (m, 2H), 7.23 (t, J = 7.7, 1H), 7.11 (s, 1H), 6.94 (d, J = 6.6, 1H), 6.58 (s, 1H), 3.86 (s, 3H), 3.09-2.85 (m, 4H)<br>HPLC: 90%; MS: 439 (M + 1) |
| OR0977 | 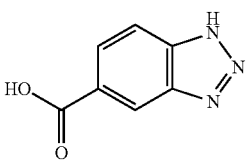 [SMILES: O=C(O)c1ccc2[nH]nnc2c1] | 5-(2-{3-[(1H-Benzotriazole-5-carbonyl)-amino]-phenyl}-ethyl)-1H-pyrrolo[2,3-b]pyridine-2-carboxylic acid methyl ester<br>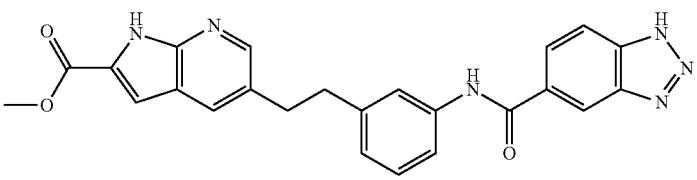 [SMILES: COC(=O)c1cc2cc(CCc3cccc(NC(=O)c4ccc5[nH]nnc5c4)c3)cnc2[nH]1]<br>Yield: 60%<br>$^1$H NMR (300 MHz, DMSO) δ 12.38 (s, 1H), 10.36 (s, 1H), 8.62 (s, 1H), 8.31 (s, 1H), 8.10-7.89 (m, 3H), 7.73 (s, 1H), 7.64 (d, J = 7.7, 1H), 7.26 (t, J = 7.7, 1H), 7.11 (s, 1H), 6.99 (d, J = 6.8, 1H), 3.86 (s, 3H), 3.11-2.87 (m, 4H)<br>HPLC >99%; MS: 441 (M + 1) |

TABLE 3-continued

Compounds obtained by example B with carboxylic acids

| Example No. | Used reagents | Synthesized inhibitors (mass and analytical data) |
|---|---|---|
| OR0981 | 5-Trifluoromethyl-pyridine-3-carboxylic acid | 5-(2-{3-[(5-Trifluoromethyl-pyridine-3-carbonyl)-amino]-phenyl}-ethyl)-1H-pyrrolo[2,3-b]pyridine-2-carboxylic acid methyl ester<br>Yield: 8%<br>$^1$H NMR (400 MHz, DMSO) δ 12.39 (s, 1H), 10.57 (s, 1H), 9.36 (d, J = 1.4, 1H), 9.18 (d, J = 1.4, 1H), 8.68 (t, J = 1.4, 1H), 8.30 (d, J = 1.8, 1H), 7.95 (d, J = 1.8, 1H), 7.66 (s, 1H), 7.61 (d, J = 7.5, 1H), 7.29 (t, J = 7.5, 1H), 7.10 (d, J = 1.8, 1H), 7.03 (d, J = 7.5, 1H), 3.86 (s, 3H), 3.06-2.91 (m, 4H).<br>HPLC: 99%; MS: 469 (M + 1) |
| OR1008 | 5-Trifluoromethyl-pyridine-3-carboxylic acid | 5-(2-{2-Chloro-5-[(5-trifluoromethyl-pyridine-3-carbonyl)-amino]-phenyl}-ethyl)-1H-pyrrolo[2,3-b]pyridine-2-carboxylic acid methyl ester<br>Yield: 7%<br>$^1$H NMR (300 MHz, DMSO) δ 12.43 (s, 1H), 10.70 (s, 1H), 9.40 (s, 1H), 9.23 (s, 1H), 8.71 (s, 1H), 8.36 (s, 1H), 8.00 (d, J = 1.2, 1H), 7.82 (d, J = 2.5, 1H), 7.74 (dd, J = 2.5, 8.7, 1H), 7.49 (d, J = 8.7, 1H), 7.16 (s, 1H), 3.91 (s, 3H), 3.07 (bs, 4H)<br>HPLC: 97%; MS: 503 (M + 1) |
| OR0834 | 4-(4-methyl-piperazin-1-ylmethyl)-benzoic acid | 5-(2-{2-Methyl-5-[4-(4-methyl-piperazin-1-ylmethyl)-benzoylamino]-phenyl}-ethyl)-1H-pyrrolo[2,3-b]pyridine-2-carboxylic acid methyl ester<br>Yield: 42%<br>$^1$H NMR (300 MHz, DMSO) δ 12.41 (s, 1H), 10.08 (s, 1H), 8.32 (s, 1H), 7.97 (s, 1H), 7.90 (d, J = 7.8, 2H), 7.64 (s, 1H), 7.53 (d, J = 8.4, 1H), 7.43 (d, J = 7.8, 2H), 7.20-7.02 (m, 2H), 3.87 (s, 3H), 3.52 (s, 2H), 3.04-2.80 (m, 4H), 2.36 (bs, 8H), 2.22 (s, 3H), 2.15 (s, 3H)<br>HPLC: >99%; MS: 526 (M + 1) |

TABLE 3-continued

Compounds obtained by example B with carboxylic acids

| Example No. | Used reagents | Synthesized inhibitors (mass and analytical data) |
|---|---|---|
| OR0921 | 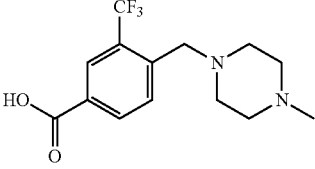 | 5-(2-{3-[4-(4-Methyl-piperazin-1-ylmethyl)-3-trifluoromethyl-benzoylamino]-phenyl}-ethyl)-1H-pyrrolo[2,3-b]pyridine-2-carboxylic acid methyl ester<br>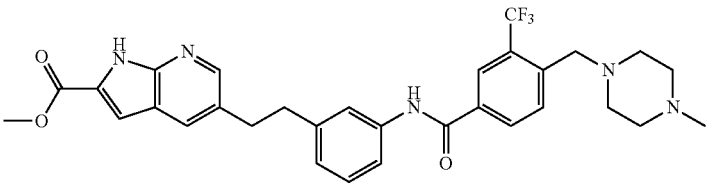<br>Yield: 19%<br>$^1$H NMR (300 MHz, DMSO) δ 12.35 (s, 1H), 10.38 (s, 1H), 8.29 (d, J = 1.7, 1H), 8.29 (s, 1H), 8.22 (d, J = 8.4, 1H), 7.94 (d, J = 1.7, 1H), 7.92 (d, J = 8.4, 1H), 7.66 (s, 1H), 7.61 (d, J = 7.7, 1H), 7.26 (t, J = 7.7, 1H), 7.10 (s, 1H), 7.00 (d, J = 7.7, 1H), 3.86 (s, 3H), 3.68 (s, 2H), 3.08-2.86 (m, 4H), 2.42 (bs, 4H), 2.34 (bs, 4H), 2.16 (s, 3H)<br>HPLC: 97%; MS: 580 (M + 1) |
| OR0748 | 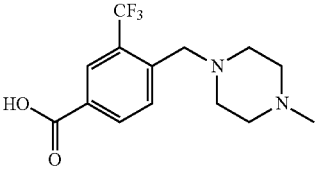 | 5-(2-{2-Methyl-5-[4-(4-methyl-piperazin-1-ylmethyl)-3-trifluoromethyl-benzoylamino]-phenyl}-ethyl)-1H-pyrrolo[2,3-b]pyridine-2-carboxylic acid methyl ester<br>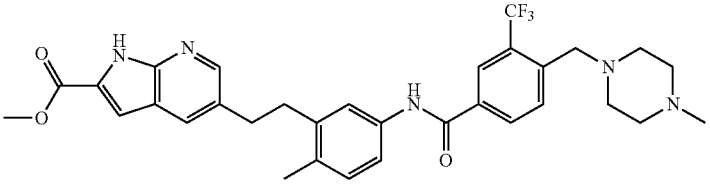<br>Yield: 24%<br>$^1$H NMR (300 MHz, DMSO) δ 12.42 (s, 1H), 10.35 (s, 1H), 8.38-8.19 (m, 3H), 7.98 (s, 1H), 7.92 (d, J = 7.9, 1H), 7.62 (s, 1H), 7.56 (d, J = 7.9, 1H), 7.18-7.10 (m, 2H), 3.88 (s, 3H), 3.73 (s, 2H), 3.01-2.87 (m, 6H), 2.81-2.60 (m, 6H), 2.41 (s, 3H), 2.25 (s, 3H)<br>HPLC: 98%: MS: 594 (M + 1) |
| OR1006 | 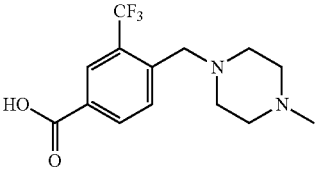 | 5-(2-{2-Chloro-5-[4-(4-methyl-piperazin-1-ylmethyl)-3-trifluoromethyl-benzoylamino]-phenyl}ethyl)-1H-pyrrolo[2,3-b]pyridine-2-carboxylic acid methyl ester<br>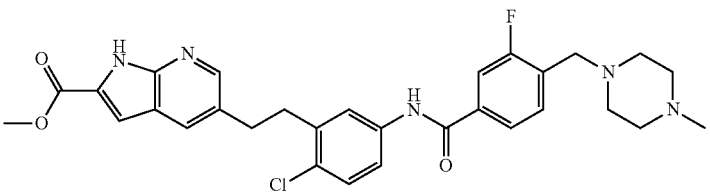<br>Yield: 11%<br>$^1$H NMR (300 MHz, DMSO) 12.40 (s, 1H), 10.49 (s, 1H), 8.31 (d, J = 2.0, 1H), 8.23 (s, 1H), 8.19 (d, J = 8.1, 1H), 7.96 (d, J = 2.0, 1H), 7.92 (d, J = 8.1, 1H), 7.78 (d, J = 2.5, 1H), 7.69 (dd, J = 2.5, 8.7, 1H), 7.42 (d, J = 8.7, 1H), 7.12 (d, J = 2.0, 1H), 3.87 (s, 3H), 3.68 (s, 2H), 3.01 (s, 4H), 2.42 (sb, 4H), 2.36 (sb, 4H), 2.17 (s, 3H)<br>HPLC: 98%; MS: 614 (M + 1) |

TABLE 3-continued

Compounds obtained by example B with carboxylic acids

| Example No. | Used reagents | Synthesized inhibitors (mass and analytical data) |
|---|---|---|
| OR0920 | 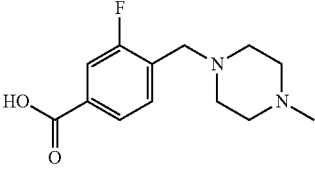 | 5-(2-{5-[3-Fluoro-4-(4-methyl-piperazin-1-ylmethyl)-benzoylamino]-2-methyl-phenyl}-ethyl)-1H-pyrrolo[2,3-b]pyridine-2-carboxylic acid methyl ester<br>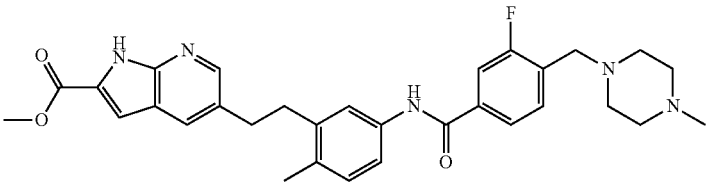<br>Yield: 18%<br>$^1$H NMR (300 MHz, DMSO) δ 12.44 (s, 1H), 10.18 (s, 1H), 8.36 (s, 1H), 8.01 (s, 1H), 7.86-7.73 (m, 2H), 7.66 (s, 1H), 7.63-7.51 (m, 2H), 7.15 (bs, 2H), 3.91 (s, 3H), 3.61 (s, 2H), 3.02-2.88 (m, 4H), 2.41 (bs, 4H), 2.33 (bs, 4H), 2.26 (s, 3H), 2.20 (s, 3H)<br>HPLC: >99%; MS: 544 (M + 1) |
| OR0922 | 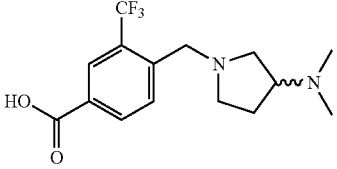 | 5-(2-{5-[4-(3-Dimethylamino-pyrrolidin-1-ylmethyl)-3-trifluoromethyl-benzoylamino]-phenyl}-ethyl)-1H-pyrrolo[2,3-b]pyridine-2-carboxylic acid methyl ester<br>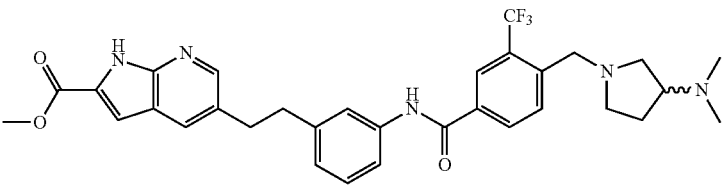<br>Yield: 19%<br>$^1$H NMR (300 MHz, DMSO) δ 12.32 (s, 1H), 10.39 (s, 1H), 8.30 (d, J = 2.0, 1H), 8.24 (s, 1H), 8.22 (d, J = 8.1, 1H), 7.94 (d, J = 2.0, 1H), 7.89 (d, J = 7.9, 1H), 7.66 (s, 1H), 7.61 (d, J = 8.1, 1H), 7.26 (t, J = 7.9, 1H), 7.10 (s, 1H), 6.99 (d, J = 7.9, 1H), 3.86 (s, 3H), 3.82 (d, J = 14.7, 1H), 3.74 (d, J = 14.7, 1H), 3.05-2.87 (m, 4H), 2.82-2.57 (m, 4H), 2.43-2.31 (m, 1H), 2.09 (s, 6H), 1.94-1.78 (s, 1H), 1.74-1.54 (s, 1H)<br>HPLC: 99%; MS: 594 (M + 1) |
| OR0775 | 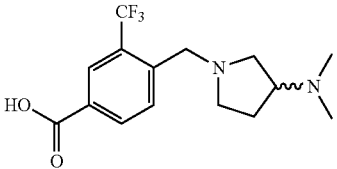 | 5-(2-{5-[4-(3-Dimethylamino-pyrrolidin-1-ylmethyl)-3-trifluoromethyl-benzoylamino]-2-methyl-phenyl}-ethyl)-1H-pyrrolo[2,3-b]pyridine-2-carboxylic acid methyl ester<br>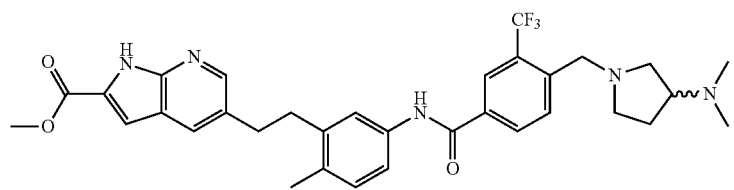<br>Yield: 68%<br>$^1$H NMR (300 MHz, DMSO) δ 12.40 (s, 1H), 10.32 (s, 1H), 8.32 (s, 1H), 8.25-8.18 (m, 2H), 7.97 (s, 1H), 7.89 (d, J = 8.0, 1H), 7.61 (s, 1H), 7.55 (d, J = 8.0, 1H), 7.17-7.08 (m, 2H), 3.87 (s, 3H), 3.86-3.69 (m, 2H), 3.00-2.85 (m, 4H), 2.81-2.52 (m, 4H), 2.43-2.33 (m, 1H), 2.23 (s, 3H), 2.09 (s, 6H), 1.96-1.80 (m, 1H), 1.77-1.57 (m, 1H)<br>HPLC: 94%; MS: 608 (M + 1) |

TABLE 3-continued

Compounds obtained by example B with carboxylic acids

| Example No. | Used reagents | Synthesized inhibitors (mass and analytical data) |
|---|---|---|
| OR1007 | 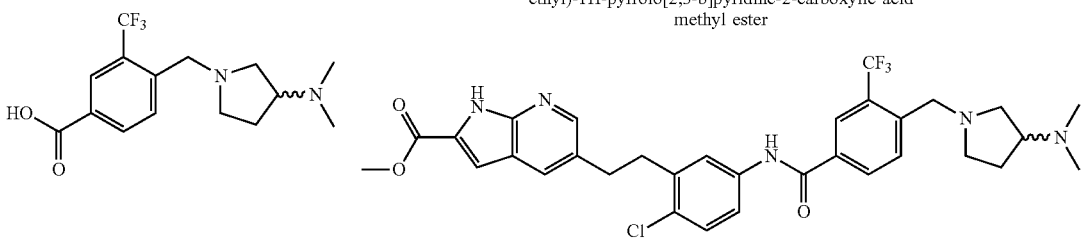 | 5-(2-{2-Chloro-5-[4-(3-dimethylamino-pyrrolidin-1-ylmethyl)-3-trifluoromethyl-benzoylamino]-phenyl}-ethyl)-1H-pyrrolo[2,3-b]pyridine-2-carboxylic acid methyl ester<br><br>Yield: 6%<br>$^1$H NMR (300 MHz, DMSO) δ 12.37 (s, 1H), 10.47 (s, 1H), 8.31 (d, J = 2.0, 1H), 8.22 (s, 1H), 8.20 (d, J = 7.9, 1H), 7.95 (d, J = 2.0, 1H), 7.90 (d, J = 7.9, 1H), 7.78 (d, J = 2.5, 1H), 7.69 (dd, J = 2.5, 8.7, 1H), 7.42 (d, J = 8.7, 1H), 7.11 (s, 1H), 3.87 (s, 3H), 3.83 (d, J = 15.2, 1H), 3.75 (d, J = 15.2, 1H), 3.01 (bs, 4H), 2.82-2.52 (m, 4H), 2.43-2.34 (m 1H), 2.09 (s, 6H), 1.96-1.81 (m, 1H), 1.72-1.57 (m, 1H)<br>HPLC: 94%; MS: 628 (M + 1) |
| OR1044 | 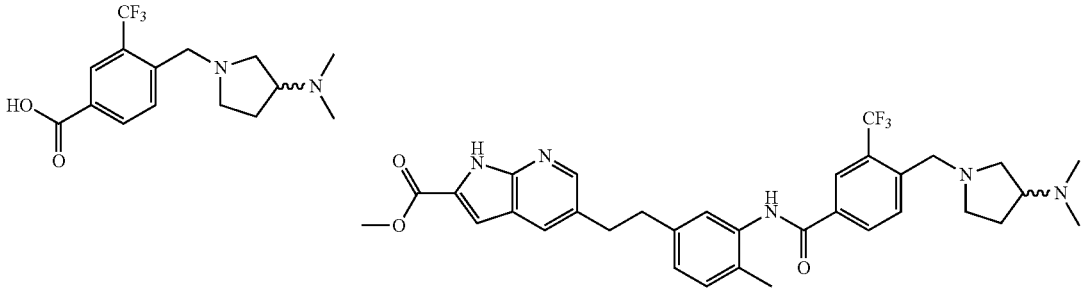 | 5-(2-{5-[4-(3-Dimethylamino-pyrrolidin-1-ylmethyl)-3-trifluoromethyl-benzoylamino]-4-methyl-phenyl}-ethyl)-1H-pyrrolo[2,3-b]pyridine-2-carboxylic acid methyl ester<br><br>Yield: 7%<br>$^1$H NMR (300 MHz, DMSO) δ 12.38 (s, 1H), 10.10 (s, 1H), 8.30 (d, J = 2.0, 1H), 8.28-8.21 (m, 2H), 7.95 (d, J = 2.0, 1H), 7.90 (d, J = 8.0, 1H), 7.23 (s, 1H), 7.17 (d, J = 7.8, 1H), 7.10 (s, 1H), 7.05 (d, J = 7.8, 1H), 3.86 (s, 3H), 3.83 (d, J = 15.0, 1H), 3.75 (d, J = 15.0, 1H), 3.01-2.89 (m, 4H), 2.79-2.54 (m, 4H), 2.42-2.34 (m, 1H), 2.18 (s, 3H), 2.09 (s, 6H), 1.96-1.82 (m, 1H), 1.71-1.58 (m, 1H)<br>HPLC: 92%; MS: 608 (M + 1) |

TABLE 3-continued

Compounds obtained by example B with carboxylic acids

| Example No. | Used reagents | Synthesized inhibitors (mass and analytical data) |
|---|---|---|
| OR1068 | (structure: 3-(4-methyl-1H-imidazol-1-yl)-5-(trifluoromethyl)benzoic acid) | 5-(2-{4-Methyl-3-[3-(4-methyl-imidazol-1-yl)-5-trifluoromethyl-benzoylamino]-phenyl}-ethyl)-1H-pyrrolo[2,3-b]pyridine-2-carboxylic acid methyl ester<br><br>(product structure)<br><br>Yield: 10%<br>$^1$H NMR (400 MHz, DMSO) 12.25 (s, 1H), 10.26 (s, 1H), 8.50 (s, 1H), 8.43 (s, 1H), 8.32 (s, 1H), 8.28 (s, 1H), 8.21 (s, 1H), 7.97 (s, 1H), 7.74 (s, 1H), 7.29 (s, 1H), 7.22 (d, J = 7.8, 1H), 7.15-7.06 (m, 2H), 3.89 (s, 3H), 3.07-2.90 (m, 4H), 2.23 (s, 3H), 2.22 (s, 3H)<br>HPLC: 96%; MS: 562 (M + 1) |

Example C

Synthesis of 5-(-2-{5-benzoylamino-2-methyl-phenyl}-vinyl)-1H-pyrrolo[2,3-b]pyridine-2-carboxylic acid methyl esters Scheme 31 - General synthesis scheme of example C

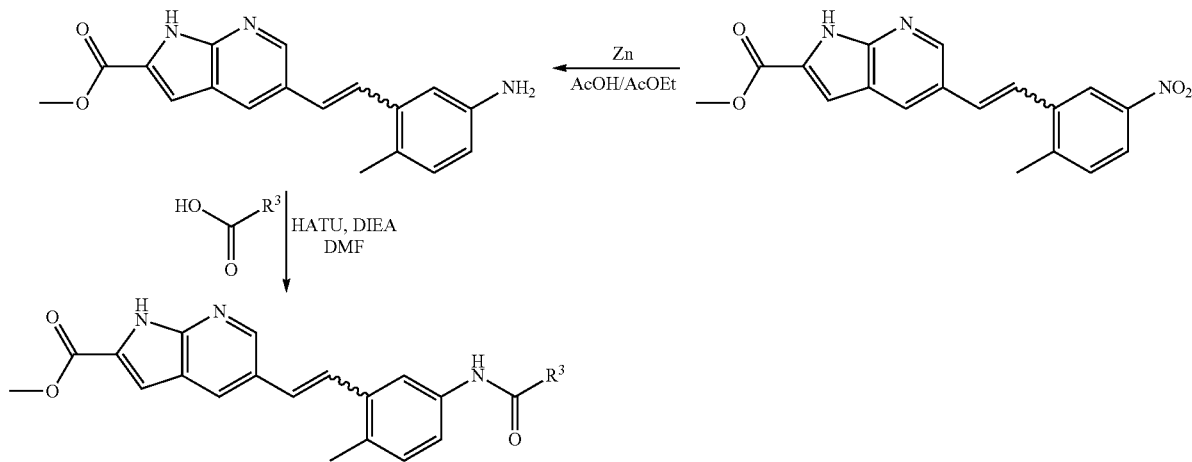

Step 1: Protocol for the Preparation of 5-[2-(5-amino-2-methyl-phenyl)-vinyl]-1H-pyrrolo[2,3-b]pyridine-2-carboxylic acid methyl ester 5-[-2-(2-Methyl-5-nitro-phenyl)-vinyl]-1H-pyrrolo[2,3-b]pyridine-2-carboxylic acid methyl ester (283 mg) was dissolved in a AcOH/AcOEt mixture (1/2) and zinc powder (15 eq) was added. The mixture was exposed to ultrasound at RT for 30 minutes. The crude mixture was filtered on celite and washed with AcOEt. The filtrate was concentrated and purified on reverse phase column chromatography to give a yellow oil which precipitate as a white solid (144 mg) when triturated in a NaHCO$_3$ solution.

Yield=56%. ESI-MS: m/z 308 ([M+H]$^+$). HPLC purity: 88%.

Step 2: General Protocol for the Preparation of 5-[2-(5-benzoylamino-2-methyl-phenyl)-vinyl]-1H-pyrrolo[2,3-b]pyridine-2-carboxylic acid methyl esters Acid derivative was dissolved in anhydrous DMF (0.06 mol/L) with DIEA (5 eq) and HATU (2 eq). After 15 min, 5-[2-(5-amino-2-methyl-phenyl)-vinyl]-1H-pyrrolo[2,3-b]pyridine-2-carboxylic acid methyl ester was slowly added and mixture was stirred for 12 h at RT. DMF was evaporated and NaHCO$_{3(aq)}$ was added. Product was extracted with EtOAc, dried, filtered and evaporated to obtain a dark mixture. After purification by washing with MeOH or EtOAc or by silica column, expected product was obtained.

Table 4 shows the compounds synthesized according to the synthesis Scheme 31 described

TABLE 4

Compounds obtained by example C

| Example No. | Used reagents | Synthesized inhibitors (mass and analytical data) |
|---|---|---|
| OR0776 | 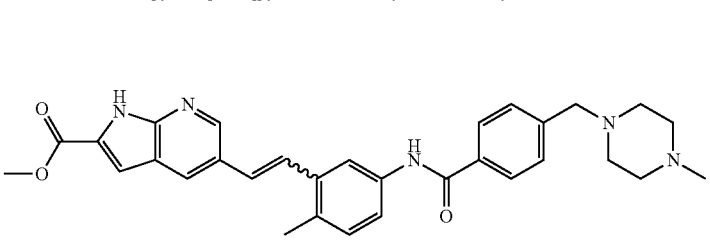 | 5-(-2-{2-Methyl-5-[4-(4-methyl-piperazin-1-ylmethyl)-benzoylamino]-phenyl}-vinyl)-1H-pyrrolo[2,3-b]pyridine-2-carboxylic acid methyl ester<br><br>Yield: 46% (ee Z/E = 25/75)<br>$^1$H NMR (300 MHz, DMSO) δ 12.59 (s, 0.25H), 12.48 (s, 0.75H), 10.17 (s, 0.25H), 10.04 (s, 0.75H), 8.70 (s, 0.25H), 8.42 (s, 0.25H), 8.15 (s, 0.75H), 8.09 (s, 0.25H), 7.94 (d, J = 7.8, 0.5H), 7.85 (s, 0.75H), 7.80 (d, J = 8.2, 1.5H), 7.69 (d, J = 8.3, 0.75H), 7.61 (d, J = 7.7, 0.25H), 7.55 (s, 0.75H), 7.50-7.42 (m, 0.5H), 7.37 (d, J = 8.1, 1.5H), 7.28-7.10 (m, 1.75H), 7.05 (s, 0.75H), 6.79 (d, J = 12.4, 0.75H), 6.72 (d, J = 12.3, 0.75H), 3.89 (s, 0.75H), 3.84 (s, 2.25H), 3.54 (s, 0.5H), 3.49 (s, 1.5H), 2.41 (s, 0.75H), 2.35 (s, 8H), 2.18 (s, 2.25H), 2.15 (s, 0.75H), 2.13 (s, 2.25H)<br>HPLC: 96%; MS: 524 (M + 1) |
| OR0777 | 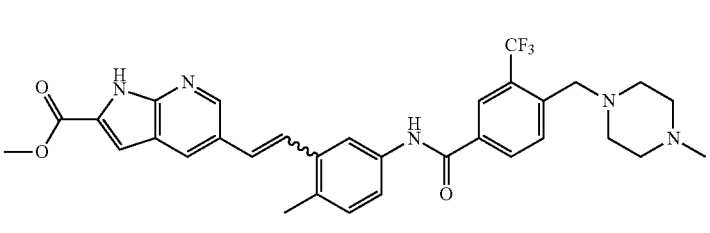 | 5-(-2-{2-Methyl-5-[4-(4-methyl-piperazin-1-ylmethyl)-3-trifluoromethyl-benzoylamino]-phenyl}-vinyl)-1H-pyrrolo[2,3-b]pyridine-2-carboxylic acid methyl ester<br><br>Yield: 5% (ee Z/E = 40/60)<br>$^1$H NMR (300 MHz, DMSO) δ 12.60 (s, 0.4H), 12.48 (s, 0.6H), 10.42 (s, 0.4H), 10.27 (s, 0.6H), 8.72 (s, 0.4H), 8.43 (s, 0.4H), 8.29 (s, 0.4H), 8.26 (d, J = 8.4, 0.4H), 8.18-8.02 (m, 2.2H), 7.93 (d, J = 8.4, 0.4H), 7.90-7.83 (m, 1.2H), 7.69 (d, J = 8.1, 0.6H), 7.61 (d, J = 8.4, 0.4H), 7.56-7.46 (m, 1H), 7.30-7.10 (m, 1.8H), 7.05 (s, 0.6H), 6.80 (d, J = 12.3, 0.6H), 6.72 (d, J = 12.3, 0.6H), 3.89 (s, 1.2H), 3.84 (s, 1.8H), 3.69 (s, 0.8H), 3.64 (s, 1.2H), 2.42 (s, 1.8H), 2.40-2.25 (m, 8H), 2.19 (s, 1.8H), 2.18 (s, 1.2H), 2.16 (s, 1.2H)<br>HPLC: 99%; MS: 592 (M + 1) |

77 78

TABLE 4-continued

Compounds obtained by example C

| Example No. | Used reagents | Synthesized inhibitors (mass and analytical data) |
|---|---|---|
| OR0778 | 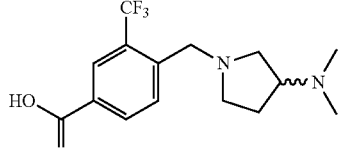 | 5-(2-{5-[4-(3-Dimethylamino-pyrrolidin-1-ylmethyl)-3-trifluoromethyl-benzoylamino]-2-methyl-phenyl}-vinyl)-1H-pyrrolo[2,3-b]pyridine-2-carboxylic acid methyl ester 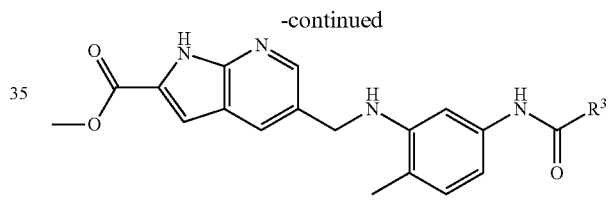 Yield: 9% (ee Z/E = 25/75) $^1$H NMR (300 MHz, DMSO) δ 12.59 (s, 0.25H), 12.48 (s, 0.75H), 10.42 (s, 0.25H), 10.27 (s, 0.75H), 8.72 (s, 0.25H), 8.43 (s, 0.25H), 8.31-8.22 (m, 0.5H), 8.17-8.03 (m, 2.5H), 7.91 (d, J = 8.1, 0.25H), 7.88-7.79 (m, 1.5H), 7.69 (d, J = 8.3, 0.75H), 7.61 (d, J = 8.1, 0.25H), 7.56-7.48 (m, 1H), 7.29-7.11 (m, 1.5H), 7.05 (s, 0.75H), 6.80 (d, J = 12.3, 0.75H), 6.73 (d, J = 12.3, 0.75H), 3.89 (s, 0.75H), 3.84 (s, 2.25H), 3.79 (d, J = 15.4, 1H), 3.71 (d, J = 15.4, 1H), 2.82-2.53 (m, 3H), 2.44-2.30 (m, 2H), 2.19 (s, 2.25H), 2.09 (s, 1.5H), 2.07 (s, 4.5H), 1.99 (s, 0.75H), 1.92-1.77 (m, 1H), 1.70-1.55 (m, 1H) HPLC: 99%; MS: 606 (M + 1) |

Example D

Synthesis of 5-{[2-methyl-5-benzoylamino-phenylamino]-methyl}-1H-pyrrolo[2,3-b]pyridine-2-carboxylic acid methyl esters Scheme 32 - General synthesis scheme of example D

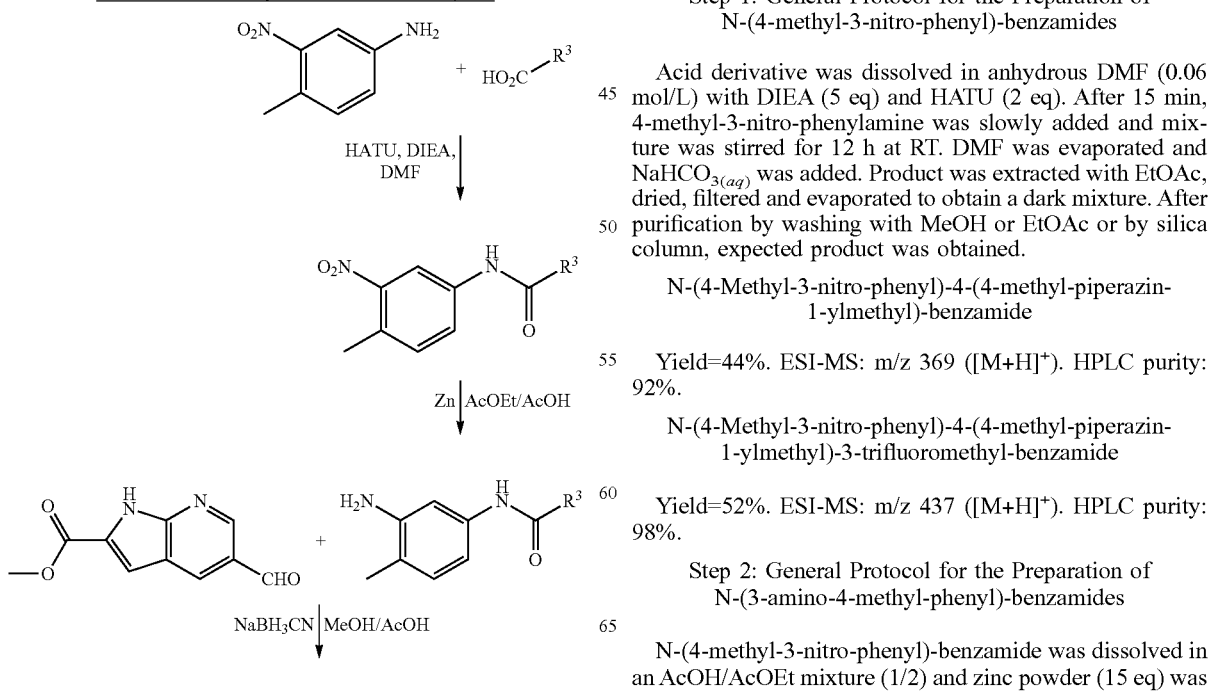

Step 1: General Protocol for the Preparation of N-(4-methyl-3-nitro-phenyl)-benzamides Acid derivative was dissolved in anhydrous DMF (0.06 mol/L) with DIEA (5 eq) and HATU (2 eq). After 15 min, 4-methyl-3-nitro-phenylamine was slowly added and mixture was stirred for 12 h at RT. DMF was evaporated and NaHCO$_{3(aq)}$ was added. Product was extracted with EtOAc, dried, filtered and evaporated to obtain a dark mixture. After purification by washing with MeOH or EtOAc or by silica column, expected product was obtained.

N-(4-Methyl-3-nitro-phenyl)-4-(4-methyl-piperazin-1-ylmethyl)-benzamide

Yield=44%. ESI-MS: m/z 369 ([M+H]$^+$). HPLC purity: 92%.

N-(4-Methyl-3-nitro-phenyl)-4-(4-methyl-piperazin-1-ylmethyl)-3-trifluoromethyl-benzamide Yield=52%. ESI-MS: m/z 437 ([M+H]$^+$). HPLC purity: 98%.

Step 2: General Protocol for the Preparation of N-(3-amino-4-methyl-phenyl)-benzamides N-(4-methyl-3-nitro-phenyl)-benzamide was dissolved in an AcOH/AcOEt mixture (1/2) and zinc powder (15 eq) was added. The mixture was stirred at RT for 1.5 hours. The crude mixture was filtered on celite and concentrated. The residue was dissolved in water, basified to pH 7-8 by NaHCO$_3$, extracted by AcOEt, dried and concentrated to give an orange solid.

N-(3-Amino-4-methyl-phenyl)-4-(4-methyl-piperazin-1-ylmethyl)-benzamide

Yield=95%. ESI-MS: m/z 339 ([M+H]$^+$). HPLC purity: 97%.

N-(3-Amino-4-methyl-phenyl)-4-(4-methyl-piperazin-1-ylmethyl)-3-trifluoromethyl-benzamide Yield=94%. ESI-MS: m/z 407 ([M+H]$^+$). HPLC purity: 98%.

N-(3-Amino-4-methyl-phenyl)-4-methyl-benzamide

One reduction was left overnight, and this unexpected compound.

Yield=42%. ESI-MS: m/z 341 ([M+H]$^+$). HPLC purity: 98%.

Step 3: General Protocol for the Preparation of 5-{[2-methyl-5-benzoylamino-phenylamino]-methyl}-1H-pyrrolo[2,3-b]pyridine-2-carboxylic acid methyl esters Under argon, 5-formyl-1H-pyrrolo[2,3-b]pyridine-2-carboxylic acid methyl ester (1 eq) and N-(3-amino-4-methyl-phenyl)-benzamide (1 eq) were dissolved in MeOH (2 ml) with AcOH (200 µl) and allowed to stir at RT for 2 hours. NaBH$_3$CN (2 eq) was then added and the mixture was stirred overnight at RT. The precipitate was filtered and rinsed with MeOH and Et$_2$O.

Table 5 shows the compounds synthesized according to the synthesis Scheme 32 described above.

TABLE 5

Compounds obtained by example D

| Example No. | Used reagents | Synthesized inhibitors (mass and analytical data) |
|---|---|---|
| OR0738 | 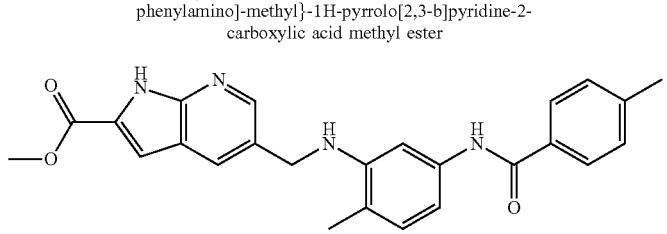 | 5-{[2-Methyl-5-(4-methyl-benzoylamino)-phenylamino]-methyl}-1H-pyrrolo[2,3-b]pyridine-2-carboxylic acid methyl ester<br>Yield: 23%<br>$^1$H NMR (300 MHz, DMSO) δ 12.44 (s, 1H), 9.79 (s, 1H), 8.48 (s, 1H), 8.06 (s, 1H), 7.78 (d, J = 7.9, 2H), 7.28 (d, J = 7.8, 2H), 7.14 (s, 1H), 7.00 (d, J = 9.1, 1H), 6.92 (d, J = 9.1, 1H), 5.64 (s, 1H), 4.44 (s, 1H), 3.85 (s, 3H), 2.35 (s, 3H), 2.13 (s, 3H)<br>HPLC: 89%; MS: 429 (M + 1) |
| OR0746 | 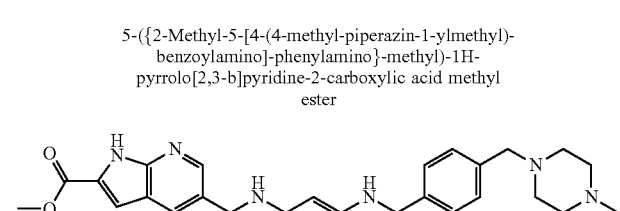 | 5-({2-Methyl-5-[4-(4-methyl-piperazin-1-ylmethyl)-benzoylamino]-phenylamino}-methyl)-1H-pyrrolo[2,3-b]pyridine-2-carboxylic acid methyl ester<br>Yield: 17%<br>$^1$H NMR (400 MHz, DMSO) δ 12.44 (s, 1H), 9.85 (s, 1H), 8.48 (d, J = 2.0, 1H), 8.05 (s, 1H), 7.83 (d, J = 8.2, 2H), 7.40 (d, J = 2.0, 2H), 7.14 (d, J = 2.0, 1H), 7.02-6.96 (m, 2H), 6.91 (d, J = 7.8, 1H), 5.67 (t, J = 5.9, 1H), 4.44 (d, J = 5.9, 2H), 3.85 (s, 3H), 3.57 (s, 2H), 3.25-2.55 (m, 8H), 2.13 (s, 3H), 2.08 (s, 2H)<br>HPLC: 96%; MS: 527 (M + 1) |

TABLE 5-continued

Compounds obtained by example D

| Example No. | Used reagents | Synthesized inhibitors (mass and analytical data) |
|---|---|---|
| OR0747 | | 5-({2-Methyl-5-[4-(4-methyl-piperazin-1-ylmethyl)-3-trifluoromethyl-benzoylamino]-phenylamino}-methyl)-1H-pyrrolo[2,3-b]pyridine-2-carboxylic acid methyl ester<br><br>Yield: 3.5%<br>$^1$H NMR (400 MHz, DMSO) δ 12.41 (s, 1H), 10.07 (s, 1H), 8.48 (d, J = 2.0, 1H), 8.15-8.09 (m, 2H), 8.05 (s, 1H), 7.86 (d,J = 8.6, 1H), 7.14 (d, 1H), 7.04-6.89 (m, 3H), 5.66 (t, J = 5.8, 1H), 4.44 (d, J = 5.8, 2H), 3.85 (s, 3H), 3.65 (s, 2H), 2.46-2.26 (m, 8H), 2.16 (s, 3H), 2.14 (s, 3H)<br>HPLC: 95%; MS: 594 (M + 1) |

Example D'

Synthesis of 5-{[5-Benzamido-2-methyl-phenylimino]-methyl}-1H-pyrrolo[2,3-b]pyridine-2-carboxylic acid methyl ester Scheme 33 - General synthesis scheme of example D'

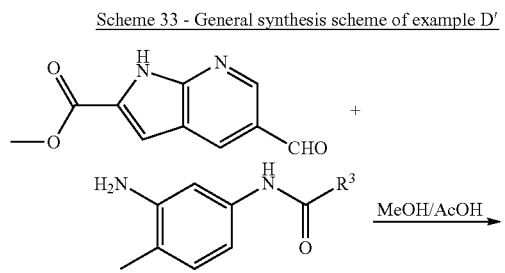

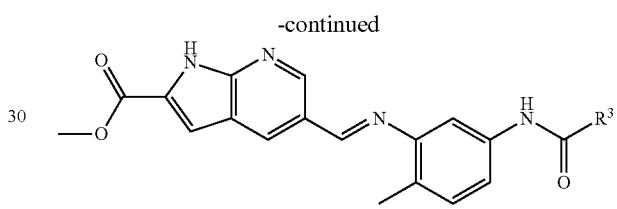

Under argon, 5-formyl-1H-pyrrolo[2,3-b]pyridine-2-carboxylic acid methyl ester (1 eq) and N-(3-amino-4-methylphenyl)-benzamide intermediate (1.5 eq) were dissolved in MeOH (2 ml) with AcOH (200 µl) and a spoon of MgSO$_4$. The mixture was stirred at room temperature for 3 h. MgSO$_4$ was filtered, the crude was concentrated then purified on silicagel chromatography to give the final compound.3

Table 6 shows the compounds synthesized according to the synthesis Scheme 33 described above.

TABLE 6

Compound obtained by example D'

| Example No. | Used reagents | Synthesized inhibitors (mass and analytical data) |
|---|---|---|
| OR1070 | | 5-({2-Methyl-5-[4-(4-methyl-piperazin-1-ylmethyl)-3-trifluoromethyl-benzoylamino]-phenylimino}-methyl)-1H-pyrrolo[2,3-b]pyridine-2-carboxylic acid methyl ester<br><br>Yield: 5%<br>$^1$H NMR (400 MHz, DMSO) δ 12.86 (s, 1H), 10.43 (s, 1H), 9.02 (d, J = 1.9, 1H), 8.70 (d, J = 1.9, 1H), 8.65 (s, 1H), 8.26 (s, 1H), 8.24 (d, J = 8.1, 1H), 7.93 (d, J = 8.1, 1H), 7.57-7.51 (m, |

TABLE 6-continued

Compound obtained by example D'

| Example No. | Used reagents | Synthesized inhibitors (mass and analytical data) |
|---|---|---|
| | | 2H), 7.34 (d, J = 1.7, 1H), 7.25 (d, J = 8.8, 1H), 3.91 (s, 3H), 3.68 (s, 2H), 2.48-2.31 (m, 8H), 2.30 (s, 3H), 2.17 (s, 3H) HPLC; MS: Unstable in LCMS |

Example E

Synthesis of 5-{5-benzoylamino-2-methyl-phenoxymethyl}-1H-pyrrolo[2,3-b]pyridine-2-carboxylic acid methyl esters

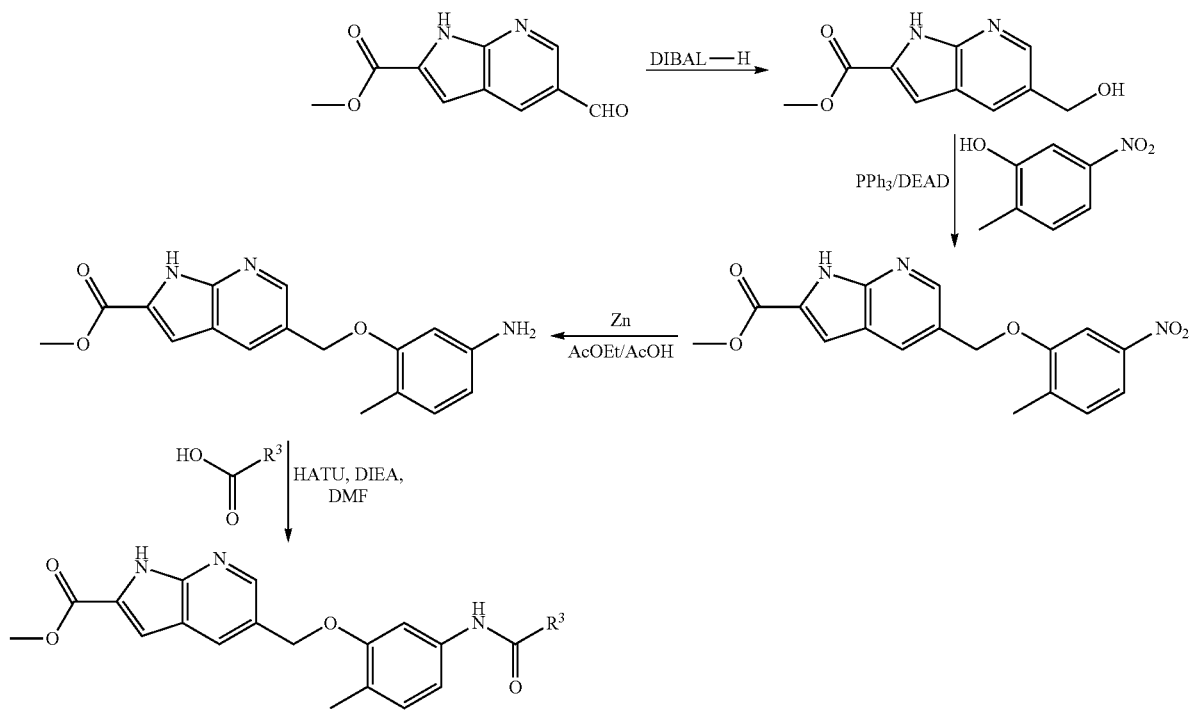

Scheme 34 - General synthesis scheme of example E

Step 1: Protocol for the Preparation of 5-hydroxymethyl-1H-pyrrolo[2,3-b]pyridine-2-carboxylic acid methyl ester A solution of 5-formyl-1H-pyrrolo[2,3-b]pyridine-2-carboxylic acid methyl ester (667 mg, 3.27 mmol) in dry THF (35 mL) under argon was cooled at 0° C. and a solution of DIBAL-H in cyclohexane 1M (9.8 mL, 3 eq) in dry THF (17 mL) was added slowly. The mixture was stirred at 0° C. for 3 h then quenched by H$_2$O. The mixture was concentrated and the crude was washed by NaHCO$_3$ and extracted by AcOEt. Organic layer was dried with Na$_2$SO$_4$ and AcOEt was evaporated under reduce pressure. The crude was purified on a normal phase column chromatography.

Yield=45%. $^1$H NMR (300 MHz, DMSO) δ 12.45 (s, 1H), 8.38 (d, J=1.9, 1H), 8.02 (d, J=1.9, 1H), 7.16 (d, J=1.6, 1H), 5.25 (t, J=5.6, 1H), 4.59 (d, J=5.6, 2H), 3.87 (s, 3H). ESI-MS: m/z 207 ([M+H]$^+$). HPLC purity: 80%.

Step 2: Protocol for the Preparation of 5-(2-methyl-5-nitro-phenoxymethyl)-1H-pyrrolo[2,3-b]pyridine-2-carboxylic acid methyl ester To a solution of 2-methyl-5-nitrophenol (1 eq) in dry CH$_2$Cl$_2$ (4 mL) under Argon, was added PPh$_3$ (1 eq) followed by 5-hydroxymethyl-1H-pyrrolo[2,3-b]pyridine-2-carboxylic acid methyl ester (180 mg, 1 eq). A solution of DEAD (151 µl, 0.96 mmol) in CH$_2$Cl$_2$ (2 mL) was added slowly and the mixture was stirred at room temperature overnight. The crude was filtered and the precipitate was washed with CH$_2$Cl$_2$.

Yield=40%. $^1$H NMR (300 MHz, DMSO) δ 12.59 (s, 1H), 8.57 (d, J=1.6, 1H), 8.25 (s, 1H), 7.90 (s, 1H), 7.80 (d, J=8.2, 1H), 7.47 (d, J=8.2, 1H), 7.22 (s, 1H), 5.39 (s, 2H), 3.89 (s, 3H), 2.28 (s, 3H). ESI-MS: m/z 342 ([M+H]⁺). HPLC purity: 51%.

Step 3: Protocol for the Preparation of 5-(5-amino-2-methyl-phenoxymethyl)-1H-pyrrolo[2,3-b]pyridine-2-carboxylic acid methyl ester 5-(2-methyl-5-nitro-phenoxymethyl)-1H-pyrrolo[2,3-b]pyridine-2-carboxylic acid methyl ester (100 mg) was dissolved in a AcOH/AcOEt mixture (1/2) and zinc powder (15 eq) was added. The mixture was exposed to ultrasound at RT for 30 minutes. The crude mixture was filtered on celite and washed with AcOEt. The filtrate was concentrated to afford a yellowish precipitate which gave a white solid when triturated in a NaHCO₃ solution.

Quantitative yield. ESI-MS: m/z 312 ([M+H]⁺). HPLC purity: 80%.

Step 4: General Protocol for the Preparation of 5-{5-benzoylamino-2-methyl-phenoxymethyl}-1H-pyrrolo[2,3-b]pyridine-2-carboxylic acid methyl esters Acid derivative was dissolved in anhydrous DMF (0.06 mol/L) with DIEA (5 eq) and HATU (2 eq). After 15 min, 5-(5-amino-2-methyl-phenoxymethyl)-1H-pyrrolo[2,3-b]pyridine-2-carboxylic acid methyl ester was slowly added and mixture was stirred for 12 h at RT. DMF was evaporated and NaHCO₃₍aq₎ was added. Product was extracted with EtOAc, dried, filtered and evaporated to obtain a dark mixture. After purification by washing with MeOH or EtOAc or by silica column, expected product was obtained.

Table 7 shows the compounds synthesized according to the synthesis Scheme 34 described above.

TABLE 7

Compounds obtained by example E

| Example No. | Used reagents | Synthesized inhibitors (mass and analytical data) |
|---|---|---|
| OR0779 | 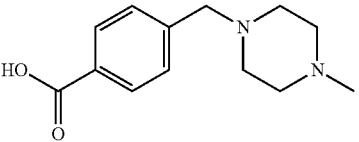 | 5-{2-Methyl-5-[4-(4-methyl-piperazin-1-ylmethyl)-benzoylamino]-phenoxymethyl}-1H-pyrrolo[2,3-b]pyridine-2-carboxylic acid methyl ester 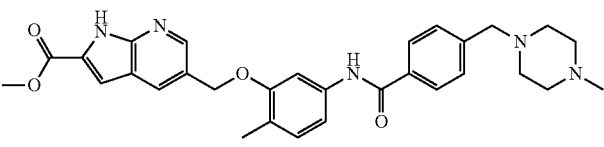 Yield: 5% ¹H NMR (400 MHz, DMSO) δ 10.13 (s, 1H), 8.55 (d, J = 1.6, 1H), 8.22 (d, J = 1.6, 1H), 7.90 (d, J = 8.2, 2H), 7.64 (d, J = 1.5, 1H), 7.43 (d, J = 8.2, 2H), 7.30 (dd, J = 1.5, 8.1, 1H), 7.20 (s, 1H), 7.10 (d, J = 8.1, 1H), 5.19 (s, 2H), 3.88 (s, 3H), 3.55-3.50 (m, 2H), 2.44-2.24 (m, 8H), 2.15 (s, 3H), 2.13 (s, 3H) HPLC: 99%; MS: 528 (M + 1) |
| OR0749 | 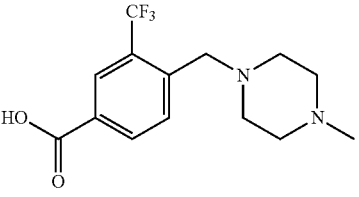 | 5-{2-Methyl-5-[4-(4-methyl-piperazin-1-ylmethyl)-3-trifluoromethyl-benzoylamino]-phenoxymethyl}-1H-pyrrolo[2,3-b]pyridine-2-carboxylic acid methyl ester 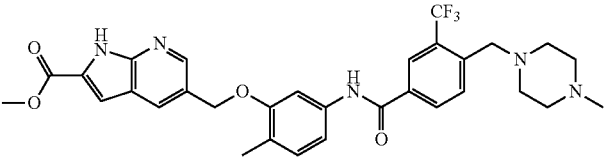 Yield: 60% ¹H NMR (400 MHz, DMSO) δ 12.58 (s, 1H), 10.37 (s, 1H), 8.56 (d, 1H), 8.25 (d, J = 7.9, 1H), 8.24 (s, 1H), 7.92 (d, J = 7.9, 1H), 7.62 (s, 1H), 7.29 (d, J = 8.3, 1H), 7.21 (d, 1H), 7.13 (d, J = 8.3, 1H), 5.21 (s, 2H), 3.88 (s, 3H), 3.68 (s, 2H), 2.49-2.24 (m, 8H), 2.17 (s, 3H), 2.15 (s, 3H) HPLC: 90%; MS: 596 (M + 1) |

TABLE 7-continued

Compounds obtained by example E

| Example No. | Used reagents | Synthesized inhibitors (mass and analytical data) |
|---|---|---|
| OR0750 | [structure: 4-((3-(dimethylamino)pyrrolidin-1-yl)methyl)-3-(trifluoromethyl)benzoic acid] | 5-{5-[4-(3-Dimethylamino-pyrrolidin-1-ylmethyl)-3-trifluoromethyl-benzoylamino]-2-methyl-phenoxymethyl}-1H-pyrrolo[2,3-b]pyridine-2-carboxylic acid methyl ester [structure]<br>Yield: 11%<br>$^1$H NMR (400 MHz, DMSO) δ 12.51 (s, 1H), 10.40 (s, 1H), 8.54 (s, 1H), 8.26-8.18 (m, 3H), 7.90 (d, J = 7.9, 1H), 7.63 (s, 1H), 7.30 (d, J = 7.8, 1H), 7.19 (s, 1H), 7.13 (d, J = 7.8, 1H), 5.20 (s, 2H), 3.87 (s, 3H), 3.81 (d, J = 14.2, 1H), 3.75 (d, J = 14.2, 1H), 2.81-2.57 (m, 4H), 2.43-2.33 (m, 1H), 2.14 (s, 3H), 2.09 (s, 6H), 1.96-1.80 (m, 1H), 1.74-1.57 (m, 1H)<br>HPLC: 98%; MS: 610 (M + 1) |

Example F

Synthesis of 2-acetyl-1H-pyrrolo[2,3-b]pyridine-5-carboxylic acid {5-benzoylamino-2-methyl-phenyl}-amides

Step 1: Protocol for the Preparation of 2-acetyl-1H-pyrrolo[2,3-b]pyridine-5-carboxylic acid 2-acetyl-1H-pyrrolo[2,3-b]pyridine-5-carbonitrile (10 mg, 0.054 mol) in dioxane (500 μL) was added in a schlenk Scheme 35 - General synthesis scheme of Example F

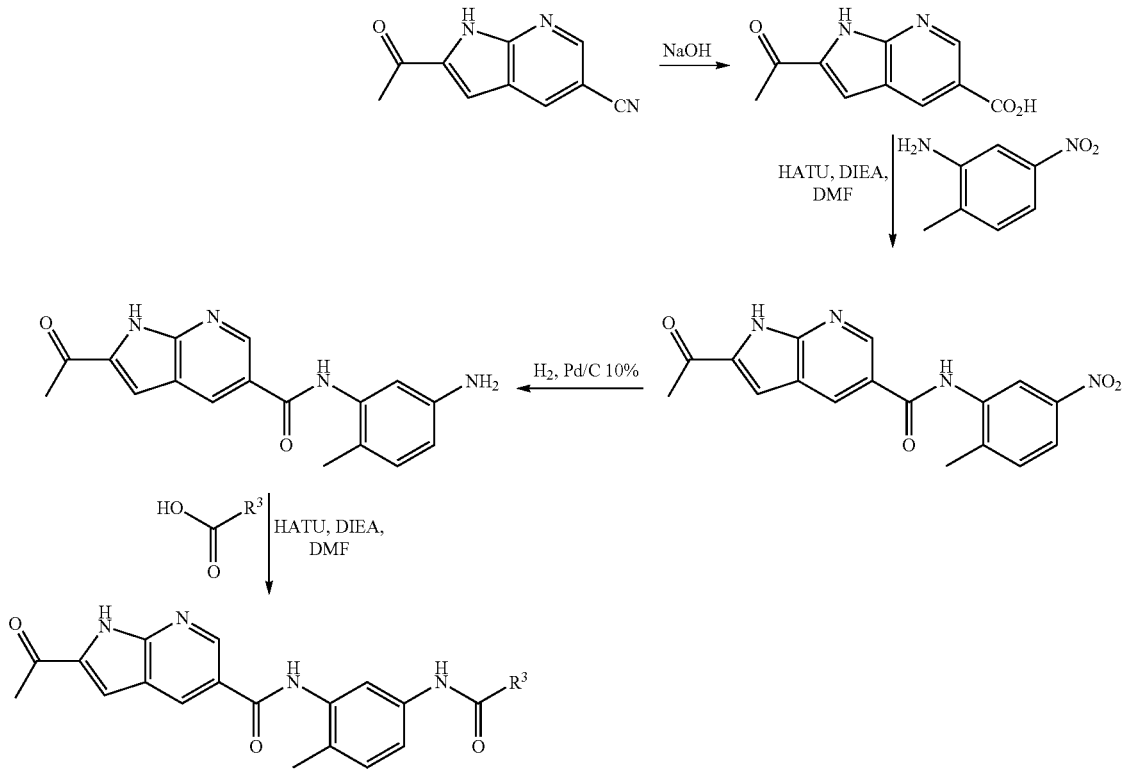

flask with NaOH (164 μL). The reaction was stirred and reflux for 3 h, then, solvents were evaporated under reduce pressure and H₂O with HCl 6N was added to pH 2-3. The precipitate was filtered to give a brown solid.

Yield=96%. ¹H NMR (300 MHz, DMSO) δ 12.89 (s, 1H), 9.17 (d, J=1.85, 1H), 8.92 (d, J=1.85, 1H), 7.72 (s, 1H), 2.81 (s, 3H). ESI-MS: m/z 205 ([M+H]⁺). HPLC purity: 98%.

Step 2: Protocol for the Preparation of 2-acetyl-1H-pyrrolo[2,3-b]pyridine-5-carboxylic acid (2-methyl-5-nitro-phenyl)-amide 2-Acetyl-1H-pyrrolo[2,3-b]pyridine-5-carboxylic acid was dissolved in anhydrous DMF (0.06 mol/L) with DIEA (5 eq) and HATU (2 eq). After 15 min, 2-methyl-5-nitro-phenylamine was slowly added and mixture was stirred for 12 h at RT. DMF was evaporated and NaHCO₃₍ₐq₎ was added. Product was extracted with EtOAc, dried, filtered and evaporated to obtain a dark mixture. After purification by washing with MeOH or EtOAc or by silica column, expected product was obtained.

Yield=90%. ESI-MS: m/z 309 ([M+H]⁺).

Step 3: Protocol for the Preparation of 2-acetyl-1H-pyrrolo[2,3-b]pyridine-5-carboxylic acid (5-amino-2-methyl-phenyl)-amide 2-acetyl-1H-pyrrolo[2,3-b]pyridine-5-carboxylic acid (2-methyl-5-nitro-phenyl)-amide was dissolved in DMF, introduced in a reactor with 10% Pd/C and stirred for 16 hours under 10 bar of hydrogen. Reaction mixture was then filtered on celite and concentrated to afford the desired compound.

Yield=90%. ESI-MS: m/z 309 ([M+H]⁺).

Step 4: General Protocol for the Preparation of 2-Acetyl-1H-pyrrolo[2,3-b]pyridine-5-carboxylic acid {5-benzoylamino-2-methyl-phenyl}-amides Acid derivative was dissolved in anhydrous DMF (0.06 mol/L) with DIEA (5 eq) and HATU (2 eq). After 15 min, 2-acetyl-1H-pyrrolo[2,3-b]pyridine-5-carboxylic acid (5-amino-2-methyl-phenyl)-amide was slowly added and mixture was stirred for 12 h at RT. DMF was evaporated and NaHCO₃₍ₐq₎ was added. Product was extracted with EtOAc, dried, filtered and evaporated to obtain a dark mixture. After purification by washing with MeOH or EtOAc or by silica column, expected product was obtained.

Table 8 shows the compounds synthesized according to the synthesis Scheme 35 described above.

TABLE 8

Compounds obtained by example F

| Example No. | Used reagents | Synthesized inhibitors (mass and analytical data) |
|---|---|---|
| OR0724 | [structure: 4-(hydroxycarbonyl)-2-trifluoromethyl benzyl-4-methylpiperazine] | 2-Acetyl-1H-pyrrolo[2,3-b]pyridine-5-carboxylic acid {2-methyl-5-[4-(4-methyl-piperazin-1-ylmethyl)-3-trifluoromethyl-benzoylamino]-phenyl}-amide [structure] Yield: 12% ¹H NMR (400 MHz, DMSO) δ 12.61 (s, 1H), 10.44 (s, 1H), 10.05 (s, 1H), 9.03 (s, 1H), 8.78 (s, 1H), 8.25 (s, 1H), 8.23 (d, J = 8.4, 1H), 7.92 (d, J = 7.9, 1H), 7.88 (s, 1H), 7.61 (d, J = 7.9, 1H), 7.53 (s, 1H), 7.28 (d, J = 8.4, 1H), 3.68 (s, 2H), 2.61 (s, 3H), 2.48-2.32 (m, 8H), 2.26 (s, 3H), 2.19 (s, 3H) HPLC: 98%; MS: 593 (M + 1) |
| OR0723 | [structure: 3-(4-methyl-imidazol-1-yl)-5-trifluoromethyl benzoic acid] | 2-Acetyl-1H-pyrrolo[2,3-b]pyridine-5-carboxylic acid {2-methyl-5-[3-(4-methyl-imidazol-1-yl)-5-trifluoromethyl-benzoylamino]-phenyl}-amide [structure] Yield: 4% ¹H NMR (600 MHz, DMSO) δ 12.61 (s, 1H), 10.58 (s, 1H), 10.08 (s, 1H), 9.04 (d, J = 2.0, 1H), 8.78 (d, J = 2.0, 1H), 8.49 (s, 1H), 8.41 (s, 1H), 8.23 (s, 1H), 8.18 (s, 1H), 7.89 (d, J = 1.8, 1H), 7.72 (s, 1H), 7.65 (dd, J = 1.8, 8.4, 1H), 7.53 (s, 1H), 7.30 (d, J = 8.4, |

| Example No. | Used reagents | Synthesized inhibitors (mass and analytical data) |
|---|---|---|
| | | 1H), 2.61 (s, 3H), 2.27 (s, 3H), 2.19 (s, 3H)<br>HPLC: 94%; MS: 561 (M + 1) |

Compounds obtained by example F

TABLE 8-continued

Example G

Synthesis of N-{3-[2-(2-acetyl-1H-pyrrolo[2,3-b]pyridin-5-yl)-ethyl]-4-methyl-phenyl}-benzamides

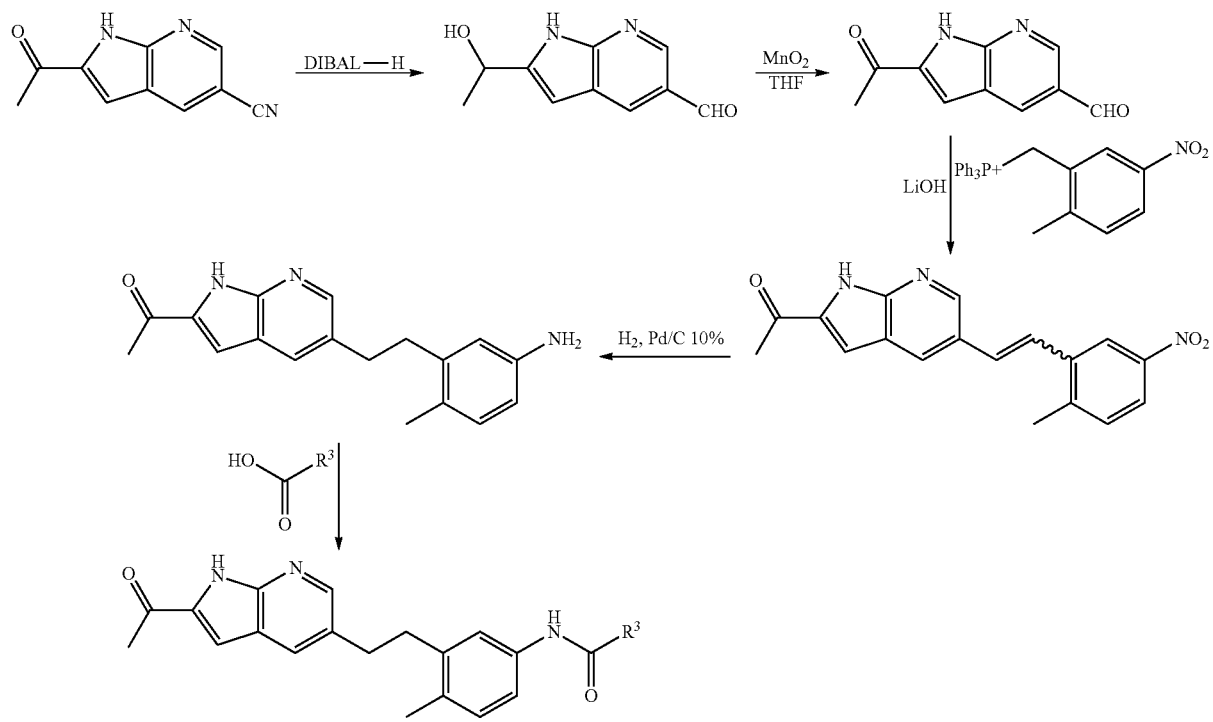

Scheme 36 - General synthesis scheme of example G

Step 1: Protocol for the Preparation of 2-(1-hydroxy-ethyl)-1H-pyrrolo[2,3-b]pyridine-5-carbaldehyde 2-acetyl-1H-pyrrolo[2,3-b]pyridine-5-carbonitrile (4 g) was dissolved in dry toluene and stirred at 0° C., then DIBAL-H (1 M, 3 eq) was added dropwise and allowed to stir at 0° C. for 1.5 hours. 85 ml of MeOH was slowly added, followed by 25.5 ml of a 2 M solution of $H_2SO_4$. The aluminum salts were filtered off, the filtrate was concentrated and the residue purified by column chromatography to give a yellow solid.

Yield=31%. ESI-MS: m/z 191 ([M+H]$^+$). HPLC purity: 99%.

Step 2: Protocol for the Preparation of 2-acetyl-1H-pyrrolo[2,3-b]pyridine-5-carbaldehyde 2-(1-Hydroxy-ethyl)-1H-pyrrolo[2,3-b]pyridine-5-carbaldehyde (1.3 g) was dissolved in THF, $MnO_2$ (12 eq) was added and the mixture was stirred overnight at RT. The $MnO_2$ is eliminated by filtration on celite, rinsed by hot methanol and DMF. The filtrate was concentrated to give an off-white solid.

Yield=65%. ESI-MS: m/z 189 ([M+H]$^+$). HPLC purity: 98.5%.

Step 3: Protocol for the Preparation of 1-{5-[-2-(2-methyl-5-nitro-phenyl)-vinyl]-1H-pyrrolo[2,3-b]pyridin-2-yl}-ethanone 2-acetyl-1H-pyrrolo[2,3-b]pyridine-5-carbaldehyde (844 mg) was added in a dried flask with (2-methyl-5-nitro-benzyl)-triphenyl-phosphonium (1.1 eq), LiOH (2 eq) in anhydrous MeOH (30 mL) and the reaction was stirred at RT overnight. The crude mixture was basified with $NH_4Cl$ to pH 7 and the precipitate was filtered and washed with $Et_2O$ to obtain a yellow powder.

Yield=71%. ESI-MS: m/z 322 ([M+H]$^+$). HPLC purity: 90%.

Step 4: Protocol for the Preparation of 1-{5-[2-(5-amino-2-methyl-phenyl)-ethyl]-1H-pyrrolo[2,3-b]pyridin-2-yl}-ethanone 1-{5-[-2-(2-methyl-5-nitro-phenyl)-vinyl]-1H-pyrrolo[2,3-b]pyridin-2-yl}-ethanone was dissolved in DMF, introduced in a reactor with 10% Pd/C and stirred overnight under 10 bar of hydrogen. Reaction mixture was then filtered on celite and concentrated to afford a brown powder which was further purified on reverse phase to obtain the expected product as a off-white solid.

Yield=38%. ESI-MS: m/z 294 ([M+H]$^+$). HPLC purity: 93%.

Step 5: General protocol for the preparation of N-{3-[2-(2-acetyl-1H-pyrrolo[2,3-b]pyridin-5-yl)-ethyl]-4-methyl-phenyl}-benzamides Acid derivative was dissolved in anhydrous DMF (0.06 mol/L) with DIEA (5 eq) and HATU (2 eq). After 15 min, 1-{5-[2-(5-amino-2-methyl-phenyl)-ethyl]-1H-pyrrolo[2,3-b]pyridin-2-yl}-ethanone was slowly added and mixture was stirred for 12 h at RT. DMF was evaporated and NaHCO$_{3(aq)}$ was added. Product was extracted with EtOAc, dried, filtered and evaporated to obtain a dark mixture. After purification by washing with MeOH or EtOAc or by silica column, expected product was obtained.

Table 9 shows the compounds synthesized according to the synthesis Scheme 36 described above.

TABLE 9

| | Compounds obtained by example G | |
|---|---|---|
| Example No. | Used reagents | Synthesized inhibitors (mass and analytical data) |
| OR1061 | 3-hydroxy-4-trifluoromethyl-benzoic acid (structure) | N-{3-[2-(2-Acetyl-1H-pyrrolo[2,3-b]pyridin-5-yl)-ethyl]-4-methyl-phenyl}-3-hydroxy-4-trifluoromethyl-benzamide<br>Yield: 12%<br>$^1$H NMR (300 MHz, DMSO) δ 12.18 (s, 1H), 11.27 (s, 1H), 10.10 (s, 1H), 8.32 (d, J = 2.1, 1H), 8.18 (d, J = 1.8, 1H), 8.09 (dd, J = 1.8, 8.6, 1H), 7.98 (d, J = 1.8, 1H), 7.60 (d, J = 2.0, 1H), 7.52 (dd, J = 2.0, 8.4, 1H), 7.29 (d, J = 2.1, 1H), 7.13 (d, J = 8.4, 1H), 7.10 (d, J = 8.6, 1H), 3.01-2.84 (m, 4H), 2.55 (s, 3H), 2.21 (s, 3H)<br>HPLC: 91%; MS: 482 (M + 1) |
| OR0799 | 4-(4-methyl-piperazin-1-ylmethyl)-benzoic acid (structure) | N-{3-[2-(2-Acetyl-1H-pyrrolo[2,3-b]pyridin-5-yl)-ethyl]-4-methyl-phenyl}-4-(4-methyl-piperazin-1-ylmethyl)-benzamide<br>Yield: 55%<br>$^1$H NMR (300 MHz, DMSO) δ 12.16 (s, 1H), 10.07 (s, 1H), 8.32 (s, 1H), 7.98 (s 1H), 7.90 (d, J = 8.3, 2H), 7.63 (s, 1H), 7.53 (dd, J = 2.0, 8.2, 1H), 7.43 (d, J = 8.3, 2H), 7.29 (d, J = 2.0, 1H), 7.10 (d, J = 8.4, 1H), 3.53 (s, 2H), 3.02-2.85 (m, 4H), 2.55 (s, 3H), 2.38 (s, 8H), 2.21 (s, 3H), 2.17 (s, 3H)<br>HPLC: >99%; MS: 510 (M + 1) |

TABLE 9-continued

Compounds obtained by example G

| Example No. | Used reagents | Synthesized inhibitors (mass and analytical data) |
|---|---|---|
| OR0797 | 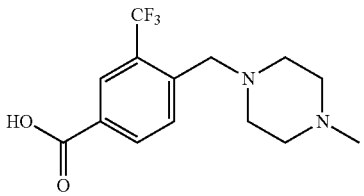 | N-{3-[2-(2-Acetyl-1H-pyrrolo[2,3-b]pyridin-5-yl)-ethyl]-4-methyl-phenyl}-4-(4-methyl-piperazin-1-ylmethyl)-3-trifluoromethyl-benzamide<br>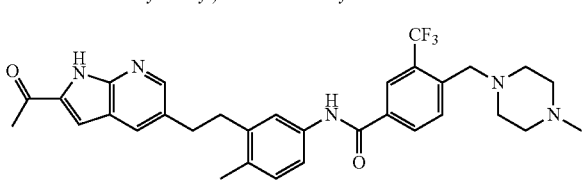<br>Yield: 19%<br>$^1$H NMR (300 MHz, DMSO) δ 12.16 (s, 1H), 10.32 (s, 1H), 8.32 (s, 1H), 8.26-8.17 (m, 2H), 7.98 (s, 1H), 7.91 (d, 1H), 7.60 (s, 1H), 7.54 (d, 1H), 7.29 (s, 1H), 7.12 (d, 1H), 3.68 (s, 2H), 3.03-2.83 (m, 4H), 2.54 (s, 3H), 2.48-2.30 (m, 8H), 2.22 (s, 3H), 2.19 (s, 3H)<br>HPLC: 98%; MS: 578 (M + 1) |
| OR1059 | 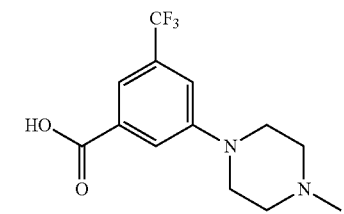 | N-{3-[2-(2-Acetyl-1H-pyrrolo[2,3-b]pyridin-5-yl)-ethyl]-4-methyl-phenyl}-3-(4-methyl-piperazin-1-yl)-5-trifluoromethyl-benzamide<br>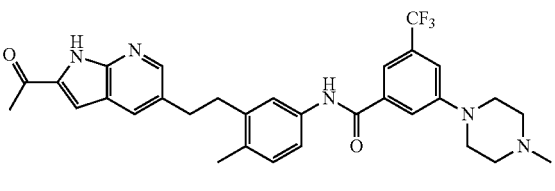 [SMILES: CC(=O)c1cc2cc(CCc3cc(NC(=O)c4cc(N5CCN(C)CC5)cc(C(F)(F)F)c4)ccc3C)cnc2[nH]1]<br>Yield: 20%<br>$^1$H NMR (300 MHz, DMSO) δ 12.17 (s, 1H), 10.24 (s, 1H), 8.32 (s, 1H), 7.98 (s, 1H), 7.72 (s, 1H), 7.64 (s, 1H), 7.59 (s, 1H), 7.54 (dd, J = 1.8, 8.2, 1H), 7.39 (s, 1H), 7.29 (d, J = 1.8, 1H), 7.13 (d, J = 8.2, 1H), 3.39 (bs, 4H), 3.01-2.84 (m, 4H), 2.64 (bs, 4H), 2.55 (s, 3H), 2.36 (s, 3H), 2.22 (s, 3H)<br>HPLC: 98%; MS: 546 (M + 1) |
| OR0798 | 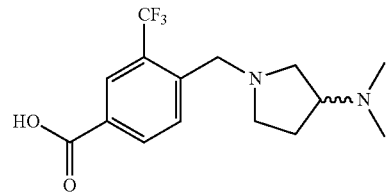 | N-{3-[2-(2-Acetyl-1H-pyrrolo[2,3-b]pyridin-5-yl)-ethyl]-4-methyl-phenyl}-4-(3-dimethylamino-pyrrolidin-1-ylmethyl)-3-trifluoromethyl-benzamide<br>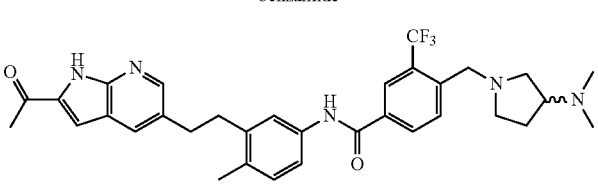<br>Yield: 15%<br>$^1$H NMR (300 MHz, DMSO) δ 12.16 (s, 1H), 10.32 (s, 1H), 8.32 (s, 1H), 8.27-8.18 (m, 2H), 7.98 (s, 1H), 7.89 (d, 1H), 7.61 (s, 1H), 7.54 (d, 1H), 7.29 (s, 1H), 7.13 (d, 1H), 3.88-3.70 (m, 2H), 2.99-2.84 (m, 4H), 2.72-2.64 (m, 1H), 2.61-2.50 (m, 6H), 2.44 (s, 1H), 2.22 (s, 3H), 2.16 (s, 6H), 2.00-1.84 (m, 1H), 1.76-1.62 (m, 1H)<br>HPLC: 96%; MS: 592 (M + 1) |

TABLE 9-continued

Compounds obtained by example G

| Example No. | Used reagents | Synthesized inhibitors (mass and analytical data) |
|---|---|---|
| OR0812 | [structure: 4-((S)-3-(dimethylamino)pyrrolidin-1-ylmethyl)-3-trifluoromethyl-benzoic acid] | N-{3-[2-(2-Acetyl-1H-pyrrolo[2,3-b]pyridin-5-yl)-ethyl]-4-methyl-phenyl}-4-((S)-3-dimethylamino-pyrrolidin-1-ylmethyl)-3-trifluoromethyl-benzamide<br>[structure]<br>Yield: 45%<br>$^1$H NMR (300 MHz, DMSO) δ 12.16 (s, 1H), 10.32 (s, 1H), 8.32 (s, 1H), 8.23 (s, 1H), 8.22 (d, J = 8.2, 1H), 7.98 (s, 1H), 7.89 (d, J = 7.6, 1H), 7.60 (s, 1H), 7.54 (d, J = 7.6, 1H), 7.29 (s, 1H), 7.13 (d, J = 8.2, 1H), 3.83 (d, J = 14.0, 1H), 3.75 (d, J = 14.0, 1H), 3.00-2.84 (m, 4H), 2.84-2.58 (m, 4H), 2.54 (s, 3H), 2.44-2.35 (m, 1H), 2.22 (s, 3H), 2.11 (s, 6H), 1.97-1.82 (m, 1H), 1.73-1.55 (m, 1H)<br>HPLC: 97%; MS: 592 (M + 1) |
| OR0800 | [structure: 5-trifluoromethyl-nicotinic acid] | N-{3-[2-(2-Acetyl-1H-pyrrolo[2,3-b]pyridin-5-yl)-ethyl]-4-methyl-phenyl}-5-trifluoromethyl-nicotinamide<br>[structure]<br>Yield: 6%<br>$^1$H NMR (400 MHz, DMSO) δ 12.16 (s, 1H), 10.50 (s, 1H), 9.37 (s, 1H), 9.18 (s, 1H), 8.68 (s, 1H), 8.32 (s, 1H), 7.98 (d, 1H), 7.61 (d, 1H), 7.55 (dd, 1H), 7.29 (d, 1H), 7.15 (d, 1H), 3.01-2.88 (m, 4H), 2.55 (s, 3H), 2.23 (s, 3H)<br>HPLC: 100%; MS: 467 (M + 1) |
| OR0966 | [structure: 2-(3-trifluoromethylphenyl)-acetic acid] | N-{3-[2-(2-Acetyl-1H-pyrrolo[2,3-b]pyridin-5-yl)-ethyl]-4-methyl-phenyl}-2-(3-trifluoromethyl-phenyl)-acetamide<br>[structure]<br>Yield: 54%<br>$^1$H NMR (300 MHz, DMSO) δ 12.16 (s, 1H), 10.09 (s, 1H), 8.29 (s, 1H), 7.95 (s, 1H), 7.69 (s, 1H), 7.66-7.50 (m, 3H), 7.43 (d, J = 1.9, 1H), 7.34 (dd, J = 1.9, 8.2, 1H), 7.27 (d, J = 1.9, 1H), 7.05 (d, J = 8.2, 1H), 3.75 (s, 2H), 2.98-2.76 (m, 4H), 2.55 (s, 3H), 2.18 (s, 3H)<br>HPLC: 97%; MS: 480 (M + 1) |

TABLE 9-continued

Compounds obtained by example G

| Example No. | Used reagents | Synthesized inhibitors (mass and analytical data) |
|---|---|---|
| OR1086 | 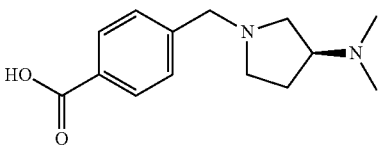 | N-{3-[2-(2-Acetyl-1H-pyrrolo[2,3-b]pyridin-5-yl)-ethyl]-4-methyl-phenyl}-4-((S)-3-dimethylamino-pyrrolidin-1-ylmethyl)-benzamide 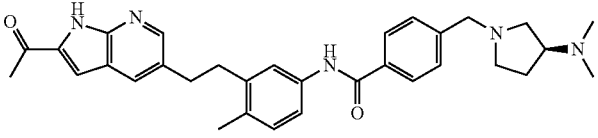 [SMILES: CC(=O)c1cc2cc(CCc3cc(NC(=O)c4ccc(CN5CC[C@H](N(C)C)C5)cc4)ccc3C)cnc2[nH]1] Yield: 10% $^1$H NMR (300 MHz, DMSO) δ 12.16 (s, 1H), 10.32 (s, 1H), 8.32(s, 1H), 7.98 (s 1H), 7.90 (d, J = 8.3, 2H), 7.63 (s, 1H), 7.53 (dd, J = 2.0, 8.3, 1H), 7.43 (d, J = 8.3, 2H), 7.29 (d, J = 2.0, 1H), 7.10 (d, J = 8.4, 1H), 3.75 (d, J = 14.0, 1H), 3.53 (d, J = 14.0, 1H), 3.00-2.84 (m, 4H), 2.84-2.58 (m, 4H), 2.54 (s, 3H), 2.44-2.35 (m, 1H), 2.22 (s, 3H), 2.11 (s, 6H), 1.97-1.82 (m, 1H), 1.73-1.55 (m, 1H) HPLC: 95%; MS: 524 (M + 1) |

Example H

Synthesis of Thioamide Derivatives

General method to synthesize thioamide derivatives is represented by Scheme 37.

Scheme 37 - General synthesis scheme of example H

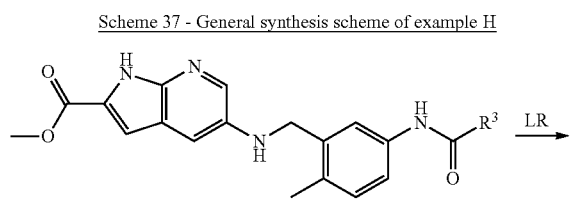

LR

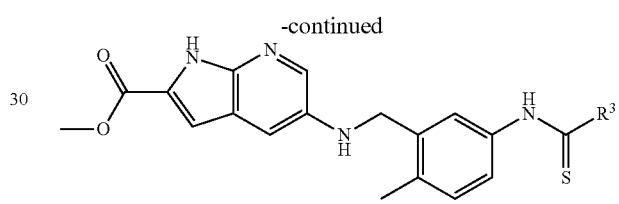

-continued

General Procedure for the Synthesis of Thioamide Starting from Amide Derivatives:

A suspension of amide derivative (100 mg) and Lawesson's reagent ("LR" in Scheme 23) (1.8 eq) in 5 mL of chlorobenzene was heated at 130° C. for 2 hours. The solvent is evaporated and the residue is purified by silica gel chromatography (water+1% TFA/acetonitrile+1% TFA). After evaporation of the solvent, the residue is dissolved in water, basified to pH 7-8 by NaHCO$_3$ and extract by AcOEt. The organic layer is then dried over Na$_2$SO$_4$ and the solvent removed to give a yellow solid.

Table 10 shows the compounds synthesized according to the synthesis Scheme 37 described above.

TABLE 10

Compounds obtained by example H

| Example No. | Synthesized inhibitors (mass and analytical data) |
|---|---|
| OR0969 | 5-(2-{2-Methyl-5-[4-(4-methyl-piperazin-1-ylmethyl)-thiobenzoylamino]-phenyl}-ethyl)-1H-pyrrolo[2,3-b]pyridine-2-carboxylic acid methyl ester 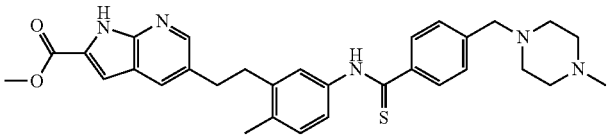 Yield: 29% |

TABLE 10-continued

Compounds obtained by example H

| Example No. | Synthesized inhibitors (mass and analytical data) |
|---|---|
| | $^1$H NMR (400 MHz, DMSO) δ 12.40 (s, 1H), 11.60 (s, 1H), 8.33 (d, J = 2.2, 1H), 7.97 (s, 1H), 7.77 (d, J = 8.2, 2H), 7.67 (d, J = 2.0, 1H), 7.54 (dd, J = 2.0, 8.0, 1H), 7.36 (d, J = 8.2, 2H), 7.18 (d, J = 8.0, 1H), 7.11 (d, J = 2.2, 1H), 3.87 (s, 3H), 3.51 (s, 2H), 3.00-2.86 (m, 4H), 2.49-2.26 (m, 8H), 2.25 (s, 3H), 2.17 (s, 3H) HPLC: >99%; MS: 542 (M + 1) |
| OR1014 | 5-(2-{3-[2-(3-Trifluoromethyl-phenyl)-thioacetylamino]-phenyl}-ethyl)-1H-pyrrolo[2,3-b]pyridine-2-carboxylic acid methyl ester 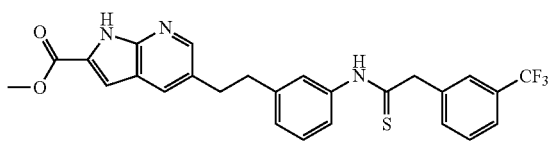 [SMILES: COC(=O)c1cc2cc(CCc3cccc(NC(=S)Cc4cccc(C(F)(F)F)c4)c3)cnc2[nH]1] Yield: 10% $^1$H NMR (300 MHz, DMSO) δ 12.34 (s, 1H), 11.82 (s, 1H), 8.28 (s, 1H), 7.93 (d, J = 1.1, 1H), 7.77 (s, 1H), 7.72 (d, J = 7.6, 1H), 7.68-7.53 (m, 4H), 7.29 (t, J = 7.6, 1H), 7.13-7.06 (m, 2H), 4.18 (s, 2H), 3.87 (s, 3H), 2.97 (s, 4H) HPLC: 77%; MS: 498 (M + 1) |

Example I

Synthesis of Ureido Derivatives

General method to synthesize ureido derivatives is represented by Scheme 38:

Scheme 38 - General synthesis scheme of example I

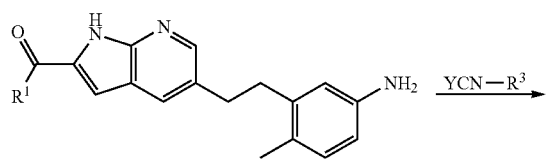 →YCN—R³

-continued

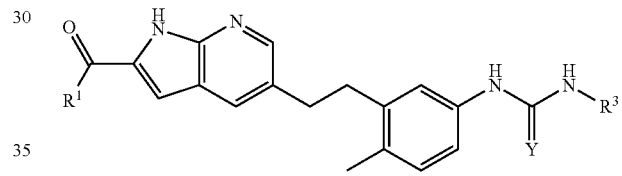

General Protocol for the Preparation of Ureido Derivatives.

To a solution of amino derivative was added the isocyanate or isothiocyanate reagent (1 eq). The mixture was allowed to stir at RT overnight. The solvent was removed and the crude product was purified by silica gel chromatography.

Table 11 shows the compounds synthesized according to the synthesis described above in Scheme 38.

TABLE 11

Compounds obtained by example I

| Example No. | Used reagents | Synthesized inhibitors (mass and analytical data) |
|---|---|---|
| OR0918 | OCN—⟨⟩—CF₃ | 5-(2-{2-Methyl-5-[3-(3-trifluoromethyl-phenyl)-ureido]-phenyl}-ethyl)-1H-pyrrolo[2,3-b]pyridine-2-carboxylic acid methyl ester 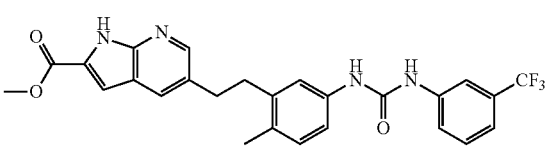 [SMILES: COC(=O)c1cc2cc(CCc3cc(NC(=O)Nc4cccc(C(F)(F)F)c4)ccc3C)cnc2[nH]1] Yield: 37% $^1$H NMR (300 MHz, DMSO) δ 12.39 (s, 1H), 8.96 (s, 1H), 8.61 (s, 1H), 8.31 (s, 1H), 8.02 (s, 1H), 7.97 (s, 1H), 7.59-7.43 (m, 2H), 7.30 (bs, 2H), 7.20 (dd, J = 2.0, 8.0, |

TABLE 11-continued

Compounds obtained by example I

| Example No. | Used reagents | Synthesized inhibitors (mass and analytical data) |
|---|---|---|
| | | 1H), 7.11 (d, J = 2.0, 1H), 7.05 (d, J = 8.0, 1H), 3.87 (s, 3H), 3.04-2.78 (m, 4H), 2.20 (s, 3H)<br>HPLC: 96%; MS: 497 (M + 1) |
| OR0919 | | 1-{3-[2-(2-Acetyl-1H-pyrrolo[2,3-b]pyridin-5-yl)-ethyl]-4-methyl-phenyl}-3-(3-trifluoromethyl-phenyl)-urea<br><br>Yield: 43%<br>$^{1}$H NMR (300 MHz, DMSO) δ 12.12 (s, 1H), 8.93 (s, 1H), 8.58 (s, 1H), 8.26 (s, 1H), 7.98 (s, 1H), 7.93 (s, 1H), 7.56-7.38 (m, 2H), 7.24 (bs, 3H), 7.16 (dd, J = 1.9, 8.1, 1H), 7.00 (d, J = 8.1, 1H), 2.98-2.76 (m, 4H), 2.50 (s, 3H), 2.14 (s, 3H)<br>HPLC: >99%; MS: 481 (M + 1) |
| OR1017 | | 1-{3-[2-(2-Acetyl-1H-pyrrolo[2,3-b]pyridin-5-yl)-ethyl]-4-methyl-phenyl}-3-(3-trifluoromethyl-phenyl)-thiourea<br><br>Yield: 26%<br>$^{1}$H NMR (300 MHz, DMSO) δ 12.20 (s, 1H), 9.93 (s, 1H), 9.90 (s, 1H), 8.35 (s, 1H), 8.00 (s, 1H), 7.97 (s, 1H), 7.74 (d, J = 7.9, 1H), 7.54 (t, J = 7.9, 1H), 7.44 (d, J = 7.9, 1H), 7.34-7.24 (m, 2H), 7.20 (dd, J = 2.0, 8.2, 1H), 7.11 (d, J = 8.2, 1H), 2.91 (d, J = 4.2, 4H), 2.55 (s, 3H), 2.22 (s, 3H)<br>HPLC: 98%; MS: 497 (M + 1) |

Example J

Synthesis of Benzenesulfonamide Derivatives

General method to synthesize benzenesulfonamide derivatives is represented by Scheme 39:

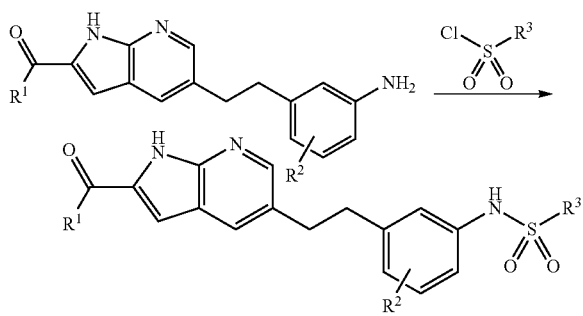

Scheme 39 - General synthesis scheme of example J

Synthesis of N-{3-[2-(2-Acetyl-1H-pyrrolo[2,3-b]pyridin-5-yl)-ethyl]-4-methyl-phenyl}-3-trifluoromethyl-benzenesulfonamide 20 μL of trimethylamine (1.1 eq) is added to a cold solution of 1-{5-[2-(5-Amino-2-methyl-phenyl)-ethyl]-1H-pyrrolo[2,3-b]pyridin-2-yl}-ethanone (40 mg, 0.13 mmol) in 2 mL of anhydrous DMF. A cold solution of sulfonyl chloride derivative (1.2 eq) in 2 mL of anhydrous DMF is then added dropwise. The reaction mixture is stirred at 0° C. for 30 minutes and overnight at RT. DMF is evaporated, then saturated NaHCO$_3$ solution is added. The solid obtained is filtrated, washed with water to obtain a yellow solid.

Table 12 shows the compounds synthesized according to the synthesis described above in Scheme 39.

TABLE 12

Compound obtained by example J

| Example No. | Used reagents | Synthesized inhibitors (mass and analytical data) |
|---|---|---|
| OR0967 | 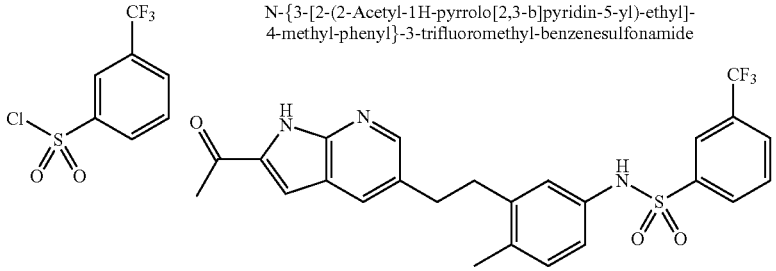 | N-{3-[2-(2-Acetyl-1H-pyrrolo[2,3-b]pyridin-5-yl)-ethyl]-4-methyl-phenyl}-3-trifluoromethyl-benzenesulfonamide<br><br>Yield: 64%<br>$^1$H NMR (300 MHz, DMSO) δ 12.16 (s, 1H), 10.21 (s, 1H), 8.20 (d, J = 2.0, 1H), 8.01 (d, J = 8.1, 2H), 7.95 (d, J = 7.6, 1H), 7.84 (d, J = 1.6, 1H), 7.78 (t, J = 7.7, 1H), 7.25 (d, J = 2.0, 1H), 6.98 (d, J = 8.2, 1H), 6.92 (d, J = 2.0, 1H), 6.78 (dd, J = 2.1, 8.1, 1H), 2.78 (s, 4H), 2.55 (s, 3H), 2.08 (s, 3H).<br>HPLC: 96%; MS: 502 (M + 1) |

Example K

Synthesis of 5-({3-[4-(4-Methyl-piperazin-1-ylmethyl)-3-trifluoromethyl-benzoylamino]-benzylamino}-methyl)-1H-pyrrolo[2,3-b]pyridine-2-carboxylic acid methyl ester

Scheme 40 - General synthesis scheme of example K

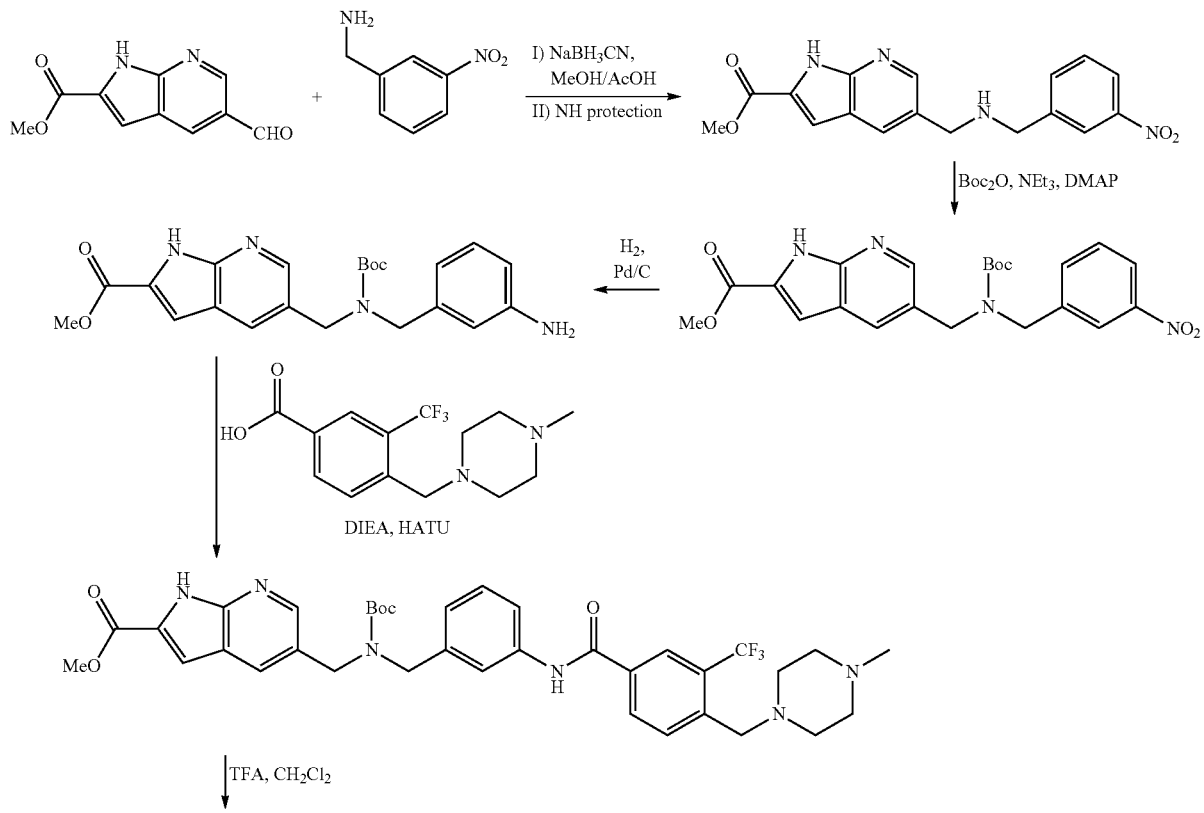

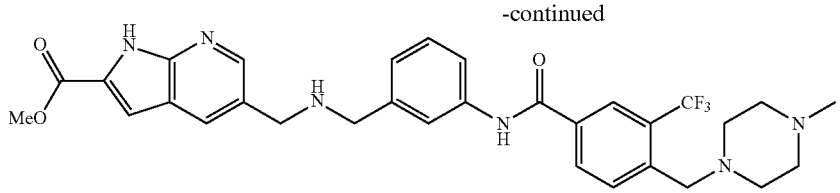

Step 1: Protocol for the Preparation of 5-[(3-Nitro-benzylamino)-methyl]-1H-pyrrolo[2,3-b]pyridine-2-carboxylic acid methyl ester Under argon, 5-formyl-1H-pyrrolo[2,3-b]pyridine-2-carboxylic acid methyl ester (1 eq) and 3-nitro-benzylamine (1 eq) were dissolved in MeOH with AcOH (10/1) and stirred at RT for 2 hours. NaBH$_3$CN (4 eq) was added over 4 days at RT. Then NaHCO3 was added to neutralize the mixture and MeOH was evaporated. The aqueous layer was extracted with AcOEt. The organic phase was evaporated and the crude was purified on reverse phase chromatography. White solid. Yield=33%. ESI-MS: m/z 341 ([M+H]$^+$). HPLC purity: 98%.

Step 2: Protocol for the preparation of 5-{[tert-Butoxycarbonyl-(3-nitro-benzyl)-amino]-methyl}-1H-pyrrolo[2,3-b]pyridine-2-carboxylic acid methyl ester 5-[(3-Nitro-benzylamino)-methyl]-1H-pyrrolo[2,3-b]pyridine-2-carboxylic acid methyl ester (1 eq) was dissolved in acetonitrile with triethylamine (2.5 eq). After 1 h stirring at RT, DMAP (0.03 eq) and Boc$_2$O (1 eq) were added and the mixture was stirred at RT overnight. 0.2 eq of BoC2O was added and the mixture was stirred 2 supplementary hours at RT. Then solvent was evaporated. NaHCO3 solution was added to crude and extracted with AcOEt. The organic layer was evaporated to give the expected product. Orange oil. Yield=39%. ESI-MS: m/z 441 ([M+H]$^+$).

Step 3: Protocol for the Preparation of 5-{[tert-Butoxycarbonyl-(3-amino-benzyl)-amino]-methyl}-1H-pyrrolo[2,3-b]pyridine-2-carboxylic acid methyl ester 5-{[tert-Butoxycarbonyl-(3-nitro-benzyl)-amino]-methyl}-1H-pyrrolo[2,3-b]pyridine-2-carboxylic acid methyl ester (1 eq) was dissolved in a mixture DMF/MeOH (2/1). Pd/C 10% (20% w) was added and the mixture was stirred at room temperature, overnight, under 30 bar of dihydrogene. Then Pd/C was filtered off and the solvents were evaporated to give the expected product.
Orange solid. Yield=93%. ESI-MS: m/z 411 ([M+H]$^+$).

Step 4: Protocol for the Preparation of 5-[(tert-Butoxycarbonyl-{3-[4-(4-methyl-piperazin-1-ylmethyl)-3-trifluoromethyl-benzoylamino]-benzyl}-amino)-methyl]-1H-pyrrolo[2,3-b]pyridine-2-carboxylic acid methyl ester 4-(4-methylpiperazin-1-ylmethyl)-3-trifluoromethyl-benzoic acid (1 eq, 0.1M) and HATU (2 eq) were dissolved in DMF and stirred at room temperature for 20 min. 5-{[tert-Butoxycarbonyl-(3-amino-benzyl)-amino]-methyl}-1H-pyrrolo[2,3-b]pyridine-2-carboxylic acid methyl ester (1 eq) and DIEA (4 eq) were added and the mixture was stirred overnight at RT. DMF is evaporated, NaHCO$_{3(aq)}$ is added, a precipitate occurred and filtered Black solid. Yield=quantitative, ESI-MS: m/z 695 ([M+H]$^+$).

Step 5: Protocol for the Preparation of 5-({3-[4-(4-Methyl-piperazin-1-ylmethyl)-3-trifluoromethyl-benzoylamino]-benzylamino}-methyl)-1H-pyrrolo[2,3-b]pyridine-2-carboxylic acid methyl ester 5-[(tert-Butoxycarbonyl-{3-[4-(4-methyl-piperazin-1-ylmethyl)-3-trifluoromethyl-benzoylamino]-benzyl}-amino)-methyl]-1H-pyrrolo[2,3-b]pyridine-2-carboxylic acid methyl ester (1 eq) was dissolved in dichloromethane (2 vol; 0.01M) and trifluoroacetic acid (1 vol) was added. The mixture was stirred at room temperature for 2 h. After evaporation of solvents, the crude was purified on reverse phase chromatography.

Table 13 shows the compounds synthesized according to the synthesis described above in Scheme 40.

TABLE 13

| Compound obtained by example K | |
|---|---|
| Example No. | Synthesized inhibitors (mass and analytical data) |
| OR1020 | 5-({3-[4-(4-Methyl-piperazin-1-ylmethyl)-3-trifluoromethyl-benzoylamino]-benzylamino}-methyl)-1H-pyrrolo[2,3-b]pyridine-2-carboxylic acid methyl ester |

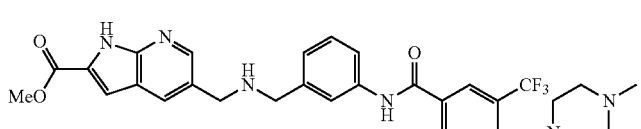

Yield: 18%
$^1$H NMR (400 MHz, MeOD) δ 8.40 (s, 1H), 8.26 (s, 1H), 8.16 (d, J = 8.2, 1H), 8.12 (s, 1H), 7.99 (d, J = 8.2, 1H), 7.68 (s, 1H),

TABLE 13-continued

Compound obtained by example K

| Example No. | Synthesized inhibitors (mass and analytical data) |
|---|---|
| | 7.62 (d, J = 7.9, 1H), 7.36 (t, J = 7.9, 1H), 7.23-7.14 (m, 2H), 3.94 (s, 3H), 3.89 (s, 2H), 3.81 (s, 2H), 3.76 (s, 2H), 2.55 (s, 8H), 2.30 (s, 3H) HPLC: >99%; MS: 595 (M + 1) |

Example L

Synthesis of 5-(2-{2-Methyl-5-[4-(4-methyl-piperazin-1-ylmethyl)-3-trifluoromethyl-benzoylamino]-phenyl}-ethyl)-1H-pyrrolo[2,3-b]pyridine-2-carboxylic acid Scheme 41 - General synthesis scheme of example L

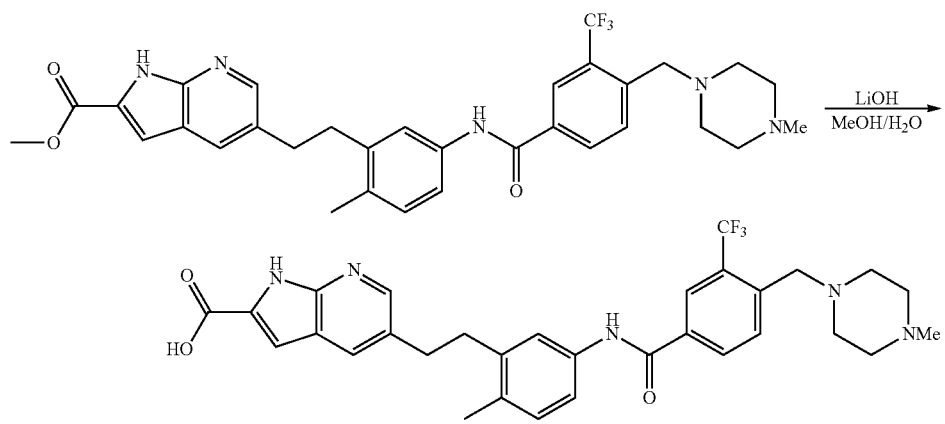

Protocol for the Preparation of 5-(2-{2-Methyl-5-[4-(4-methyl-piperazin-1-ylmethyl)-3-trifluoromethyl-benzoylamino]-phenyl}-ethyl)-1H-pyrrolo[2,3-b]pyridine-2-carboxylic acid Ester derivative is dissolved in MeOH/Water (1/1, 0.1 mol/L) and LiOH (3 eq) is added. Mixture was heated to reflux until complete reaction. MeOH was evaporated and aqueous layer is acidified until pH=7 with HCl 1 N. The obtained precipitate is filtered and washed with water and dried under vacuum.

Table 14 shows the compounds synthesized according to the synthesis described above in Scheme 41.

TABLE 14

Compound obtained by example L

| Example No. | Synthesized inhibitors (mass and analytical data) |
|---|---|
| OR1054 | 5-(2-{2-Methyl-5-[4-(4-methyl-piperazin-1-ylmethyl)-3-trifluoromethyl-benzoylamino]-phenyl}-ethyl)-1H-pyrrolo[2,3-b]pyridine-2-carboxylic acid 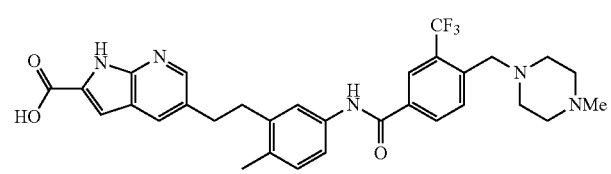 [SMILES: Cc1ccc(NC(=O)c2ccc(CN3CCN(C)CC3)c(C(F)(F)F)c2)cc1CCc1cnc2[nH]c(C(=O)O)cc2c1] Yield: 37% <br> ¹H NMR (400 MHz, DMSO) δ 12.04 (s, 1H), 10.32 (s, 1H), 8.27 (d, J = 1.9, 1H), 8.24 (s, 1H), 8.22 (d, J = 8.0, 1H), 7.94-7.89 (m, 2H), 7.61 (d, J = 1.9, 1H), 7.54 (dd, J = 2.0, 8.3, 1H),7.13 (d, J = 8.3, 1H), |

TABLE 14-continued

| | Compound obtained by example L |
|---|---|
| Example No. | Synthesized inhibitors (mass and analytical data) |
| | 6.97 (s, 1H), 3.68 (s, 2H), 2.98-2.85 (m, 4H), 2.46-2.31 (m, 8H), 2.23 (s, 3H), 2.20 (s, 3H) HPLC: 97%; MS: 580 (M + 1) |

Example M

Synthesis of 5-{[2-Methyl-5-(4-methyl-benzoylamino)-phenylamino]-methyl}-1H-pyrrolo[2,3-b]pyridine-2-carboxylic acid Scheme 42 - General synthesis scheme of example M

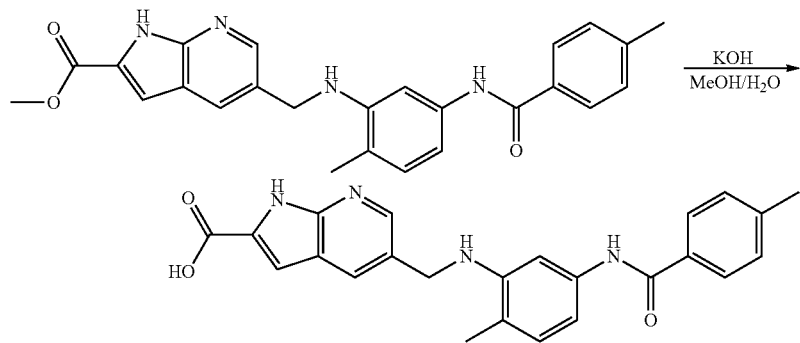

Protocol for the Preparation of 5-{[2-Methyl-5-(4-methyl-benzoylamino)-phenylamino]-methyl}-1H-pyrrolo[2,3-b]pyridine-2-carboxylic acid Ester derivative was dissolved in MeOH/Water (1/1, 0.1 mol/L) and KOH (85%, 3.5 eq) was added. Mixture was heated for 2 h at 65° C. MeOH was evaporated and aqueous layer was acidified until pH=2 with HCl 2N. The obtained precipitate is filtered and washed with water and dried under vacuum.

Table 15 shows the compounds synthesized according to the synthesis described above in Scheme 42.

TABLE 15

| | Compound obtained by example M |
|---|---|
| Example No. | Synthesized inhibitors (mass and analytical data) |
| OR1005 | 5-{[2-Methyl-5-(4-methyl-benzoylamino)-phenylamino]-methyl}-1H-pyrrolo[2,3-b]pyridine-2-carboxylic acid <br><br> Yield: 63% <br> $^1$H NMR (400 MHz, DMSO) δ 13.07 (bs, 1H), 12.24 (s, 1H), 9.80 (s, 1H), 8.46 (s, 1H), 8.05 (s, 1H), 7.78 (d, J = 8.0, 2H), 7.28 (d, J = 8.0, 2H), 7.08-7.03 (m, 2H), 7.01 (d, J = 8.2, 1H), 6.92 (d, J = 8.2, 1H), 5.62 (bs, 1H), 4.44 (s, 2H), 2.36 (s, 3H), 2.13 (s, 3H). <br> HPLC: 89%; MS: 415 (M + 1) |

Example N

Synthesis of 5-{[2-Methyl-5-(4-methyl-benzoylamino)-phenylamino]-methyl}-1H-pyrrolo[2,3-b]pyridine-2-carboxylic acid diethylamide Scheme 43 - General synthesis of example N

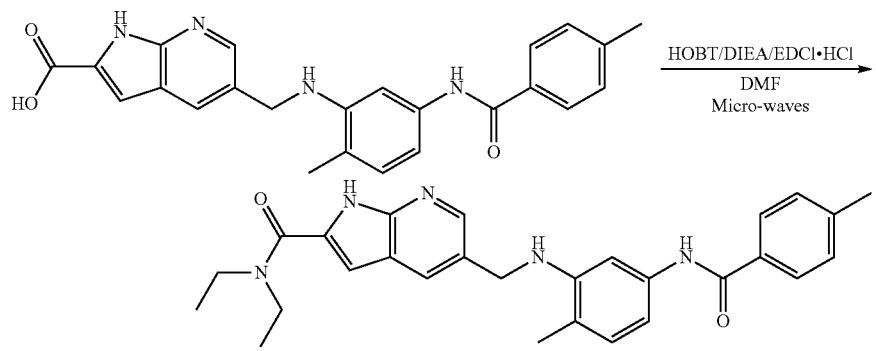

Protocol for the Preparation of 5-(2-{2-Methyl-5-[4-(4-methyl-piperazin-1-ylmethyl)-3-trifluoromethyl-benzoylamino]-phenyl}-ethyl)-1H-pyrrolo[2,3-b]pyridine-2-carboxylic acid diethylamide The acid derivative (1 eq) was dissolved in DMF (0.1M) with diethylamine (5 eq), DIEA (3 eq), HOBt (1.2 eq) and EDCI.HCl (1.2 eq). The mixture was heated by microwave irradiation at 140° C. for 5 min. The mixture was concentrated and washed with NaHCO3 saturated solution. The precipitate was filtered. The crude product was purified on reverse phase to give the final product.

Table 16 shows the compounds synthesized according to the synthesis described above in Scheme 43.

TABLE 16

Compound obtained by example N

| Example No. | Synthesized inhibitors (mass and analytical data) |
|---|---|
| OR1085 | 5-{[2-Methyl-5-(4-methyl-benzoylamino)-phenylamino]-methyl}-1H-pyrrolo[2,3-b]pyridine-2-carboxylic acid diethylamide |

TABLE 16-continued

Compound obtained by example N

Example No. Synthesized inhibitors (mass and analytical data)

Yield: 76%
$^1$H NMR (400 MHz, DMSO) δ 11.99 (s, 1H), 9.80 (s, 1H), 8.38 (s, 1H), 8.00 (s, 1H), 7.79 (d, J = 7.9, 2H), 7.28 (d, J = 7.9, 2H), 7.06 (s, 1H), 7.01 (d, J = 7.8, 1H), 6.92 (d, J = 7.8, 1H), 6.69 (s, 1H), 4.44 (s, 2H), 3.51 (m, 4H), 2.36 (s, 3H), 2.13 (s, 3H), 1.17 (t, J = 6.8, 6H). HPLC: 99%; MS: 470 (M + 1)

Example O

Synthesis of 5-[2-(benzoylamino)-phenyl-ethylamino]-1H-pyrrolo[2,3-b]pyridine-2-carboxylic acid methyl ester Scheme 44 - General synthesis scheme of example O

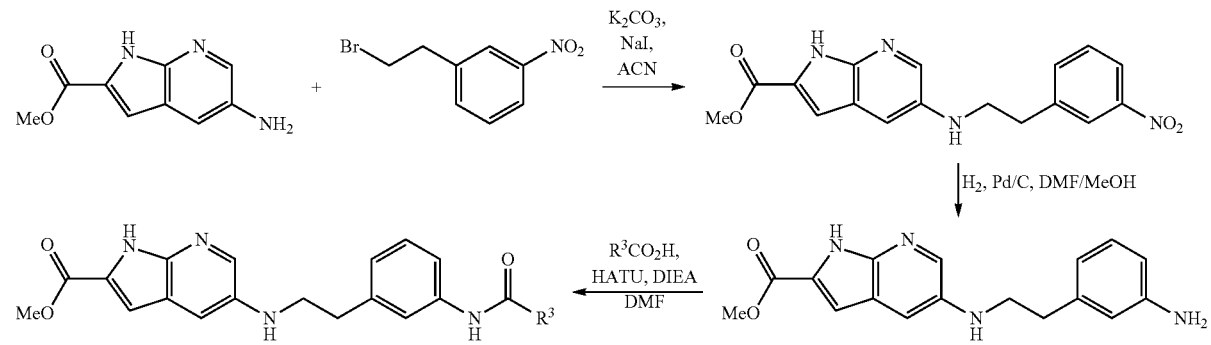

Step 1: Protocol for the Preparation of 5-[2-(3-Nitro-phenyl)-ethylamino]-1H-pyrrolo[2,3-b]pyridine-2-carboxylic acid methyl ester 5-Amino-1H-pyrrolo[2,3-b]pyridine-2-carboxylic acid methyl ester (1 eq) and 3-nitrophenethyl bromide (1 eq) were dissolved in acetonitrile. NaI (1 eq) and $K_2CO_3$ (2 eq) were added. After heating at 85° C. overnight, 1 eq of 3-nitrophenethyl bromide was added and the mixture was heated for 4 h. Then Acetonitrile was evaporated, NaHCO3 solution was added and the aqueous phase was extracted with AcOEt. The organic layer was evaporated and the crude was purified on reverse phase chromatography.

Yellow solid. Yield=31%. ESI-MS: m/z 341 ([M+H]$^+$). HPLC purity: 70%.

Step 2: Protocol for the Preparation of 5-[2-(3-Amino-phenyl)-ethylamino]-1H-pyrrolo[2,3-b]pyridine-2-carboxylic acid methyl ester 5-[2-(3-Nitro-phenyl)-ethylamino]-1H-pyrrolo[2,3-b]pyridine-2-carboxylic acid methyl ester (1 eq) was dissolved in a mixture DMF/MeOH (2/1). Pd/C 10% (20% w/w) was added and the mixture was stirred at room temperature overnight under 30 bar of dihydrogene.Then Pd/C was filtered off and the solvents were evaporated to give the expected product.

Yellow solid. Yield=99%. ESI-MS: m/z 311 ([M+H]$^+$) HPLC purity: 92%.

Step 3: Protocol for the preparation of 5-(2-{3-[4-(4-methyl-piperazin-1-ylmethyl)-3-trifluoromethyl-benzoylamino]-phenyl}-ethylamino)-1H-pyrrolo[2,3-b]pyridine-2-carboxylic acid methyl ester Carboxylic acid derivative (1 eq) is dissolved in anhydrous DMF (0.15 mol/L) with DIEA (4 eq) and HATU (2 eq). After 20 min, 5-[2-(3-Amino-phenyl)-ethylamino]-1H-pyrrolo[2,3-b]pyridine-2-carboxylic acid methyl ester is slowly added and mixture is stirred overnight at RT. DMF is evaporated and $NaHCO_{3(aq)}$ is added. The aqueous layer is extracted with AcOEt and the organic one is concentrated before purification on reverse phase chromatography column.

Table 17 shows the compounds synthesized according to the synthesis described above in scheme 44

TABLE 17

| Compound obtained by example O | |
|---|---|
| Example No. | Synthesized inhibitors (mass and analytical data) |
| OR1019 | 5-(2-{3-[4-(4-Methyl-piperazin-1-ylmethyl)-3-trifluoromethyl-benzoylamino]-phenyl}-ethylamino)-1H-pyrrolo[2,3-b]pyridine-2-carboxylic acid methyl ester |

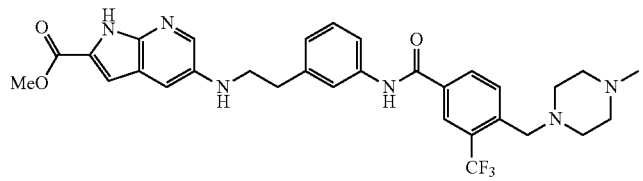 [SMILES: COC(=O)c1cc2cc(NCCc3cccc(NC(=O)c4ccc(CN5CCN(C)CC5)c(C(F)(F)F)c4)c3)cnc2[nH]1]

Yield: 13%
$^1$H NMR (300 MHz, DMSO) 12.04 (s, 1H), 10.41 (s, 1H), 8.25 (s, 1H), 8.23 (d, J = 8.3, 1H), 8.01 (d, J = 2.2, 1H), 7.92 (d, J = 7.9, 1H), 7.70-7.61 (m, 2H), 7.31 (t, J = 7.9, 1H), 7.11 (d, J = 2.5, 1H), 7.08 (d, J = 7.9, 1H), 6.93 (d, J = 2.2, 1H), 5.64 (t, J = 5.6, 1H), 3.84 (s, 3H), 3.70 (s, 2H), 3.31-3.23 (m, 2H), 2.89 (t, J = 7.3, 2H), 2.48-2.36 (m, 8H), 2.27 (s, 3H)
HPLC: 96%; MS: 595 (M + 1)

Example P

Synthesis of 5-(3-[3-trifluoro]-benzoylamino-phenylsulfanylmethyl)-1H-pyrrolo[2,3-b]pyridine-2-carboxylic acid methyl ester The synthesis of N-[3-(3-benzoylamino-phenyldisulfanyl)-phenyl]-benzamide intermediate is required for the synthesis of 5-(3-benzoyamino-phenylsulfanylmethyl)-1H-pyrrolo[2,3-b]pyridine-2-carboxylic acid methyl ester. Its synthesis is presented in Scheme 45.

Scheme 45 - General synthesis scheme of N-[3-(3-Benzoylamino-phenyldisulfanyl)-phenyl]-benzamide intermediate

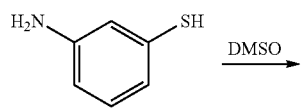

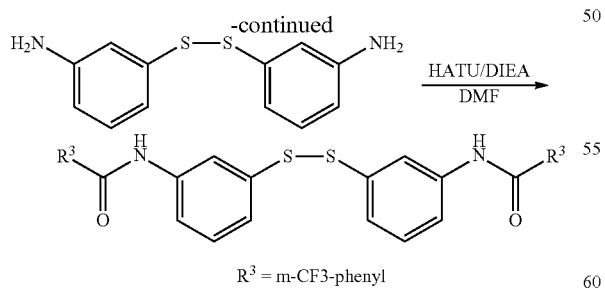

R³ = m-CF3-phenyl

Step 1: Protocol for the Preparation of 3,3'-diaminodiphenyl disulfide

3-Aminothiophenol was dissolved in DMSO and the mixture was heated at 90° C. for 4 h. The mixture was poured in 6N HCl solution. The yellow solid was filtered and dried under vacuum. Yellow solid (0.86 g).
Yield=57%. ESI-MS: m/z 249 ([M+H]+). HPLC purity: 98%.

Step 2: Protocol for the Preparation of N-[3-(3-(3-trifluoromethyl)-benzoylamino-phenyldisulfanyl)-phenyl]-benzamide 3-Trifluoromethyl-benzoic acid (1 eq) was dissolved in anhydrous DMF (0.1 mol/L) with DIEA (5 eq) and HATU (2.2 eq). After 20 min at room temperature, 3,3'-Diamino-diphenyl disulfide was slowly added and mixture was heated at 60° C. overnight. DMF was evaporated and HCl 1N was added. After extraction with AcOEt, the organic layer was ashed with NaHCO3 and concentrated. The crude was purified on silicagel chromatography.
White solid (0.40 g). Yield=47%. ESI-MS: m/z 593 ([M+H]+). HPLC purity: 97%.

The synthesis of 5-(3-benzoylamino-phenylsulfanylmethyl)-1H-pyrrolo[2,3-b]pyridine-2-carboxylic acid methyl ester final compound is described in Scheme 46.

Scheme 46 - General synthesis scheme of example P

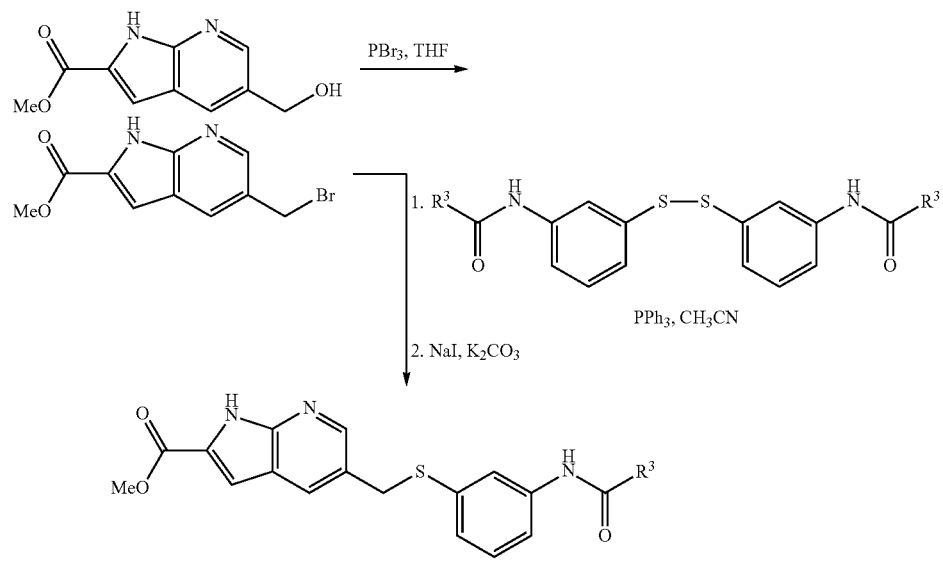

Step 1: Protocol for the Preparation of 5-bromomethyl-1H-pyrrolo[2,3-b]pyridine-2-carboxylic acid methyl ester 5-Hydroxymethyl-1H-pyrrolo[2,3-b]pyridine-2-carboxylic acid methyl ester (1 eq) was suspended in dry THF. Phosphotrus tribromide (1.5 eq) was added and the micture was stirred at room temperature overnight. The reaction was quenched by addition of water, THF was evaporated and the precipitate was filtered off, washed with water and dried under vacuum.
Off white solid (0.1 g). Yield=quantitative. ESI-MS: m/z 269/271 ([M+H]+). HPLC purity: 87%.

Step 2: Synthesis of [5-3-(3-trifluoromethyl-benzoylamino)-phenylsulfanylmethyl]-1H-pyrrolo[2,3-b]pyridine-2-carboxylic acid methyl ester N-[3-(3-(3-trifluoromethyl)-benzoylamino-phenyldisulfanyl)-phenyl]-benzamide (1 eq) was suspended in dry acetonitrile with triphenylphosphine (2 eq). The mixture was stirred overnight at RT. Then, 5-Bromomethyl-1H-pyrrolo[2,3-b]pyridine-2-carboxylic acid methyl ester (3 eq), NaI (3 eq) and K2CO3 (4.5 eq) were added. The mixture was refluxed for 6 h. After concentration, the crude was washed with NaHCO3 solution, extracted with AcOEt. The organic layer was concentrated and purified on reverse phase chromatography.

Table 18 shows the compounds synthesized according to the synthesis described above in Scheme 46.

TABLE 18

Compound obtained by example P

| Example No. | Synthesized inhibitors (mass and analytical data) |
|---|---|
| OR1066 | 5-[3-(3-Trifluoromethyl-benzoylamino)-phenylsulfanylmethyl]-1H-pyrrolo[2,3-b]pyridine-2-carboxylic acid methyl ester<br><br>Yield: 8%<br>¹H NMR (400 MHz, DMSO) δ 12.51 (s, 1H), 10.47 (s, 1H), 8.42 (d, J = 2.1, 1H), 8.27 (s, 1H), 8.24 (d, J = 8.0, 1H), 8.08 (d, J = 2.1, 1H), 7.98 (d, J = 7.8, 1H), 7.83 (s, 1H), 7.79 (t, J = 7.8, 1H), 7.60 (d, J = 8.0, 1H), 7.31 (t, J = 8.0, 1H), 7.14 (t, J = 7.8, 1H), 7.13 (s, 1H), 4.37 (s, 2H), 3.86 (s, 3H)<br>HPLC: 95%; MS: 486 (M + 1) |

Example Q

Synthesis of 5-[2-(3-{[4-(4-methyl-piperazin-1-ylmethyl)-3-trifluoromethyl-benzoylamino]-methyl}-phenyl)-ethyl]-1H-pyrrolo[2,3-b]pyridine-2-carboxylic acid methyl ester

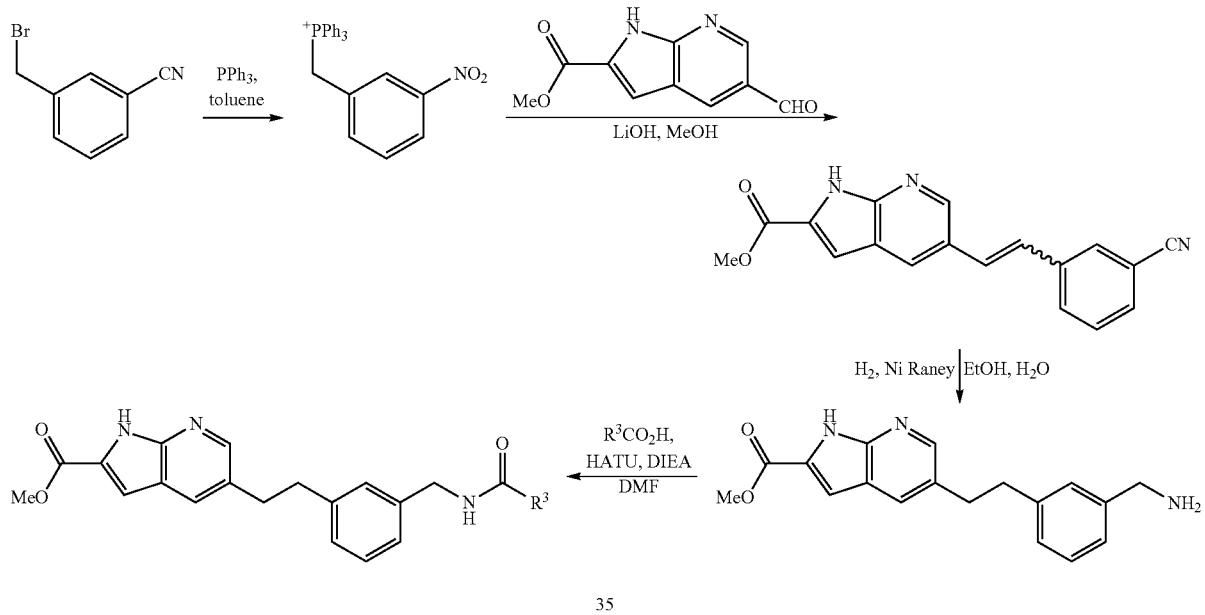

Scheme 47 - General synthesis scheme of example Q

Step 1: Protocol for the Preparation of (3-cyano-benzyl)-triphenyl-phosphonium 3-Bromomethyl-benzonitrile (1 g) was added in a dried flask with triphenylphosphine (1 eq) in anhydrous toluene (30 mL) and the reaction was stirred overnight at reflux. The crude was filtered and washed with toluene and Et₂O to obtain a white powder (2.23 g).
Yield=95%. ESI-MS: m/z 458 ([M]+). HPLC purity>90%.

Step 2: Protocol for the Preparation of 5-[2-(3-cyano-phenyl)-vinyl]-1H-pyrrolo[2,3-b]pyridine-2-carboxylic acid methyl ester 5-Formyl-1H-pyrrolo[2,3-b]pyridine-2-carboxylic acid methyl ester (200 mg) was added in a dried flask with (3-cyano-benzyl)-triphenyl-phosphonium (1.2 eq), LiOH (2 eq) in anhydrous MeOH (30 mL) and the reaction was stirred at reflux overnight. The crude mixture was basified with NH₄Cl to pH 7 and the precipitate was filtered and washed with Et₂O to obtain a off white powder.
Yield=22%. ESI-MS: m/z 304 ([M+H]+). HPLC purity: 95%.

Step 3: Protocol for the Preparation of 5-[2-(3-aminomethyl-phenyl)-ethyl]-1H-pyrrolo[2,3-b]pyridine-2-carboxylic acid methyl ester 5-[2-(3-Cyano-phenyl)-vinyl]-1H-pyrrolo[2,3-b]pyridine-2-carboxylic acid methyl ester (68 mg) was dissolved in EtOH/H₂O (1/1) mixture with HCl 37% (1.5 ml). Raney Nickel was added and the mixture was stirred overnight under $H_2$ pressure (30 bar). The mixture was then filtered over celite. The filtrate was concentrated, washed with saturated $NaHCO_3$ and extracted with AcOEt, dried over $Na_2SO_4$ and concentrated. White solid (40 mg).

Yield=58%. ESI-MS: m/z 310 ([M+H]+).

Step 4: Protocol for the Preparation of 5-[2-(3-{[4-(4-methyl-piperazin-1-ylmethyl)-3-trifluoromethyl-benzoylamino]-methyl}-phenyl)-ethyl]-1H-pyrrolo[2,3-b]pyridine-2-carboxylic acid methyl ester Carboxylic acid derivative (1 eq) is dissolved in anhydrous DMF (0.15 mol/L) with DIEA (4 eq) and HATU (2 eq). After 20 min, 5-[2-(3-aminomethyl-phenyl)-ethyl]-1H-pyrrolo[2,3-b]pyridine-2-carboxylic acid methyl ester is slowly added and mixture is stirred overnight at RT. DMF is evaporated and $NaHCO_{3(aq)}$ is added. The aqueous layer is extracted with AcOEt and the organic one is concentrated before purification on reverse phase chromatography column.

Table 19 shows the compounds synthesized according to the synthesis described above in Scheme 47.

TABLE 19

Compound obtained by example Q

| Example No. | Synthesized inhibitors (mass and analytical data) |
|---|---|
| OR1018 | 5-[2-(3-{[4-(4-Methyl-piperazin-1-ylmethyl)-3-trifluoromethyl-benzoylamino]-methyl}-phenyl)-ethyl]-1H-pyrrolo[2,3-b]pyridine-2-carboxylic acid methyl ester<br><br>Yield: 34%<br>¹H NMR (300 MHz, DMSO) δ 12.37 (s, 1H), 9.24 (t, J = 5.8, 1H), 8.29 (d, J = 2.0, 1H), 8.21 (s, 1H), 8.16 (d, J = 8.1, 1H), 7.94 (s, 1H), 7.86 (d, J = 8.1, 1H), 7.26-7.20 (m, 2H), 7.16-7.09 (m, 2H), 7.07 (d, J = 2.0, 1H), 4.47 (d, J = 5.8, 2H), 3.86 (s, 3H), 3.66 (s, 2H), 3.03-2.86 (m, 4H), 2.41 (bs, 8H), 2.21 (s, 3H)<br>HPLC: 98%; MS: 594 (M + 1) |

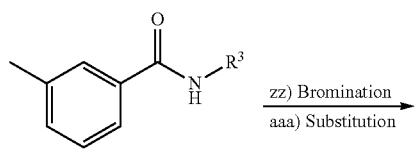

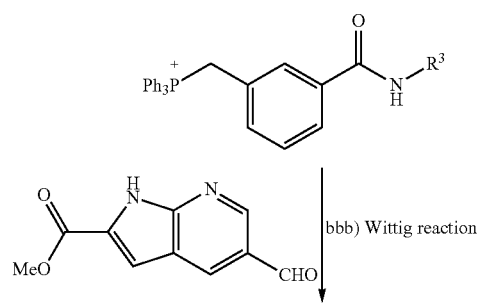

Example R

The synthesis of 5-{2-[3-(3-trifluoromethyl-phenylcarbamoyl)-phenyl]-vinyl}-1H-pyrrolo[2,3-b]pyridine-2-carboxylic acid methyl ester is described in Scheme 48

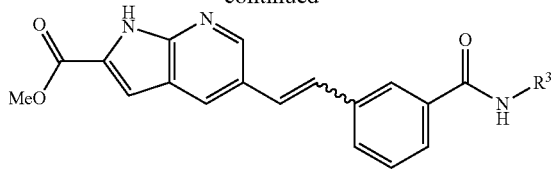

Step 1: Protocol for the Preparation of 3-methyl-N-(3-trifluoromethyl-phenyl)-benzamide 3-Trifluoromethylaniline (1.2 eq), m-toluic acid (1 eq), HOBT (1.2 eq), EDCI.HCl (1.2 eq) and DIEA (3 eq) were dissolved in dry DMF and the mixture was heated at 60° C. overnight. After concentration, the crude was washed with HCl 1N solution, extracted with AcOEt. The organic layer Scheme 48 - General synthesis scheme of example R

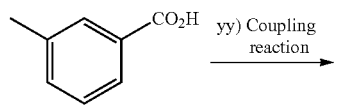

yy) Coupling reaction was washed with NaHCO3 solution then concentrated. The crude was purified on silicagel chromatography to give a white solid.

Yield=41%. ESI-MS: m/z 280 ([M+H]+). HPLC purity: 100%.

Step 2: Protocol for the Preparation of 3-bromomethyl-N-(3-trifluoromethyl-phenyl)-benzamide 3-methyl-N-(3-trifluoromethyl-phenyl)-benzamide (1 eq) and AIBN (0.04 eq) were dissolved in acetonitrile (0.07M) and the mixture was refluxinf for 15 min. Then, each 30 min and for 1 h30, the reaction was cooled down to 70° C. and 0.25 eq of NBS followed by 0.015 eq of AIBN. After the sixth addition, the mixture was refluxing for 5 h. Then 0.1 eq of AIBN and 0.5 eq of NBS were added and the misture was refluxing overnight. Finally, 0.1 eq of AIBN and 0.25 eq of NBS were added and the mixture was heated for 4 h. Finally, after evaporation of solvent the crude was washed with saturated $NaHCO_3$ solution and extracted with dichloromethane. The organic layer was dried over $Na_2SO_4$ and concentrated to give the crude oil.

ESI-MS: m/z 358/360 ([M+H]+). HPLC purity: 60%.

Step 3: Protocol for the Preparation of triphenyl-[3-(3-trifluoromethyl-phenylcarbamoyl)-benzyl]-phosphonium 2-Bromomethyl-4-nitro-benzene derivative (1 eq) was added in a dried flask with triphenylphosphine (1.2 eq) in anhydrous toluene (0.1M) and the reaction was stirred overnight at reflux. The crude was filtered and washed with toluene and $Et_2O$ to obtain a brown powder.

Yield=71%. ESI-MS: m/z 620 ([M]+). HPLC purity: 70%.

Step 4: Protocol for the Preparation of 5-{2-[3-(3-Trifluoromethyl-phenylcarbamoyl)-phenyl]-vinyl}-1H-pyrrolo[2,3-b]pyridine-2-carboxylic acid methyl ester 5-Formyl-1H-pyrrolo[2,3-b]pyridine-2-carboxylic acid methyl ester (1 eq) was added in a dried flask with triphenyl-[3-(3-trifluoromethyl-phenylcarbamoyl)-benzyl]-phosphonium (1.3 eq), LiOH (3 eq) in anhydrous MeOH. The reaction was stirred at RT overnight. The reaction was quenched with $NH_4Cl$ solution. Methanol was evaporated and the aqueous layer was extracted with AcOEt. The organic layer was evaporated and purified on reverse phase chromatography.

Table 20 shows the compounds synthesized according to the synthesis described above in Scheme 48.

TABLE 20

| Compound obtained by example R | |
|---|---|
| Example No. | Synthesized inhibitors (mass and analytical data) |
| OR1046 | 5-{2-[3-(3-Trifluoromethyl-phenylcarbamoyl)-phenyl]-vinyl}-1H-pyrrolo[2,3-b]pyridine-2-carboxylic acid methyl ester |

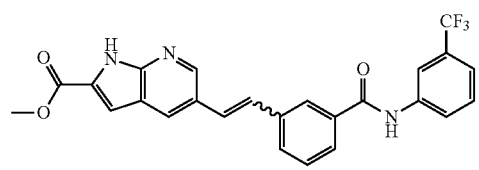 [SMILES: COC(=O)c1cc2cc(C=Cc3cccc(C(=O)Nc4cccc(C(F)(F)F)c4)c3)cnc2[nH]1]

TABLE 20-continued

| Compound obtained by example R | |
|---|---|
| Example No. | Synthesized inhibitors (mass and analytical data) |
| | Yield: 3%<br>$^1$H NMR $^1$H NMR (400 MHz, DMSO) δ 12.54 (s, 1H), 10.53 (s, 1H), 8.24 (d, J = 1.8, 1H), 8.19 (s, 1H), 8.00 (d, J = 88.0, 1H), 7.97 (d, J = 1.7, 1H), 7.88 (s, 1H), 7.86-7.81 (m, 1H), 7.58 (t, J = 8.0, 1H), 7.47-7.40 (m, 3H), 7.10 (d, J = 1.7, 1H), 6.85 (d, J = 12.2, 1H), 6.80 (d, J = 12.2, 1H), 3.86 (s, 3H)<br>HPLC: 93%; MS: 466 (M + 1) |

Biological Results

Material and Methods:
1) In Vitro Kinase Assays

The inhibitory activity of the compounds on 7 kinases (BRAF, EGFR (ErbB1), EGFR (ErbB1) T790M L858R, FGFR2, KDR (VEGFR2), PDGFRA (PDGFR alpha), SRC) was evaluated by Invitrogen using the Z'-LYTE® technology. Briefly, the Z'-LYTE® biochemical assay employs a fluorescence-based, coupled-enzyme format and is based on the differential sensitivity of phosphorylated and non-phosphorylated peptides to proteolytic cleavage. The peptide substrate is labeled with two fluorophores—one at each end—that make up a FRET pair. A ratiometric method, which calculates the ratio (the Emission Ratio) of donor emission to acceptor emission after excitation of the donor fluorophore at 400 nm, is used to quantitate reaction progress.

The compounds are screened in 1% DMSO (final) in the well. For 10 point titrations, 3-fold serial dilutions are conducted from the starting concentration. All Peptide/Kinase Mixtures are diluted to a 2× working concentration in the appropriate Kinase Buffer. All ATP Solutions are diluted to a 4× working concentration in Kinase Buffer (50 mM HEPES pH 7.5, 0.01% BRIJ-35, 10 mM MgCl2, 1 mM EGTA). ATP Km apparent is previously determined using a Z'-LYTE® assay.

Each compound was incubated at a concentration of 100 nM and the tables 21 to 27 summarize the results obtained showing the inhibitory power of a compound.

2) In Vitro Cell Proliferation Assays

Cancer cell lines (5×10³ cells per well) or HUVEC (1×10⁴ cells per well) or HRMEC (1×10⁴ cells per well) were distributed in 96-well plates and incubating in duplicate with escalating concentrations (10 nM to 3 µM) of compounds for 72 hr. Cell proliferation was measured using MTT (3[4,5-dimethylthiazol-2-yl]-2,5-diphenyltetrazolium bromide). The EC50 values were calculated from sigmoidal dose-response curves utilizing Prism 5.0 from Graph-Pad Software (GraphPad Software, La Jolla, Calif., USA), with values normalized to those of DMSO-treated control wells (0%) and 1% SDS control wells (100%).

Biological Results:

The in vitro kinase assays reveal several kinase-inhibiting molecular structures. More than 15 compounds are able to inhibit at least 4 of the kinases tested (IC50 expected to be less than 100 nM on each of these kinases as the inhibition percent is better than 50% at the concentration of 100nM). It should be noted that these compounds display inhibitory activity on kinases that represent different and distant kinase families (serine/threonine or tyrosine kinases) involved in multiple pathways in tumor progression as developed in the introduction part (angiogesesis, migration, metastatis, tumor growth . . . ). These compounds are multi-targeted kinase inhibitors with large spectrum.

The anti-proliferative potency of compounds was evaluated either on malignant cancer cell lines or on primary endothelial cells mimicking the angiogenesis process. The EC50 corresponding to the concentration of compound inhibiting cell growth at a level of 50% were determined. The results obtained are presented in tables 21 to 41.

We consider in those experiments that compounds presenting an EC50 superior than 3 µM are inactive on the tested cell type. Compounds with an EC50 between 1 µM and 3 µM are considered active, as Sorafenib, which is currently marketed to treat hepatocellular carcinoma, presents here an EC50 between 1 µM and 3 µM on 4 liver cancer cell lines (HepG2, HuH7, HuCCT1 and HuH6 Clone 5). Several compounds are highly potent inhibitors of the cellular growth in several cell types tested and present antiangiogenic properties on HUVEC. For all the cancer cell lines, several compounds highly inhibit the cell growth. Taken together, these results indicate that the compounds of the invention are able to block at least two pathways of the tumor growth (epithelial cell proliferation and angiogenesis).

TABLE 21

In vitro kinase assays. Each compound was incubated at 100 nM using an ATP Km apparent concentration. The activity is represented by the % of inhibition of the kinase compared to the control.
BRAF

| <50% | ≥50% |
| --- | --- |
| OR0723, OR0724, OR0726, OR0728, OR0730, OR0738, OR0746, OR0747, OR0749, OR0750, OR0779, OR0776, OR0777, OR0778, OR0834, OR0918, OR0919, OR0921, OR0922, OR0967, OR0969, OR0976, OR0977, OR0978, OR1006, OR1007, OR1014, OR1017, OR1018, OR1019, OR1020, OR1044, OR1054, OR1057, OR1064, OR1066, OR1068, OR1070 | OR0748, OR0775, OR0797, OR0798, OR0799, OR0800, OR0812, OR0920, OR0966, OR0981, OR1008, OR1059, OR1061 |

TABLE 22

In vitro kinase assays. Each compound was incubated at 100 nM using an ATP Km apparent concentration. The activity is represented by the % of inhibition of the kinase compared to the control.
EGFR (ErbB1)

| <50% | ≥50% |
| --- | --- |
| OR0726, OR0728, OR0730, OR0738, OR0800, OR0776, OR0918, OR0919, OR0966, OR0967, OR0976, OR0977, OR0978, OR0981, OR1008, OR1014, OR1017, OR1018, OR1020, OR1064, OR1066 | OR0723, OR0724, OR0746, OR0747, OR0749, OR0750, OR0779, OR0748, OR0775, OR0797, OR0798, OR0799, OR0777, OR0778, OR0812, OR0834, OR0920, OR0921, OR0922, OR0969, OR1006, OR1007, OR1019, OR1044, OR1054, OR1057, OR1059, OR1061, OR1068, OR1070 |

TABLE 23

In vitro kinase assays. Each compound was incubated at 100 nM using an ATP Km apparent concentration. The activity is represented by the % of inhibition of the kinase compared to the control.
EGFR (ErbB1) T790M L858R

| <50% | ≥50% |
| --- | --- |
| OR0723, OR0726, OR0728, OR0730, OR0738, OR0746, OR0747, OR0749, OR0750, OR0779, OR0777 | OR0724, OR0748, OR0775 |

TABLE 24

In vitro kinase assays. Each compound was incubated at 100 nM using an ATP Km apparent concentration. The activity is represented by the % of inhibition of the kinase compared to the control.
FGFR2

| <50% | ≥50% |
| --- | --- |
| OR0723, OR0724, OR0726, OR0728, OR0730, OR0738, OR0746, OR0779, OR0799, OR0800, OR0776, OR0778, OR0834, OR0918, OR0919, OR0966, OR0967, OR0976, OR0977, OR0978, OR0981, OR1008, OR1014, OR1017, OR1018, OR1019, OR1020, OR1057, OR1061, OR1064, OR1066 | OR0747, OR0749, OR0750, OR0748, OR0775, OR0797, OR0798, OR0777, OR0812, OR0920, OR0921, OR0922, OR0969, OR1006, OR1007, OR1044, OR1054, OR1059, OR1068, OR1070 |

TABLE 25

In vitro kinase assays. Each compound was incubated at 100 nM using an ATP Km apparent concentration. The activity is represented by the % of inhibition of the kinase compared to the control.
KDR (VEGFR2)

| <50% | ≥50% |
| --- | --- |
| OR0723, OR0724, OR0726, OR0728, OR0730, OR0738, OR0746, OR0918, OR0919, OR0966, OR0967, OR0976, OR0977, OR1014, OR1017, OR1057, OR1064 | OR0747, OR0749, OR0750, OR0779, OR0748, OR0775, OR0797, OR0798, OR0799, OR0800, OR0776, OR0777, OR0778, OR0812, OR0834, OR0920, OR0921, OR0922, OR0969, OR0978, OR0981, OR1006, OR1007, OR1008, OR1018, OR1019, OR1020, OR1044, OR1054, OR1059, OR1061, OR1066, OR1068, OR1070 |

TABLE 26

In vitro kinase assays. Each compound was incubated at 100 nM using an ATP Km apparent concentration. The activity is represented by the % of inhibition of the kinase compared to the control.
PDGFRA (PDGFR alpha)

| <50% | ≥50% |
| --- | --- |
| OR0723, OR0724, OR0726, OR0730, OR0738, OR0966, OR0967, OR0976, OR0977, OR1014 | OR0728, OR0746, OR0747, OR0749, OR0750, OR0779, OR0748, OR0775, OR0797, OR0798, OR0799, OR0800, OR0776, OR0777, OR0778, OR0812, OR0834, OR0918, OR0919, OR0978, OR0981, OR1057, OR1059, OR1061, OR1064, OR1066, OR1068, OR1070 |

TABLE 27

In vitro kinase assays. Each compound was incubated at 100 nM using an ATP Km apparent concentration. The activity is represented by the % of inhibition of the kinase compared to the control.

SRC

| <50% | ≥50% |
|---|---|
| OR0723, OR0724, OR0726, OR0728, OR0730, OR0738, OR0746, OR0776, OR0918, OR0919, OR0966, OR0967, OR0976, OR0977, OR0978, OR1014, OR1061, OR1064, OR1066 | OR0747, OR0749, OR0750, OR0779, OR0748, OR0775, OR0797, OR0798, OR0799, OR0800, OR0777, OR0778, OR0812, OR0834, OR0981, OR1057, OR1059, OR1068, OR1070 |

TABLE 28

Anti-proliferative activity of the compounds of the invention on A549 cell line.

A549

| $EC_{50} \leq 100$ nM | 100 nM < EC50 < 1 µM | $EC_{50} \geq 1$ µM |
|---|---|---|
| OR0748, OR0797, OR0798, OR0812 | OR0748, OR0921, OR1006, OR1059 | OR0738, OR0746, OR0747, OR0749, OR0750, OR0779, OR0777, Erlotinib, OR0919, OR0966, OR1044, OR1007, OR1008, OR1014, OR1017, OR1018, OR1019, OR1020, OR1044, OR1046, OR1057, OR1061, OR1066, OR1068, OR1070 |

TABLE 29

Anti-proliferative activity of the compounds of the invention on HepG2 cell line.

HepG2

| $EC_{50} \leq 100$ nM | 100 nM < EC50 < 1 µM | $EC_{50} \geq 1$ µM |
|---|---|---|
| OR0919 | OR0748, OR0797, OR0798, OR0777, OR0812, OR0920, OR0921, OR0966, OR1017, OR1059 | OR0738, OR0746, OR0747, OR0749, OR0750, OR0779, OR0775, OR0799, OR0800, Dasatinib, OR0834, OR0918, OR0922, OR0967, OR0969, OR0976, OR0977, OR0978, OR0981, OR1006, OR0778, OR1007, OR1008, OR1014, OR1018, OR1019, OR1020, OR1044, OR1046, OR1057, OR1061, OR1066, OR1068, OR1070 |

TABLE 30

Anti-proliferative activity of the compounds of the invention on HuCCT1 cell line.

HuCCT1

| $EC_{50} \leq 100$ nM | 100 nM < EC50 < 1 µM | $EC_{50} \geq 1$ µM |
|---|---|---|
|  | OR0748, OR0799, OR0777 | OR0738, OR0746, OR0747, OR0749, OR0750, OR0779, OR0775, OR0797, OR0798, OR0800, Dasatinib, OR0778 |

TABLE 31

Anti-proliferative activity of the compounds of the invention on HuH6 Clone 5 cell line.

HuH6 Clone 5

| $EC_{50} \leq 100$ nM | 100 nM < EC50 < 1 µM | $EC_{50} \geq 1$ µM |
|---|---|---|
|  | OR0797, OR0798, OR0777 | OR0748, OR0749, OR0775, OR0799, OR0800, OR0778 |

TABLE 32

Anti-proliferative activity of the compounds of the invention on HuH7 cell line.

HuH7

| $EC_{50} \leq 100$ nM | 100 nM < EC50 < 1 µM | $EC_{50} \geq 1$ µM |
|---|---|---|
| OR0797 | OR0748, OR0749, OR0775, OR0798, OR0799, OR0777, OR0812 | OR0800, OR0778, OR0834 |

TABLE 33

Anti-proliferative activity of the compounds of the invention on HT29 cell line.

HT29

| $EC_{50} \leq 100$ nM | 100 nM < EC50 < 1 µM | $EC_{50} \geq 1$ µM |
|---|---|---|
|  | OR0749 | Erlotinib, OR0738, OR0746, OR0747, OR0748, OR0750, OR0779, OR0777, OR0812 |

TABLE 34

Anti-proliferative activity of the compounds of the invention on H1975 cell line.

H1975

| $EC_{50} \leq 100$ nM | 100 nM < EC50 < 1 µM | $EC_{50} \geq 1$ µM |
|---|---|---|
|  | OR0750, OR0748 | OR0738, OR0746, OR0747, OR0749, OR0779, OR0777, OR0812 |

TABLE 35

Anti-proliferative activity of the compounds of the invention on HUVEC cells.
HUVEC

| $EC_{50} \leq 100$ nM | 100 nM < EC50 < 1 µM | $EC_{50} \geq 1$ µM |
|---|---|---|
| OR0748, OR0797, OR0798, OR0921, OR1006 | Sorafenib, OR0747, OR0749, OR0750, OR0775, OR0799, OR0800, OR0777, OR0812, OR0922, OR1007, OR1014, OR1044, OR1068 | Sunitinib, Erlotinib, Dasatinib, OR0738, OR0746, OR0779, OR0778, OR0834, OR0918, OR0919, OR0920, OR0966, OR0967, OR0969, OR0976, OR0977, OR0978, OR0981, OR1008, OR1017, OR1018, OR1019, OR1020, OR1046, OR1057, OR1059, OR1061, OR1066, OR1070 |

TABLE 36

Anti-proliferative activity of the compounds of the invention on PC3 cell line.
PC3

| $EC_{50} \leq 100$ nM | 100 nM < EC50 < 1 µM | $EC_{50} \geq 1$ µM |
|---|---|---|
| | OR0812 | |

TABLE 367

Anti-proliferative activity of the compounds of the invention on Caki2 cell line.
Caki-2

| $EC_{50} \leq 100$ nM | 100 nM < EC50 < 1 µM | $EC_{50} \geq 1$ µM |
|---|---|---|
| | OR0812 | |

TABLE 38

Anti-proliferative activity of the compounds of the invention on MDA-MB-231 cell line.
MDA-MB-231

| $EC_{50} \leq 100$ nM | 100 nM < EC50 < 1 µM | $EC_{50} \geq 1$ µM |
|---|---|---|
| OR0748, OR0797, OR0921 | OR0798, OR0812, OR0919, OR1006, OR1019, OR1059 | OR0966, OR1044, OR0778, OR1007, OR1008, OR1014, OR1017, OR1018, OR1020, OR1046, OR1057, OR1061, OR1066, OR1068, OR1070 |

TABLE 379

Anti-proliferative activity of the compounds of the invention on BxPC3 cell line.
BxPC3

| $EC_{50} \leq 100$ nM | 100 nM < EC50 < 1 µM | $EC_{50} \geq 1$ µM |
|---|---|---|
| | OR0812 | |

TABLE 40

Anti-proliferative activity of the compounds of the invention on HeLa cell line.
HeLa

| $EC_{50} \leq 100$ nM | 100 nM < EC50 < 1 µM | $EC_{50} \geq 1$ µM |
|---|---|---|
| OR0921 | OR0748, OR0797, OR0798, OR0812, OR1006, OR1044, OR1059 | OR0919, OR0966, OR1007, OR1008, OR1014, OR1017, OR1018, OR1019, OR1020, OR1046, OR1057, OR1061, OR1066, OR1068, OR1070 |

TABLE 41

Anti-proliferative activity of the compounds of the invention on HRMEC cells.
HRMEC

| $EC_{50} \leq 100$ nM | 100 nM < EC50 < 1 µM | $EC_{50} \geq 1$ µM |
|---|---|---|
| OR0797 | OR0798, OR0812 | OR0746, OR0776, OR0779 |

The invention claimed is:
1. Compound of the following formula (I):

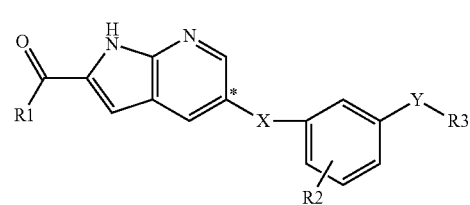

wherein
R1 is a $C_1$-$C_6$ alkyl group, a —NR4R5 group, or an —OR6 group,
R4, R5 and R6 are independently a hydrogen atom or $C_1$-$C_6$ alkyl group,
X is selected from the group consisting of:
—C*(R7R8)-N(R9)-C(R10R11)-,
—C*(R7R8)-N(R9)-C(O)—,
—C*(R7R8)N(R9)-,
—C*(R7R8)O—,
—O*C(R7R8)-,
—C*(R7R8)S—,
—S*C(R7R8)-,
—C*(R7R8)C(R9R10)-,
—C*(O)NH—,
—C*(S)NH—,
—C*(R7)=C(R8)-,
—C*(R7)=N—, and
—N*(R7)-C(R8R9)-C(R10R11)-
wherein R7, R8, R9, R10 and R11 are independently a hydrogen atom or $C_1$-$C_6$ alkyl, and the atoms labeled with a "*" are bonded to the carbon labeled with a "*" in formula (I),
R2 is a hydrogen atom, a $C_1$-$C_6$ alkyl group or a halogen atom,
Y is selected from the group consisting of HNC(O), HNC(S), HNSO$_2$, HNC(O)CH$_2$, HNC(S)CH$_2$, HNC(O)NH, HNC(S)NH, CH$_2$NHC(O), C(O)NH, CH$_2$NHC(S) and C(O)NHCH$_2$, and R3 is selected from the group consisting of:
  an aryl, group mono or polysubstituted with one or
    more selected from the group consisting of:
    a hydroxyl,
    a halogen,
    a $C_1$-$C_6$ alkyl-amine,
    a $C_1$-$C_6$ alkoxy,
    an amine substituted by a heteroaryl said heteroaryl
      optionally monosubstituted by a methyl,
    a $C_1$-$C_6$ trifluoroalkoxy,
    a $C_1$-$C_6$ alkyl,
    a $C_1$-$C_6$ trifluoroalkyl,
    a heteroaryl group optionally monosubstitued by a
      methyl,
    an aliphatic heterocycle, optionally substituted by a
      methyl group, a hydroxyl group, an amine group,
      —$NHCH_3$, or —$N(CH_3)_2$,
    a $C_1$-$C_6$ alkyl substituted by a heterocycle, wherein
      said heterocycle is optionally substituted by a
      methyl group, a hydroxyl group, an amine group,
      —$NHCH_3$, or —$N(CH_3)_2$, and
    the fragment:

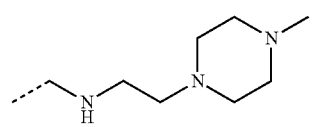

a heteroaryl group, and
  a non aromatic monosubstituted cyclic group,
and/or the pharmaceutically acceptable addition salts, solvates, Z or E isomers, enantiomers, diastereoisomers thereof, as well as mixtures thereof.

2. The compound of claim 1 wherein,
X is selected from the group consisting of:
  —$CH_2$—$CH_2$—,
  —CH═CH—,
  —$CH_2$—O—,
  —$CH_2$—NH—, and
  —CO—NH—, and
R2 is an alkyl group or a halogen atom.

3. The compound of claim 1, wherein,
R1 is a hydroxyl group, a methyl group, a methoxy group
  or —NHMe group,
R2 is a methyl or a chloride atom,
Y is HNC(O), HNC(O)$CH_2$, HNC(O)NH, HNC(S)NH,
  C(O)NH, C(O)$NHCH_2$, or $CH_2$NHC(O), and
R3 is selected from the group consisting of:
  a phenyl group mono substituted with a $C_1$-$C_6$ trifluoroalkyl group, a $C_1$-$C_6$ trifluoroalkoxy group, a $C_1$-$C_6$ alkyl group, a halogen, a non aromatic monosubstituted cyclic group, or a thiazol group optionally monosubstitued by a $CF_3$ and/or a methyl group,
  a phenyl group polysubstituted with a $C_1$-$C_6$ trifluoroalkyl, a $C_1$-$C_6$ alkyl-amine, a halogen, a non-aromatic monosubstituted cyclic group, a hydroxyl group and/or a thiazol group optionally monosubstitued by a $CF_3$ and/or a methyl group,
  a pyridine group, optionally substituted with a $C_1$-$C_6$ alkyl or a $C_1$-$C_6$ trifluoroalkyl,
  a non-aromatic cyclic group chosen between a cyclic $C_3$-$C_{10}$ alkyl, monosubstituted with a $C_1$-$C_6$ alkyl and/or a $C_1$-$C_6$ trifluoroalkyl, and a fragment selected from the group consisting of:

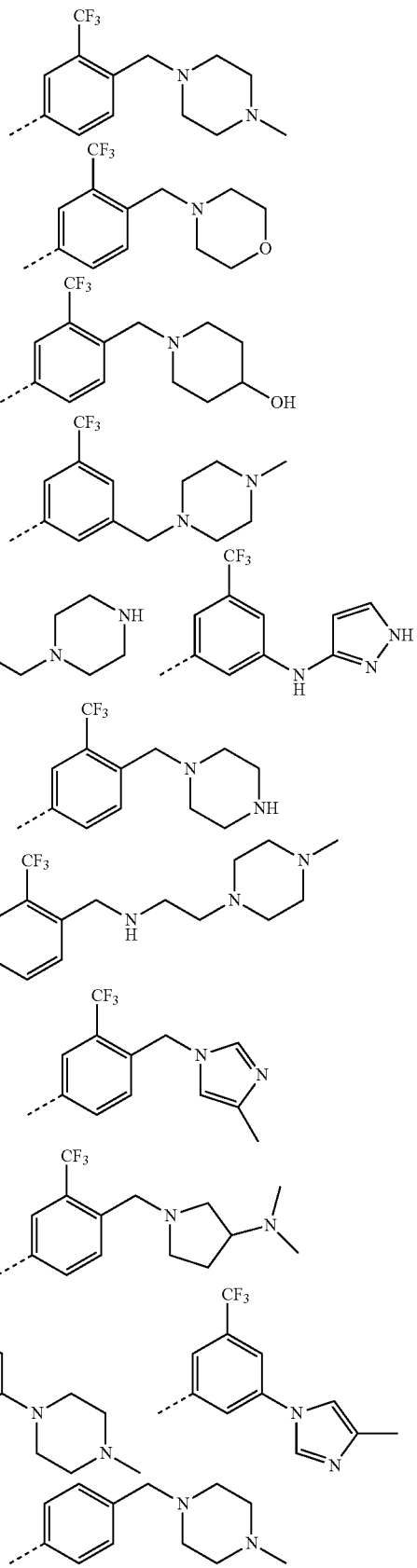

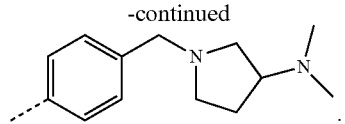

4. The compound of claim 1, wherein,
R1 is a methyl group or methoxy group,
R2 is a methyl group,
X is —CH₂—CH₂—,
 —CH═CH—,
 —CH₂—O—, or
 —CH₂—NH—,
Y is HNC*(O), wherein C* is linked to R3 and
R3 is chosen from a group consisting of:

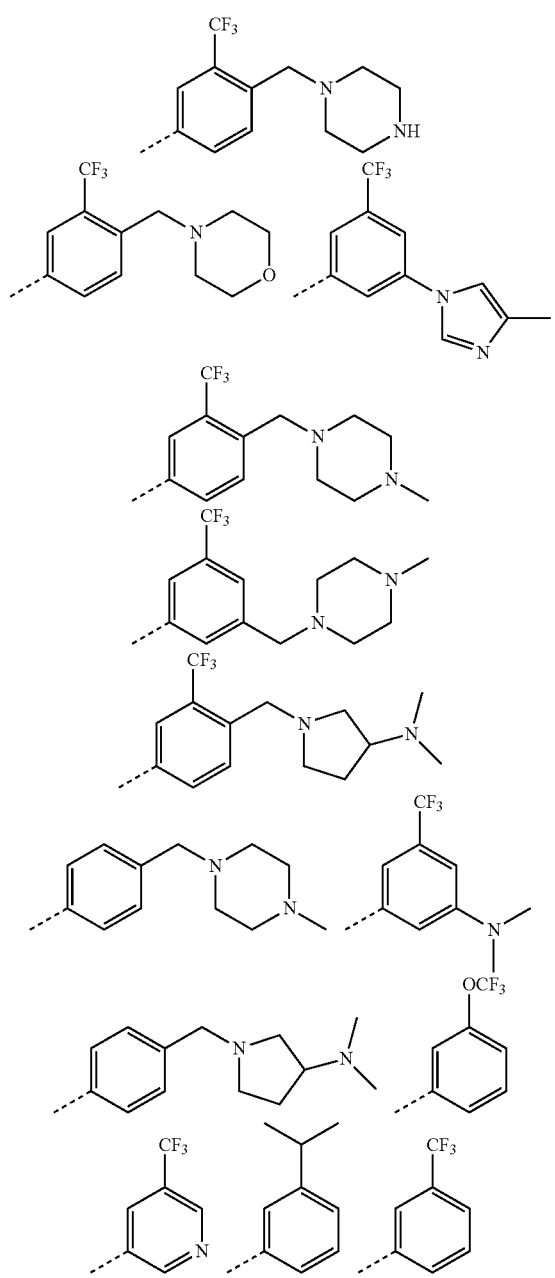

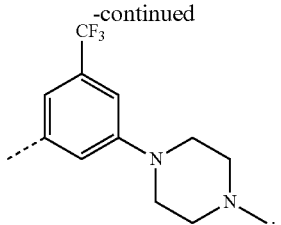

5. The compound of claim 1, wherein the compound is of formula (II):

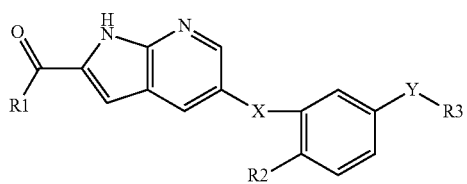

wherein R1, X, R2, Y and R3 are as defined in claim 1, and
wherein R3 is selected from:

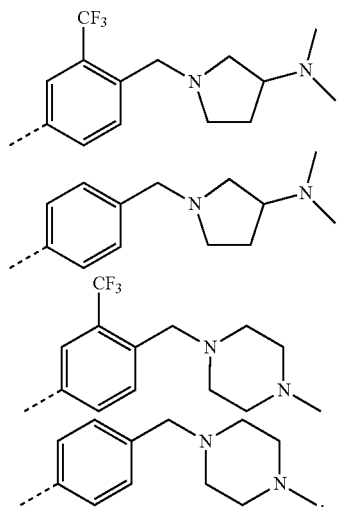

6. The compound of claim 1, wherein R1 is methyl or methoxy, X is CH₂—CH₂, —CH═CH—, or —CH₂—O— and R3 is selected from:

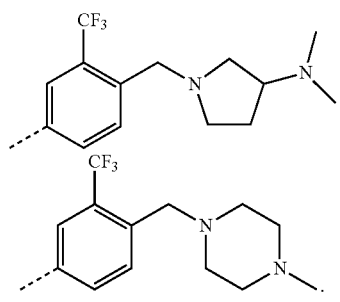

7. The compound of claim 1 wherein,
X is —CH$_2$—CH$_2$,
Y is HNC(O)NH or HNC(S)NH, and
R3 is selected from:

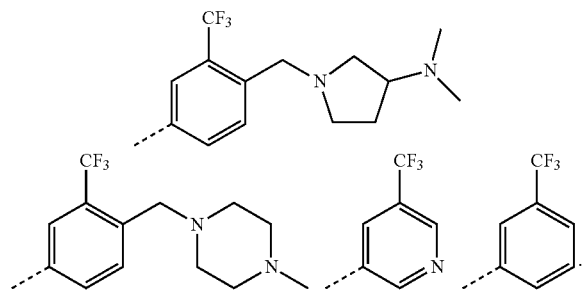

8. A method for preparation of the compound of claim 1, comprising forming group X by at least one of the following steps:
   a) performing a reductive amination,
   b) performing a Wittig reaction, with an optional reduction of the double bond,
   c) performing a coupling reaction done in peptide coupling conditions,
   d) performing a Mitsunobu reaction,
   e) performing a reduction,
   f) performing a hydrolysis,
   g) performing a brome substitution, or
   h) performing a condensation step.

9. The method of claim 8, wherein group X is formed by at least one of the following steps:
   a) performing a reductive amination,
   b) performing a Wittig reaction, with an optional reduction of the double bond,
   c) performing a coupling reaction done in peptide coupling conditions,
   d) performing a Mitsunobu reaction, and/or
   e) performing a reduction.

10. The method of claim 9, further comprising at least one of the following steps after steps (a), (b), (c), (d) and/or (e):
   f$_1$) forming a urea in the case of Y being HNC(O)NH, by reaction with an isocyanate,
   f$_2$) forming a thiourea in the case of Y being HNC(S)NH, by reaction with an isothiocyanate,
   f$_3$) forming a sulfonamide in the case of Y being HNSO$_2$, by reaction with a halogen sulfonyl,
   f$_4$) forming an amide in the case of Y being HNCO, by reaction with an activated carboxylic acid,
   f$_5$) forming a thioamide in the case of Y being HNCS, by reacting the compound obtained after step f4) with the Lawesson's reagent, or
   f$_6$) performing a coupling reaction under peptide coupling conditions, and
   g) optionally saponifying the obtained product.

11. The method of claim 10, further comprising at least the following step after step (g):
   h) performing a coupling reaction under peptide coupling conditions with alkylamines.

12. A method for treating a human or animal disease selected from the group consisting of liver cancer, pancreatic cancer, lung cancer, breast cancer, prostate cancer, leukemias, renal cancer, endometrial cancer, colorectal cancer, chemoresistant cancers and macular degeneration, comprising administering the compound of claim 1 to a patient in need thereof.

13. A method for inhibiting protein kinases selected from the group consisting of BRAF, EGFR, FGFR2, KDR, PDGFRA, SRC, ABL, FGFR1, VEGFR1, PDGFRB, ABL2, BLK, BMX, BTK, CSK, EPHA1, EPHA2, EPHA4, EPHB2, EPHB4, HER2, ERBB4, FES, FGR, FLT3, FMS, FRK, FYN, HCK, LCK, LYN, MAPK14, ERK2, PKC theta, RET, VEGFR3 and YES, in diseases, comprising administering the compound of claim 1 to a patient in need thereof.

14. The method of claim 13, wherein the disease is selected from the group consisting of liver cancer, pancreatic cancer, lung cancer, breast cancer, prostate cancer, leukemias, renal cancer, endometrial cancer, colorectal cancer, chemoresistant cancers, and macular degeneration.

15. An in vitro method for predicting whether a patient in need thereof, is likely to respond to at least one of the compounds according to claim 1, which method comprises determining the expression levels, gene modifications, activation state or appearance of a mutated form of the protein kinase in a sample of said patient, wherein said protein kinase is selected from the following list of kinases BRAF, EGFR, FGFR2, KDR, PDGFRA, SRC, ABL, FGFR1, VEGFR1, PDGFRB, ABL2, BLK, BMX, BTK, CSK, EPHA1, EPHA2, EPHA4, EPHB2, EPHB4, HER2, ERBB4, FES, FGR, FLT3, FMS, FRK, FYN, HCK, LCK, LYN, MAPK14, ERK2, PKC theta, RET, VEGFR3 and YES.

16. In vitro method for predicting whether a patient in need thereof, is likely to respond to at least one of the compounds according to claim 1, which method comprises determining the expression levels, gene modifications, activation state or appearance of a mutated form of the protein kinase in a sample of said patient, wherein said protein kinase is selected from the following list of kinases BRAF, EGFR, FGFR2, KDR, PDGFRA, SRC, ABL, FGFR1, VEGFR1, PDGFRB, ABL2, BLK, BMX, BTK, CSK, EPHA1, EPHA2, EPHA4, EPHB2, EPHB4, HER2, ERBB4, FES, FGR, FLT3, FMS, FRK, FYN, HCK, LCK, LYN, MAPK14, ERK2, PKC theta, RET, VEGFR3 and YES, characterized in that it comprises the following steps:
   i) putting into contact said compound(s) with a sample of human tissue or cells,
   j) determination of the activity of the compound(s) on the sample via for example IC50 and/or via a compared activity of the protein kinases present, which can for example be chosen from the following list of kinases BRAF, EGFR, EGFR T790M L858R, FGFR2, KDR PDGFRA and SRC
   k) optionally conducting the same test as step i) with healthy cells of said patient to determine the toxicity of the compound according to claim 1 to healthy cells,
   h) selecting the compound according to claim 1 presenting the best activity, and/or eventually lowest toxicity, to be administered to the patient in need thereof.

17. The compound of claim 1 characterized in that R7, R8, R9, R10 and R11 are all hydrogen atoms.

18. The method of claim 13, wherein the disease is selected from the group consisting of tumorigenesis, human immune disorders, inflammatory diseases, thrombotic diseases, neurodegenerative diseases, bone diseases, macular degeneration, fibrosis, cystogenesis, hyperproliferative diseases, and cancers.

19. A pharmaceutical composition, comprising, as an active ingredient, the compound of claim 1 and a pharmaceutically acceptable excipient.

20. A method for inhibiting protein kinases selected from the group consisting of BRAF, EGFR, FGFR2, KDR, PDGFRA, SRC, ABL, FGFR1, VEGFR1, PDGFRB, ABL2, BLK, BMX, BTK, CSK, EPHA1, EPHA2, EPHA4, EPHB2, EPHB4, HER2, ERBB4, FES, FGR, FLT3, FMS, FRK, FYN, HCK, LCK, LYN, MAPK14, ERK2, PKC theta, RET, VEGFR3 and YES, in diseases comprising administering the pharmaceutical composition of claim 19 to a patient in need thereof.

21. A method for treating a human or animal disease selected from the group consisting of liver cancer, pancreatic cancer, lung cancer, breast cancer, prostate cancer, leukemias, renal cancer, endometrial cancer, colorectal cancer, chemoresistant cancers and macular degeneration, comprising administering the pharmaceutical composition of claim 19 to a patient in need thereof.

* * * * *